US008138161B2

(12) United States Patent
Han et al.

(10) Patent No.: US 8,138,161 B2
(45) Date of Patent: Mar. 20, 2012

(54) MODIFIED SMALL INTERFERING RNA MOLECULES AND METHODS OF USE

(75) Inventors: Jang Han, Lafayette, CA (US); Michael Houghton, Danville, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 336 days.

(21) Appl. No.: 11/664,008

(22) PCT Filed: Sep. 30, 2005

(86) PCT No.: PCT/US2005/035493
§ 371 (c)(1),
(2), (4) Date: Feb. 28, 2008

(87) PCT Pub. No.: WO2006/039656
PCT Pub. Date: Apr. 13, 2006

(65) Prior Publication Data
US 2008/0269148 A1 Oct. 30, 2008

Related U.S. Application Data

(60) Provisional application No. 60/614,955, filed on Oct. 1, 2004.

(51) Int. Cl.
*A61K 48/00* (2006.01)
*C07H 21/02* (2006.01)
*C07H 21/04* (2006.01)
(52) U.S. Cl. ......... 514/44; 536/23.1; 536/536; 536/24.5
(58) Field of Classification Search .................. None
See application file for complete search history.

(56) References Cited

U.S. PATENT DOCUMENTS

| 5,610,054 | A | 3/1997 | Draper |
| 6,107,027 | A | 8/2000 | Kay et al. |
| 6,133,246 | A | 10/2000 | McKay et al. |
| 6,174,868 | B1 | 1/2001 | Anderson et al. |
| 6,506,559 | B1 | 1/2003 | Fire et al. |
| 7,718,632 | B2 | 5/2010 | Van Heeke et al. |
| 2003/0143732 | A1 | 7/2003 | Fosnaugh et al. |
| 2003/0153519 | A1* | 8/2003 | Kay et al. ................. 514/44 |
| 2003/0206887 | A1 | 11/2003 | Morrissey et al. |
| 2003/0219823 | A1 | 11/2003 | Alsobrook, II et al. |
| 2004/0192626 | A1 | 9/2004 | McSwiggen et al. |
| 2004/0209831 | A1* | 10/2004 | McSwiggen et al. ..... 514/44 |
| 2005/0085528 | A1* | 4/2005 | Ahola et al. ............. 514/423 |
| 2005/0209180 | A1 | 9/2005 | Jadhav et al. |
| 2005/0255487 | A1 | 11/2005 | Khvorova et al. |
| 2011/0166058 | A1 | 7/2011 | Hinkle et al. |

FOREIGN PATENT DOCUMENTS

| EP | 1 532 248 B1 | 1/2009 |
| WO | WO 03/079757 A2 | 10/2003 |
| WO | WO 2004/009769 A2 | 1/2004 |
| WO | WO 2004/011647 A1 | 2/2004 |
| WO | WO 2004/042024 A2 | 5/2004 |
| WO | WO 2004/065546 A2 | 8/2004 |
| WO | WO 2005/112636 A2 | 12/2005 |
| WO | WO 2007/076328 A2 | 7/2007 |

OTHER PUBLICATIONS

Elbashir, et al. (2001) Functional Anatomy of siRNAs for Mediating Efficient RNAi in *Drosophila melanogaster* Embryo Lysate. EMBO J., v.20(23):6877-88.*
Czauderna et al.; "Structural variations and stabilising modifications of synthetic siRNAs in mammalian cells"; Nucleic Acids Research; 31(11):2705-2716 (2003).
Dias et al.; "Antisense Oligonucleotides: Basic Concepts and Mechanisms"; Mol. Cancer Ther.; 1:347-355 (2002).
Doherty et al.; "Ribozyme Structures andMechanisms"; Annu. Rev. Biophys. Biomol. Struct.; 30:457-475 (2001).
Dorsett et al.; siRNAs: Applications in Functional Genomics and Potential as Therapeutics; Nature Reviews—Drug Discovery; 3:318-329 (2004).
Elbashir et al.; "Duplexes of 21±nucleotide RNAs mediate RNA interference in cultured mammalian cells"; Nature—Letters to Nature; 411:494-498 (2001).
Jarczak et al.; "Hairpin ribozymes in combination with siRNAs against highly conserved hepatitis C virus sequence inhibit RNA replication and protein translation from hepatitis C virus subgenomic replicons"; FEBS Journal; 272:5910-5922 (2005).
Kawasaki et al.; "World of small RNAs: from ribozymes to siRNA and miRNA"; Differentiation; 72:58-64 (2004).
Kruger et al.; "Involvement of Proteasome Alpha-Subunit PSMA7 in Hepatitis C Virus Internal Ribosome Entry Site-Mediated Translation"; Molecular and Cellular Biology; 21(24):8357-8364 (2001).
Lee et al.; "Pharmacokinetics and Tissue Distribution of a Ribozyme Directed Against Hepatitis C Virus RNA Following Subcutaneous or Intravenous Administration in Mice"; Hepatology; 32(3):640-646 (2000).
Lieber et al.; "Elimination of Hepatitis C Virus RNA in Infected Human Hepatocytes by Adenovirus-Mediated Expression of Ribozymes"; Journal of Virology; 70(12):8782-8791 (1996).
Macejak et al.; "Inhibition of Hepatitis C Virus (HCV)-RNA-Dependent Translation and Replication of a Chimeric HCV Poliovirus Using Synthetic Stabilized Ribozymes"; Hepatology; 31(3):769-776 (2000).
Macejak et al.; "Enhanced antiviral effect in cell culture of type 1 interferon and ribozymes targeting HCV RNA"; Journal of Viral Hepatitis; 8:400-405 (2001).

(Continued)

*Primary Examiner* — Amy Bowman
(74) *Attorney, Agent, or Firm* — Frank Wu, Patent Agent

(57) ABSTRACT

The present invention provides double-stranded RNA molecules that mediate RNA interference in target cells, preferably hepatic cells. The invention also provides double-stranded RNA (dsRNA) molecules that are modified to be resistant to nuclease degradation, which inactivates a virus, and more specifically, hepatitis C virus (HCV). The invention also provides a method of using these modified RNA molecules to inactivate virus in mammalian cells and a method of making modified small interfering RNAs (siRNAs) using human Dicer. The invention provides modified RNA molecules that are modified to include a dsRNA or siRNA wherein one or more of the pyrimidines in the RNA molecule are modified to include 2'-Fluorine. The invention also provides dsRNA or siRNA in which all pyrimidines are modified to include a 2'-Fluorine. The invention provides that the 2'-Fluorine dsRNA or siRNA molecule is further modified to include a two base deoxynucleotide "TT" sequence at the 3' end of the molecule.

18 Claims, 29 Drawing Sheets

OTHER PUBLICATIONS

Miyagishi et al.; "Comparison of the Suppressive Effects of Antisense Oligonucleotides and siRNAs Directed Against the Same Targets in Mammalian Cells"; Antisense and Nucleic Acid Drug Development; 13:1-7 (2003).

Ohkawa et al.; "Cleavage of viral RNA and inhibition of viral translation by hepatitis C virus RNA-specific hammerhead ribozyme in vitro"; Journal of Hepatology; 27:78-84 (1997).

Peracchi; "Prospects for antiviral ribozymes and deoxyribozymes"; Rev. Med. Virol.—Review; 14:47-64 (2004).

Puerta-Fernandez et al.; "Ribozymes: recent advances in the development of RNA tools"; FEMS Microbiology Reviews; 27:75-97 (2003).

Randall et al.; "Clearance of replicating hepatitis C virus replicon RNAs in cell culture by small interfering RNAs"; PNAS; 100(1):235-240 (2003).

Ryu et al.; "Identification of the Most Accessible Sites to Ribozymes on the Hepatitis C Virus Internal Ribosome Entry Site"; Journal of Biochemistry and Molecular Biology; 36(6):538-544 (2003).

Ryu et al.; "Note: Comparative Analysis of Intracellular Trans-Splicing Ribozyme Activity Against Hepatitis C Virus Internal Ribosome Entry Site"; The Journal of Microbiology; 42(4):361-364 (2004).

Sakamoto et al.; "Intracellular Cleavage of Hepatitis C Virus RNA and Inhibition of Viral Protein Translation by Hammerhead Ribozymes"; J. Clin. Invest.; 98:2720-2728 (1996).

von Weizsacker et al.; "Gene Therapy for Chronic Viral Hepatitis: Ribozymes, Antisense Oligonucleotides, and Dominant Negative Mutants"; Hepatology—Concise Review; 26(2):251-255 (1997).

Wang et al.; "Subsection E: Methods of RGS Protein Inhibition—[15] Ribozyme- and siRNA-Mediated Suppression of RGS-Containing RhoGEF Proteins"; Methods in Enzymology; 389:244-265 (2004).

Welch et al.; "Ribozyme gene therapy for hepatitis C virus infection"; Clinical and Diagnostic Virology; 10:163-171 (1998).

Yu et al.; "Activity of HDV ribozymes to trans-cleave HCV RNA"; World J. Gastroenterol.; 8(4):694-698 (2002).

Kraynack et al.; "Small interfering RNAs containing full 2'-O-methylribonucleotide-modified sense strands display Argonaute2/eIF2C2-dependent activity"; RNA; 12(1):163-176 (2006).

Elbashir, Sayda M. et al., "Functional anatomy of siRNAs for mediating efficient RNAi in *Drosophila melanogaster* embryo lysate" The EMBO Journal, 2001, pp. 6877-6888, vol. 20, No. 23.

Elbashir, Sayda M. et al., "RNA interference is mediated by 21- and 22-nucleotide RNAs" Genes Dev., 2001, pp. 188-200, vol. 15, Cold Spring Harbor Laboratory Press.

Guerniou et al.; "Targeted inhibition of the hepatitis C internal ribosomal entry site genomic RNA with oligonucleotide conjugates"; Nucleic Acids Research; 35(20):6778-6787 (2007).

Kapadia et al.; "Interference of hepatitis C virus RNA replication by short interfering RNAs"; PNAS; 100(4):2014-2018 (2003).

Kim et al.; "Inhibition of hepatitis C virus gene expression by small interfering RNAs using a tri-cistronic full-length viral replicon and a transient mouse model"; Virus Research; 122:1-10 (2006).

Martinand-Mari et al.; "Oligonucleotide-based Strategies to Inhibit Human Hepatitis C Virus"; Oligonucleotides—Review; 13:539-548 (2003).

\* cited by examiner

Fig. 1. The Sequence and Secondary Structure of 5'UTR of HCV Genome.

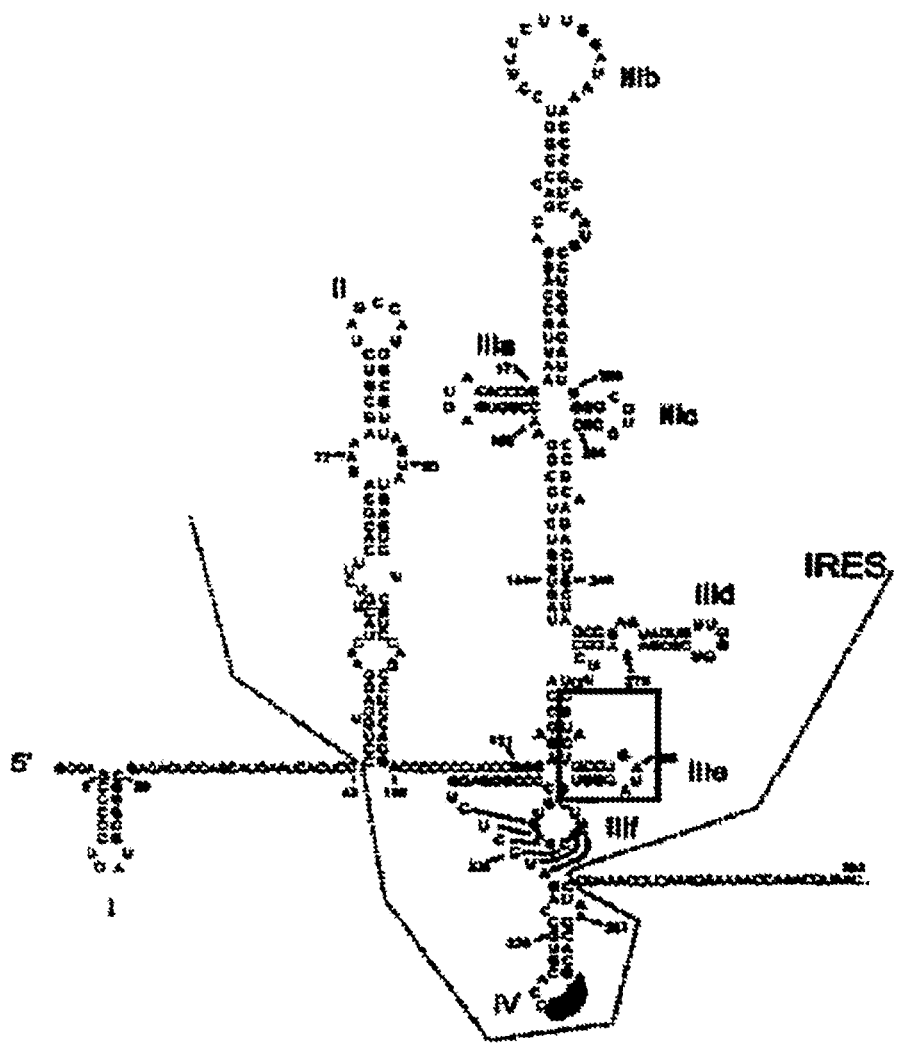

The region where siRNAs was designed is boxed.
The sequence of the 21-bp siRNA$_5$ is shown below.

```
          286                    304
siRNA$_5$  5'-GUACUGCCUGAUAGGGUGCUU
           UUCAUGACGGACUAUCCCACG-5'

GL2        5'-CGUACGCGGAAUACUUCGAUU
           UUGCAUGCGCCUUAUGAAGCU-5'

GL3        5'-CUUACGCUGAGUACUUCGAUU
           UUGAAUGCGACUCAUGAAGCU-5'

SIN        5'-AUCUCUACGGUGGUCCUAAUU
           UUUAGAGAUGCCACCAGGAUU-5'
```

Fig. 2

| | Domain | sequence (NN-N19-NN) | Position | | |
|---|---|---|---|---|---|
| 5U8 | 5'UTR | cc-CUGUGAGGAACUACUGUCU-uc | 45-63 | sense | CUGUGAGGAACUACUGUCUUC |
| | | | | antisense | AGACAGUAGUUCCUCACAGGG |
| 5U9 | | ua-CUGUCUUCACGCAGAAAGC-gu | 58-76 | sense | CUGUCUUCACGCAGAAAGCGU |
| | | | | antisense | GCUUUCUGCGUGAAGACAGUA |
| 5U10 | | cg-AGACUGCUAGCCGAGUAGU-gu | 244-262 | sense | AGACUGCUAGCCGAGUAGUGU |
| | | | | antisense | ACUACUCGGCUAGCAGUCUCG |
| C1 | Core | ga-AUCCUAAACCUCAAAGAAA-aa | 352-370 | sense | AUCCUAAACCUCAAAGAAAAA |
| | | | | antisense | UUUCUUUGAGGUUUAGGAUUC |
| C2 | | gg-UCAGAUCGUCGGUGGAGUU-ua | 425-443 | sense | UCAGAUCGUCGGUGGAGUUUA |
| | | | | antisense | AACUCCACCGACGAUCUGACC |
| C3 | | gg-UAAGGUCAUCGAUACCCUC-ac | 701-719 | sense | UAAGGUCAUCGAUACCCUCAC |
| | | | | antisense | GAGGGUAUCGAUGACCUUACC |
| C4 | | ac-GGCGUGAACUAUGCAACAG-gg | 822-840 | sense | GGCGUGAACUAUGCAACAGGG |
| | | | | antisense | CUGUUGCAUAGUUCACGCCGU |
| C5 | | cc-GGUUGCUCCUUUUCUAUCU-uc | 852-870 | sense | GGUUGCUCCUUUUCUAUCUUC |
| | | | | antisense | AGAUAGAAAAGGAGCAACCGG |
| 5B1 | NS5B | gc-UCUUCAUACGGAUUCCAAU-ac | 8163-8181 | sense | UCUUCAUACGGAUUCCAAUAC |
| | | | | antisense | AUUGGAAUCCGUAUGAAGAGC |
| 5B2 | | ca-UACGGAUUCCAAUACUCUC-cu | 8167-8187 | sense | UACGGAUUCCAAUACUCUCCU |
| | | | | antisense | GAGAGUAUUGGAAUCCGUAUG |
| 5B3 | | uu-UGACUCAACGGUCACUGAG-aa | 8270-8288 | sense | UGACUCAACGGUCACUGAGAA |
| | | | | antisense | CUCAGUGACCGUUGAGUCAAA |
| 5B4 | | cc-UUCACGGAGGCUAUGACUA-ga | 8613-8631 | sense | UUCACGGAGGCUAUGACUAGA |
| | | | | antisense | UAGUCAUAGCCUCCGUGAAGG |
| 5B5 | | au-ACGACUUGGAGUUGAUAAC-au | 8671-8689 | sense | ACGACUUGGAGUUGAUAACAU |
| | | | | antisense | GUUAUCAACUCCAAGUCGUAU |
| 5B6 | | au-UCCUGGCUAGGCAACAUCA-uc | 8817-8835 | sense | UCCUGGCUAGGCAACAUCAUC |
| | | | | antisense | UGAUGUUGCCUAGCCAGGAAU |
| 5B7 | | uu-GUGGCAAGUACCUCUUCAA-cu | 9160-9178 | sense | GUGGCAAGUACCUCUUCAACU |
| | | | | antisense | UUGAAGAGGUACUUGCCACAA |
| 5B8 | | au-GUGGUGCCUACUCCUACUU-uc | 9317-9335 | sense | GUGGUGCCUACUCCUACUUUC |
| | | | | antisense | AAGUAGGAGUAGGCACCACAU |
| 3U1 | 3'UTR | cu-UUGGUGGCUCCAUCUUAGC-cc | 9506-9524 | sense | UUGGUGGCUCCAUCUUAGCCC |
| | | | | antisense | GCUAAGAUGGAGCCACCAAAG |
| 3U2 | | gu-CACGGCUAGCUGUGAAAGG-uc | 9531-9549 | sense | CACGGCUAGCUGUGAAAGGUC |
| | | | | antisense | CCUUUCACAGCUAGCCGUGAC |
| 3U3 | | ag-CCGCUUGACUGCAGAGAGU-gc | 9558-9576 | sense | CCGCUUGACUGCAGAGAGUGC |
| | | | | antisense | ACUCUCUGCAGUCAAGCGGCU |

Fig. 3

```
   1 ttattaggtt tttacctacc caggaaaagc caaccaacct cgatctcttg tagatctgtt
  61 ctctaaacga actttaaaat ctgtgtagct gtcgctcggc tgcatgccta gtgcacctac
 121 gcagtataaa caataataaa ttttactgtc gttgacaaga aacgagtaac tcgtccctct
 181 tctgcagact gcttacggtt tcgtccgtgt tgcagtcgat catcagcata cctaggtttc
 241 gtccgggtgt gaccgaaagg taagatggag agccttgttc ttggtgtcaa cgagaaaaca
 301 cacgtccaac tcagtttgcc tgtccttcag gttagagacg tgctagtgcg tggcttcggg
 361 gactctgtgg aagaggccct atcggaggca cgtgaacacc tcaaaaatgg cacttgtggt
 421 ctagtagagc tggaaaaagg cgtactgccc cagcttgaac agccctatgt gttcattaaa
 481 cgttctgatg ccttaagcac caatcacggc cacaaggtcg ttgagctggt tgcagaaatg
 541 gacggcattc agtacggtcg tagcggtata acactgggag tactcgtgcc acatgtgggc
 601 gaaaccccaa ttgcataccg caatgttctt cttcgtaaga acggtaataa gggagccggt
 661 ggtcatagct atggcatcga tctaaagtct tatgacttag gtgacgagct tggcactgat
 721 cccattgaag attatgaaca aaactggaac actaagcatg gcagtggtgc actccgtgaa
 781 ctcactcgtg agctcaatgg aggtgcagtc actcgctatg tcgacaacaa tttctgtggc
 841 ccagatgggt accctcttga ttgcatcaaa gattttctcg cacgcgcggg caagtcaatg
 901 tgcactcttt ccgaacaact tgattacatc gagtcgaaga gaggtgtcta ctgctgccgt
 961 gaccatgagc atgaaattgc ctggttcact gagcgctctg ataagagcta cgagcaccag
1021 acaccctttcg aaattaagag tgccaagaaa tttgacactt tcaaagggga atgcccaaag
1081 tttgtgtttc ctcttaactc aaaagtcaaa gtcattcaac cacgtgttga aagaaaaag
1141 actgagggtt tcatgggggcg tatacgctct gtgtaccctg ttgcatctcc acaggagtgt
1201 aacaatatgc acttgtctac cttgatgaaa tgtaatcatt gcgatgaagt ttcatggcag
1261 acgtgcgact ttctgaaagc cacttgtgaa cattgtggca ctgaaaattt agttattgaa
1321 ggacctacta catgtgggta cctacctact aatgctgtag tgaaaatgcc atgtcctgcc
1381 tgtcaagacc cagagattgg acctgagcat agtgttgcag attatcacaa ccactcaaac
1441 attgaaactc gactccgcaa gggaggtagg actagatgtt ttggaggctg tgtgtttgcc
1501 tatgttggct gctataataa gcgtgcctac tgggttcctc gtgctagtgc tgatattggc
1561 tcaggccata ctggcattac tggtgacaat gtggagacct tgaatgagga tctccttgag
1621 atactgagtc gtgaacgtgt taacattaac attgttggcg attttcattt gaatgaagag
1681 gttgccatca tttggcatc tttctctgct tctacaagtg cctttattga cactataaag
1741 agtcttgatt acaagtctt caaaaccatt gttgagtcct gcggtaacta taaagttacc
1801 aagggaaagc ccgtaaaagg tgcttggaac attggacaac agagatcagt tttaacacca
1861 ctgtgtggtt ttccctcaca ggctgctggt gttatcagat caatttttgc gcgcacactt
1921 gatgcagcaa accactcaat tcctgatttg caaagagcag ctgtcaccat acttgatggt
1981 attttctgaac agtcattacg tcttgtcgac gccatggttt atacttcaga cctgctcacc
2041 aacagtgtca ttattatggc atatgtaact ggtggtcttg tacaacagac ttctcagtgg
2101 ttgtctaatc ttttgggcac tactgttgaa aaactcaggc ctatcttga atggattgag
2161 gcgaaactta gtgcaggagt tgaatttctc aaggatgctt gggagattct caaatttctc
2221 attacaggtg ttttgacat cgtcaagggt caaatacagg ttgcttcaga taacatcaag
2281 gattgtgtaa aatgcttcat tgatgttgtt aacaaggcac tcgaaatgtg cattgatcaa
2341 gtcactatcg ctggcgcaaa gttgcgatca ctcaacttag gtgaagtctt catcgctcaa
2401 agcaagggac tttaccgtca gtgtatacgt ggcaaggagc agctgcaact actcatgcct
2461 cttaaggcac caaaagaagt aacctttctt gaaggtgatt cacatgacac agtacttacc
2521 tctgaggagg ttgttctcaa gaacggtgaa ctcgaagcac tcgagacgcc cgttgatagc
2581 ttcacaaatg gagctatcgt cggcacacca gtctgtgtaa atggcctcat gctcttagag
2641 attaaggaca aagaacaata ctgcgcattg tctcctggtt tactggctac aaacaatgtc
2701 tttcgcttaa aagggggtgc accaattaaa ggtgtaacct tggagaaga tactgttgg
2761 gaagttcaag gttacaagaa tgtgagaatc acatttgagc ttgatgaacg tgttgacaaa
```

(cont.)

```
2821 gtgcttaatg aaaagtgctc tgtctacact gttgaatccg gtaccgaagt tactgagttt
2881 gcatgtgttg tagcagaggc tgttgtgaag actttacaac cagtttctga tctccttacc
2941 aacatgggta ttgatcttga tgagtggagt gtagctacat tctacttatt tgatgatgct
3001 ggtgaagaaa acttttcatc acgtatgtat tgttccttt accctccaga tgaggaagaa
3061 gaggacgatg cagagtgtga ggaagaagaa attgatgaaa cctgtgaaca tgagtacggt
3121 acagaggatg attatcaagg tctccctctg gaatttggtg cctcagctga aacagttcga
3181 gttgaggaag aagaagagga agactggctg gatgatacta ctgagcaatc agagattgag
3241 ccagaaccag aacctacacc tgaagaacca gttaatcagt ttactggtta tttaaaactt
3301 actgacaatg ttgccattaa atgtgttgac atcgttaagg aggcacaaag tgctaatcct
3361 atggtgattg taaatgctgc taacatacac ctgaaacatg gtggtggtgt agcaggtgca
3421 ctcaacaagg caaccaatgg tgccatgcaa aaggagagtg atgattacat taagctaaat
3481 ggccctctta cagtaggagg gtcttgtttg ctttctggac ataatcttgc taagaagtgt
3541 ctgcatgttg ttggacctaa cctaaatgca ggtgaggaca tccagcttct taaggcagca
3601 tatgaaaatt tcaattcaca ggacatctta cttgcaccat tgttgtcagc aggcatattt
3661 ggtgctaaac cacttcagtc tttacaagtg tgcgtgcaga cggttcgtac acaggtttat
3721 attgcagtca atgacaaagc tctttatgag caggttgtca tggattatct tgataacctg
3781 aagcctagag tggaagcacc taaacaagag gagccaccaa acacagaaga ttccaaaact
3841 gaggagaaat ctgtcgtaca gaagcctgtc gatgtgaagc aaaaaattaa ggcctgcatt
3901 gatgaggtta ccacaacact ggaagaaact aagtttctta ccaataagtt actcttgttt
3961 gctgatatca atggtaagct ttaccatgat tctcagaaca tgcttagagg tgaagatatg
4021 tcttttccttg agaaggatgc accttacatg gtaggtgatg ttatcactag tggtgatatc
4081 acttgtgttg taataccctc caaaaaggct ggtggcacta ctgagatgct ctcaagagct
4141 ttgaagaaag tgccagttga tgagtatata accacgtacc ctggacaagg atgtgctggt
4201 tatacacttg aggaagctaa gactgctctt aagaaatgca aatctgcatt ttatgtacta
4261 ccttcagaag cacctaatgc taaggaagag attctaggaa ctgtatcctg gaatttgaga
4321 gaaatgcttg ctcatgctga agagacaaga aaattaatgc ctatatgcat ggatgttaga
4381 gccataatgg caaccatcca acgtaagtat aaaggaatta aaattcaaga gggcatcgtt
4441 gactatggtg tccgattctt ctttatact agtaaagagc ctgtagcttc tattattacg
4501 aagctgaact ctctaaatga gccgcttgtc acaatgccaa ttggttatgt gacacatggt
4561 tttaatcttg aagaggctgc gcgctgtatg cgttctctta agctcctgc cgtagtgtca
4621 gtatcatcac cagatgctgt tactacatat aatgataccc tcacttcgtc atcaaagaca
4681 tctgaggagc actttgtaga aacagtttct ttggctggct cttacagaga ttggtcctat
4741 tcaggacagc gtacagagtt aggtgttgaa tttcttaagc gtggtgacaa aattgtgtac
4801 cacactctgg agagccccgt cgagtttcat cttgacggtg aggttctttc acttgacaaa
4861 ctaaagagtc tcttatccct gcgggaggtt aagactataa aagtgttcac aactgtggac
4921 aacactaatc tccacacaca gcttgtggat atgtctatga catatggaca gcagtttggt
4981 ccaacatact ggatggtgc tgatgttaca aaaattaaac ctcatgtaaa tcatgagggt
5041 aagacttct ttgtactacc tagtgatgac acactacgta gtgaagcttt cgagtactac
5101 catactcttg atgagagttt tcttggtagg tacatgtctg ctttaaacca cacaaagaaa
5161 tggaaatttc ctcaagttgg tggtttaact tcaattaaat gggctgataa caattgttat
5221 ttgtctagtg ttttattagc acttcaacag cttgaagtca aattcaatgc accagcactt
5281 caagaggctt attatagagc ccgtgctggt gatgctgcta cttttgtgc actcatactc
5341 gcttacagta ataaaactgt tggcgagctt ggtgatgtca gagaaactat gacccatctt
5401 ctacagcatg ctaatttgga atctgcaaag cgagttctta atgtggtgtg taaacattgt
5461 ggtcagaaaa ctactacctt aacgggtgta gaagctgtga tgtatatggg tactctatct
5521 tatgataatc ttaagacagg tgtttccatt ccatgtgtgt gtggtcgtga tgctacacaa
5581 tatctagtac aacaagagtc ttcttttgtt atgatgtctg caccacctgc tgagtataaa
5641 ttacagcaag gtacattctt atgtgcgaat gagtacactg gtaactatca gtgtggtcat
5701 tacactcata taactgctaa ggagaccctc tatcgtattg acggagctca ccttacaaag
5761 atgtcagagt acaaaggacc agtgactgat gttttctaca aggaaacatc ttacactaca
5821 accatcaagc ctgtgtcgta taaactcgat ggagttactt acacagagat tgaaccaaaa
5881 ttggatgggt attataaaa ggataatgct tactatacag agcagcctat agaccttgta
5941 ccaactcaac cattaccaaa tgcgagtttt gataattca actcacatg ttctaacaca
6001 aaatttgctg atgatttaaa tcaaatgaca ggcttcacaa agccagcttc acgagagcta
6061 tctgtcacat tcttcccaga cttgaatggc gatgtagtgg ctattgacta tagacactat
6121 tcagcgagtt tcaagaaagg tgctaaatta ctgcataagc caattgtttg gcacattaac
```

Fig. 3 (cont.)

```
6181 caggctacaa ccaagacaac gttcaaacca aacacttggt gttacgttg tctttggagt
6241 acaaagccag tagatacttc aaattcattt gaagttctgg cagtagaaga cacacaagga
6301 atggacaatc ttgcttgtga aagtcaacaa cccacctctg aagaagtagt ggaaaatcct
6361 accatacaga aggaagtcat agagtgtgac gtgaaaacta ccgaagttgt aggcaatgtc
6421 atacttaaac catcagatga aggtgttaaa gtaacacaag agttaggtca tgaggatctt
6481 atggctgctt atgtggaaaa cacaagcatt accattaaga aacctaatga gctttcacta
6541 gccttaggtt taaaaacaat tgccactcat ggtattgctg caattaatag tgttccttgg
6601 agtaaaattt tggcttatgt caaaccattc ttaggacaag cagcaattac aacatcaaat
6661 tgcgctaaga gattagcaca acgtgtgttt aacaattata tgccttatgt gtttacatta
6721 ttgttccaat tgtgtacttt tactaaaagt accaattcta gaattagagc ttcactacct
6781 acaactattg ctaaaaatag tgttaagagt gttgctaaat tatgtttgga tgccggcatt
6841 aattatgtga agtcacccaa attttctaaa ttgttcacaa tcgctatgtg gctattgttg
6901 ttaagtattt gcttaggttc tctaatctgt gtaactgctg cttttggtgt actcttatct
6961 aattttggtg ctccttctta ttgtaatggc gttagagaat tgtatcttaa ttcgtctaac
7021 gttactacta tggatttctg tgaaggttct tttccttgca gcattgttt aagtggatta
7081 gactcccttg attcttatcc agctcttgaa accattcagg tgacgatttc atcgtacaag
7141 ctagacttga caatttaggg tctggccgct gagtgggttt tggcatatat gttgttcaca
7201 aaattctttt atttattagg tctttcagct ataatgcagg tgttcttgg ctattttgct
7261 agtcatttca tcagcaattc ttggctcatg tggtttatca ttagtattgt acaaatggca
7321 cccgttctg caatggttag gatgtacatc ttctttgctt ctttctacta catatggaag
7381 agctatgttc atatcatgga tggttgcacc tcttcgactt gcatgatgtg ctataagcgc
7441 aatcgtgcca cacgcgttga gtgtacaact attgttaatg gcatgaagag atctttctat
7501 gtctatgcaa atggaggccg tggcttctgc aagactcaca attggaattg tctcaattgt
7561 gacacatttt gcactggtag tacattcatt agtgatgaag ttgctcgtga tttgtcactc
7621 cagtttaaaa gaccaatcaa ccctactgac cagtcatcgt atattgttga tagtgttgct
7681 gtgaaaaatg gcgcgcttca cctctacttt gacaaggctg tcaaaagac ctatgagaga
7741 catccgctct cccattttgt caatttagac aatttgagag ctaacaacac taaaggttca
7801 ctgccatatta atgtcatagt ttttgatggc aagtccaaat gcgacgagtc tgcttctaag
7861 tctgcttctg tgtactacag tcagctgatg tgccaaccta ttctgttgct tgaccaagct
7921 cttgtatcag acgttggaga tagtactgaa gttccgtta agatgtttga tgcttatgtc
7981 gacacctttt cagcaacttt tagtgttcct atggaaaaac ttaaggcact tgttgctaca
8041 gctcacagcg agttagcaaa gggtgtagct ttagatggtg tcctttctac attcgtgtca
8101 gctgcccgac aaggtgttgt tgataccgat gttgacacaa aggatgttat tgaatgtctc
8161 aaactttcac atcactctga cttagaagtg acaggtgaca gttgtaacaa tttcatgctc
8221 acctataata aggttgaaaa catgacgccc agagatcttg gcgcatgtat tgactgtaat
8281 gcaaggcata tcaatgccca agtagcaaaa agtcacaatg tttcactcat ctggaatgta
8341 aaagactaca tgtctttatc tgaacagctg cgtaaacaaa ttcgtagtgc tgccaagaag
8401 aacaacatac cttttagact aacttgtgct acaactagac aggttgtcaa tgtcataact
8461 actaaaatct cactcaaggg tggtaagatt gttagtactt gttttaaact tatgcttaag
8521 gccacattat tgtgcgttct tgctgcattg gtttgttata tcgttatgcc agtacataca
8581 ttgtcaatcc atgatggtta cacaaatgaa atcattggtt acaaagccat tcaggatggt
8641 gtcactcgtg acatcatttc tactgatgat tgtttttgcaa ataaacatgc tggttttgac
8701 gcatggttta gccagcgtgg tggttcatac aaaaaatgaca aaagctgccc tgtagtagct
8761 gctatcatta caagagagat tggtttcata gtgcctggct taccgggtac tgtgctgaga
8821 gcaatcaatg gtgacttctt gcattttcta cctcgtgttt ttagtgctgt tgcaacatt
8881 tgctacacac cttccaaact cattgagtat agtgattttg ctacctctgc ttgcgttctt
8941 gctgctgagt gtacaatttt taaggatgct atgggcaaac ctgtgccata ttgttatgac
9001 actaatttgc tagagggttc tatttcttat agtgagcttc gtccagacac tcgttatgtg
9061 cttatggatg gttccatcat acagtttcct aacacttacc tggagggttc tgttagagta
9121 gtaacaactt ttgatgctga gtactgtaga catggtacat gcgaaaggtc agaagtaggt
9181 atttgcctat ctaccagtgg tagatgggtt cttaataatg agcattacag agctctatca
9241 ggagttttct gtggtgttga tgcgatgaat ctcatagcta acatctttac tcctcttgtg
9301 caacctgtgg gtgcttttaga tgtgtctgct tcagtagtgg ctggtggtat tattgccata
9361 ttggtgactt gtgctgccta ctactttatg aaattcagac gtgttttgg tgagtacaac
9421 catgttgttg ctgctaatgc acttttgttt ttgatgtctt tcactatact ctgtctggta
9481 ccagcttaca gctttctgcc gggagtctac tcagtctttt acttgtactt gacattctat
```

Fig. 3 (cont.)

```
9541 ttcaccaatg atgtttcatt cttggctcac cttcaatggt ttgccatgtt ttctcctatt
9601 gtgcctttt ggataacagc aatctatgta ttctgtattt ctctgaagca ctgccattgg
9661 ttcttaaca actatcttag gaaaagagtc atgtttaatg gagttacatt tagtaccttc
9721 gaggaggctg ctttgtgtac cttttgctc aacaaggaaa tgtacctaaa attgcgtagc
9781 gagacactgt tgccacttac acagtataac aggtatcttg ctctatataa caagtacaag
9841 tatttcagtg gagccttaga tactaccagc tatcgtgaag cagcttgctg ccacttagca
9901 aaggctctaa atgactttag caactcaggt gctgatgttc tctaccaacc accacagaca
9961 tcaatcactt ctgctgttct gcagagtggt tttaggaaaa tggcattccc gtcaggcaaa
10021 gttgaagggt gcatggtaca agtaacctgt ggaactacaa ctcttaatgg attgtggttg
10081 gatgacacag tatactgtcc aagacatgtc atttgcacag cagaagacat gcttaatcct
10141 aactatgaag atctgctcat tgcaaatcc aaccatagct ttcttgttca ggctggcaat
10201 gttcaacttc gtgttattgg ccattctatg caaaattgtc tgcttaggct taaagttgat
10261 acttctaacc ctaagacacc caagtataaa tttgtccgta tccaacctgg tcaaacattt
10321 tcagttctag catgctacaa tggttcacca tctggtgttt atcagtgtgc catgagacct
10381 aatcatacca ttaaaggttc tttccttaat ggatcatgtg gtagtgttgg ttttaacatt
10441 gattatgatt gcgtgtcttt ctgctatatg catcatatgg agcttccaac aggagtacac
10501 gctggtactg acttagaagg taaattctat ggtccatttg ttgacagaca aactgcacag
10561 gctgcaggta cagacacaac cataacatta aatgttttgg catggctgta tgctgctgtt
10621 atcaatggtg ataggtggtt tcttaataga ttcaccacta ctttgaatga cttaaccctt
10681 gtggcaatga agtacaacta tgaacctttg acacaagatc atgttgacat attgggacct
10741 ctttctgctc aaacaggaat tgccgtctta gatatgtgtg ctgctttgaa agagctgctg
10801 cagaatggta tgaatggtcg tactatcctt ggtagcacta tttagaaga tgagtttaca
10861 ccattgatg ttgttagaca atgctctggt gttaccttcc aaggtaagtt caagaaaatt
10921 gttaagggca ctcatcattg gatgctttta actttcttga catcactatt gattcttgtt
10981 caaagtacac agtggtcact gtttttcttt gtttacgaga atgctttctt gccatttact
11041 cttggtatta tggcaattgc tgcatgtgct atgctgcttg ttaagcataa gcacgcattc
11101 ttgtgcttgt tctgttacc ttctcttgca acagttgctt acttaatat ggtctacatg
11161 cctgctagct gggtgatgcg tatcatgaca tggcttgaat tggctgacac tagcttgtct
11221 ggttataggc ttaaggattg tgttatgtat gcttcagctt tagtttgct tattctcatg
11281 acagctcgca ctgttatga tgatgctgct agacgtgttt ggacactgat gaatgtcatt
11341 acacttgttt acaaagtcta ctatggtaat gctttagatc aagctatttc catgtgggcc
11401 ttagttattt ctgtaacctc taactattct ggtgtcgtta cgactatcat gtttttagct
11461 agagctatag tgtttgtgtg tgttgagtat tacccattgt tatttattac tggcaacacc
11521 ttacagtgta tcatgcttgt ttattgtttc ttaggctatt gttgctgctg ctacttttggc
11581 cttttctgtt tactcaaccg ttacttcagg cttactcttg gtgtttatga ctacttggtc
11641 tctacacaag aatttaggta tatgaactcc caggggcttt tgcctcctaa gagtagtatt
11701 gatgctttca gcttaacat taagttgttg ggtattggag gtaaaccatg tatcaaggtt
11761 gctactgtac agtctaaaat gtctgacgta aagtgcacat ctgtggtact gctctcggtt
11821 cttcaacaac ttagagtaga gtcatcttct aaaattgtggg cacaatgtgt acaactccac
11881 aatgatattc ttcttgcaaa agacacaact gaagctttcg agaagatggt ttctcttttg
11941 tctgttttgc tatccatgca gggtgctgta gacattaata ggttgtgcga ggaaatgctc
12001 gataaccgtg ctactcttca ggctattgct tcagaattta gttctttacc atcatatgcc
12061 gcttatgcca ctgcccagga ggcctatgag caggctagt ctaatggtga ttctgaagtc
12121 gttctcaaaa agttaaagaa atctttgaat gtggctaaat ctgagtttga ccgtgatgct
12181 gccatgcaac gcaagttgga aaagatggca gatcaggcta tgacccaaat gtacaaacag
12241 gcaagatctg aggacaagag ggcaaaagta actagtgcta tgcaaacaat gctcttcact
12301 atgcttagga agcttgataa tgatgcactt aacaacatta tcaacaatgc gcgtgatggt
12361 tgtgttccac tcaacatcat accattgact acagcagcca aatcatggt tgttgtccct
12421 gattatggta ccacaagaa cacttgtgat ggtaacacct tacatatgc atctgcactc
12481 tgggaaatcc agcaagtgt tgatgcggat agcaagattg ttcaacttag tgaaattaac
12541 atggacaatt caccaaattt ggcttggcct cttattgtta cagctctaag agccaactca
12601 gctgttaaac tacagaataa tgaactgagt ccagtagcac tacgacagat gtcctgtgcg
12661 gctggtacca cacaaacagc ttgtactgat gacaatgcac ttgcctacta taacaattcg
12721 aagggaggta ggtttgtgct ggcattacta tcagaccacc aagatctcaa atgggctaga
12781 ttccctaaga gtgatggtac aggtacaatt tacacagaac tgaaccacc ttgtaggttt
12841 gttacagaca caccaaaagg gcctaaagtg aaatactgt acttcatcaa aggcttaaac
```

Fig. 3 (cont.)

```
12901 aacctaaata gaggtatggt gctgggcagt ttagctgcta cagtacgtct tcaggctgga
12961 aatgctacag aagtacctgc caattcaact gtgctttcct tctgtgcttt tgcagtagac
13021 cctgctaaag catataagga ttacctagca agtggaggac aaccaatcac caactgtgtg
13081 aagatgttgt gtacacacac tggtacagga caggcaatta ctgtaacacc agaagctaac
13141 atggaccaag agtcctttgg tggtgcttca tgttgtctgt attgtagatg ccacattgac
13201 catccaaatc ctaaaggatt ctgtgacttg aaaggtaagt acgtccaaat acctaccact
13261 tgtgctaatg acccagtggg ttttacactt agaaacacag tctgtaccgt ctgcggaatg
13321 tggaaaggtt atggctgtag ttgtgaccaa ctccgcgaac ccttgatgca gtctgcggat
13381 gcatcaacgt ttttaaacgg gtttgcggtg taagtgcagc ccgtcttaca ccgtgcggca
13441 caggcactag tactgatgtc gtctacaggg cttttgatat ttacaacgaa aaagttgctg
13501 gttttgcaaa gttcctaaaa actaattgct gtcgcttcca ggagaaggat gaggaaggca
13561 atttattaga ctcttacttt gtagttaaga ggcatactat gtctaactac caacatgaag
13621 agactattta taacttggtt aaagattgtc cagcggttgc tgtccatgac tttttcaagt
13681 ttagagtaga tggtgacatg gtaccacata tatcacgtca gcgtctaact aaatacacaa
13741 tggctgattt agtctatgct ctacgtcatt ttgatgaggg taattgtgat acattaaaag
13801 aaatactcgt cacatacaat tgctgtgatg atgattattt caataagaag gattggtatg
13861 acttcgtaga gaatcctgac atcttacgcg tatatgctaa cttaggtgag cgtgtacgcc
13921 aatcattatt aaagactgta caattctgcg atgctatgcg tgatgcaggc attgtaggcg
13981 tactgacatt agataatcag gatcttaatg ggaactggta cgatttcggt gatttcgtac
14041 aagtagcacc aggctgcgga gttcctattg tggattcata ttactcattg ctgatgccca
14101 tcctcacttt gactagggca ttggctgctg agtcccatat ggatgctgat ctcgcaaaac
14161 cacttattaa gtgggattttg ctgaaatatg attttacgga agagagactt tgtctcttcg
14221 accgttattt taaatattgg gaccagacat accatcccaa ttgtattaac tgtttggatg
14281 ataggtgtat ccttcattgt gcaaacttta atgtgttatt tctactgtg tttccaccta
14341 caagttttgg accactagta agaaaaatat ttgtagatgg tgttcctttt gttgtttcaa
14401 ctgatacca ttttcgtgag ttaggagtcg tacataatca ggatgtaaac ttacatagct
14461 cgcgtctcag tttcaaggaa ctttagtgt atgctgctga tccagctatg catgcagctt
14521 ctgcaatttt attgctagat aaacgcacta catgctttc agtagctgca ctaacaaaca
14581 atgttgcttt tcaaactgtc aaacccggta atttaataa agactttat gactttgct
14641 tgtctaaagg tttctttaag gaaggaagtt ctgttgaact aaaacacttc ttctttgctc
14701 aggatggcaa cgctgctatc agtgattatg actattatcg ttataatctg ccaacaatgt
14761 gtgatatcag acaactccta ttcgtagttg aagtgttga taaatacttt gattgttacg
14821 atggtggctg tattaatgcc aaccaagtaa tcgttaacaa tctggataaa tcagctggtt
14881 tcccatttaa taaatggggt aaggctagac tttattatga ctcaatgagt tatgaggatc
14941 aagatgcact ttcgcgtat actaagcgta atgtcatccc tactataact caaatgaatc
15001 ttaagtatgc cattagtgca aagaatagag ctcgcaccgt agctggtgtc tctatctgta
15061 gtactatgac aaatagacag tttcatcaga aattattgaa gtcaatagcc gccactagag
15121 gagctactgt ggtaattgga acaagcaagt tttacggtgg ctgcataat atgttaaaaa
15181 ctgtttacag tgatgtagaa actccacacc ttatgggttg ggattatcca aaatgtgaca
15241 gagccatgcc taacatgctt aggataatgg cctctcttgt tcttgctcgc aaacataaca
15301 cttgctgtaa cttatcacac cgtttctaca ggttagctaa cgagtgtgcg caagtattaa
15361 gtgagatggt catgtgtggc ggctcactat atgttaaacc aggtggaaca tcatccggtg
15421 atgctacaac tgcttatgct aatagtgtct ttaacatttg tcaagctgtt acagccaatg
15481 taaatgcact tctttcaact gatggtaata gatagctga caagtatgtc cgcaatctac
15541 aacacaggct ctatgagtgt ctctatagaa ataggatgt tgatcatgaa ttcgtggatg
15601 agtttacgc ttacctgcgt aaacatttct ccatgatgat tctttctgat gatgccgttg
15661 tgtgctataa cagtaactat gcggctcaag gtttagtagc tagcattaag aactttaagg
15721 cagttcttta ttatcaaaat aatgtgttca tgtctgaggc aaaatgttgg actgagactg
15781 accttactaa aggacctcac gaatttgct cacagcatac aatgctagtt aaacaaggag
15841 atgattacgt gtacctgcct tacccagatc catcaagaat attaggcgca ggctgttttg
15901 tcgatgatat tgtcaaaaca gatggtacac ttatgattga aaggttcgtg tcactggcta
15961 ttgatgctta cccacttaca aaacatccta atcaggagta tgctgatgtc tttcacttgt
16021 atttacaata cattagaaag ttacatgatg agcttactgg ccacatgttg gacatgtatt
16081 ccgtaatgct aactaatgat aacacctcac ggtactggga acctgagttt tatgaggcta
16141 tgtacacacc acatacagtc ttgcaggctg taggtgcttg tgtattgtgc aattcacaga
16201 cttcacttcg ttgcggtgcc tgtattagga gaccattcct atgttgcaag tgctgctatg
```

Fig. 3 (cont.)

```
16261 accatgtcat ttcaacatca cacaaattag tgttgtctgt taatccctat gtttgcaatg
16321 ccccaggttg tgatgtcact gatgtgacac aactgtatct aggaggtatg agctattatt
16381 gcaagtcaca taagcctccc attagttttc cattatgtgc taatggtcag gtttttggtt
16441 tatacaaaaa cacatgtgta ggcagtgaca atgtcactga cttcaatgcg atagcaacat
16501 gtgattggac taatgctggc gattacatac ttgccaacac ttgtactgag agactcaagc
16561 ttttcgcagc agaaacgctc aaagccactg aggaaacatt taagctgtca tatggtattg
16621 ccactgtacg cgaagtactc tctgacagag aattgcatct ttcatgggag gttggaaaac
16681 ctagaccacc attgaacaga aactatgtct tactggtta ccgtgtaact aaaaatagta
16741 aagtacagat tggagagtac acctttgaaa aaggtgacta tggtgatgct gttgtgtaca
16801 gaggtactac gacatacaag ttgaatgttg gtgattactt tgtgttgaca tctcacactg
16861 taatgccact tagtgcacct actctagtgc cacaagagca ctatgtgaga attactggct
16921 tgtacccaac actcaacatc tcagatgagt tttctagcaa tgttgcaaat tatcaaaagg
16981 tcggcatgca aaagtactct acactccaag gaccacctgg tactggtaag agtcattttg
17041 ccatcggact tgctctctat tacccatctg ctcgcatagt gtatacggca tgctctcatg
17101 cagctgttga tgccctatgt gaaaaggcat taaaatattt gcccatagat aaatgtagta
17161 gaatcatacc tgcgcgtgcg cgcgtagagt gttttgataa attcaaagtg aattcaacac
17221 tagaacagta tgttttctgc actgtaaatg cattgccaga aacaactgct gacattgtag
17281 tctttgatga aatctctatg gctactaatt atgacttgag tgttgtcaat gctagacttc
17341 gtgcaaaaca ctacgtctat attggcgatc ctgctcaatt accagccccc cgcacattgc
17401 tgactaaagg cacactagaa ccagaatatt taattcagt gtgcagactt atgaaaacaa
17461 taggtccaga catgttcctt ggaacttgtc gccgttgtcc tgctgaaatt gttgacactg
17521 tgagtgcttt agtttatgac aataagctaa aagcacacaa ggataagtca gctcaatgct
17581 tcaaaatgtt ctacaaaggt gttattacac atgatgtttc atctgcaatc aacagacctc
17641 aaataggcgt tgtaagagaa ttcttacac gcaatcctgc ttggagaaaa gctgttttta
17701 tctcacctta taattcacag aacgctgtag cttcaaaaat cttaggattg cctacgcaga
17761 ctgttgattc atcacagggt tctgaatatg actatgtcat attcacacaa actactgaaa
17821 cagcacactc ttgtaatgtc aaccgcttca atgtggctat cacaagggca aaaattggca
17881 ttttgtgcat aatgtctgat agagatcttt atgacaaact gcaatttaca agtctagaaa
17941 taccacgtcg caatgtggct acattacaag cagaaaatgt aactggactt tttaaggact
18001 gtagtaagat cattactggt cttcatccta cacaggcacc tacacacctc agcgttgata
18061 taaagttcaa gactgaagga ttatgtgttg acataccagg cataccaaag gacatgacct
18121 accgtagact catctctatg atgggtttca aaatgaatta ccaagtcaat ggttaccccta
18181 atatgtttat cacccgcgaa gaagctattc gtcacgttcg tgcgtggatt ggctttgatg
18241 tagagggctg tcatgcaact agagatgctg tgggtactaa cctacctctc cagctaggat
18301 tttctacagg tgttaactta gtagctgtac cgactggtta tgttgacact gaaaataaca
18361 cagaattcac cagagttaat gcaaaacctc caccaggtga ccagttaaa catcttatac
18421 cactcatgta taaaggcttg ccctggaatg tagtgcgtat taagatagta caaatgctca
18481 gtgatacact gaaaggattg tcagacagag tcgtgttcgt cctttgggcg catggcttg
18541 agcttacatc aatgaagtac tttgtcaaga ttggacctga agaacgtgt tgtctgtgtg
18601 acaaacgtgc aacttgcttt tctacttcat cagatactta tgcctgctgg aatcattctg
18661 tgggttttga ctatgtctat aacccattta tgattgatgt tcagcagtgg ggctttacgg
18721 gtaaccttca gagtaaccat gaccaacatt gccaggtaca tggaaatgca catgtggcta
18781 gttgtgatgc tatcatgact agatgttag cagtccatga gtgctttgtt aagcgcgttg
18841 attggtctgt tgaataccct attataggag atgaactgag ggttaattct gcttgcagaa
18901 aagtacaaca catggttgtg aagtctgcat tgcttgctga taagttccca gttcttcatg
18961 acattggaaa tccaaaggct atcaagtgtg tgcctcaggc tgaagtagaa tggaagttct
19021 acgatgctca gccatgtagt gacaaagctt acaaaataga ggaactcttc tattcttatg
19081 ctacacatca cgataaattc actgatggtg tttgttgtt ttggaattgt aacgttgatc
19141 gttacccagc caatgcaatt gtgtgtaggt ttgacacaag agtcttgtca aacttgaact
19201 taccaggctg tgatggtggt agtttgtatg tgaataagca tgcattccac actccagctt
19261 tcgataaaag tgcatttact aatttaaagc aattgccttt cttttactat tctgatagtc
19321 cttgtgagtc tcatggcaaa caagtagtgt cggatattga ttatgttcca ctcaaatctg
19381 ctacgtgtat tacacgatgc aatttaggtg gtgctgtttg cagacaccat gcaaatgagt
19441 accgacagta cttggatgca tataatatga tgatttctgc tggatttagc ctatggattt
19501 acaaacaatt tgatacttat aacctgtgga atacatttac caggttacag agtttagaaa
19561 atgtggcttt aatgttgtt aataaaggac actttgatgg acacgccggc gaagcacctg
```

Fig. 3 (cont.)

```
19621 tttccatcat taataatgct gtttacacaa aggtagatgg tattgatgtg gagatctttg
19681 aaaataagac aacacttcct gttaatgttg catttgagct ttgggctaag cgtaacatta
19741 aaccagtgcc agagattaag atactcaata atttgggtgt tgatatcgct gctaatactg
19801 taatctggga ctacaaaaga gaagccccag cacatgtatc tacaataggt gtctgcacaa
19861 tgactgacat tgccaagaaa cctactgaga gtgcttgttc ttcacttact gtcttgtttg
19921 atggtagagt ggaaggacag gtagaccttt ttagaaacgc ccgtaatggt gttttaataa
19981 cagaaggttc agtcaaaggt ctaacacctt caaagggacc agcacaagct agcgtcaatg
20041 gagtcacatt aattggagaa tcagtaaaaa cacagtttaa ctactttaag aaagtagacg
20101 gcattattca acagttgcct gaaacctact ttactcagag cagagactta gaggatttta
20161 agcccagatc acaaatggaa actgactttc tcgagctcgc tatggatgaa ttcatacagc
20221 gatataagct cgagggctat gccttcgaac acatcgttta tggagatttc agtcatggac
20281 aacttggcgg tcttcattta atgataggct tagccaagcg ctcacaagat tcaccactta
20341 aattagagga ttttatccct atggacagca cagtgaaaaa ttacttcata acagatgcgc
20401 aaacaggttc atcaaaatgt gtgtgttctg tgattgatct tttacttgat gactttgtcg
20461 agataataaa gtcacaagat ttgtcagtga tttcaaaagt ggtcaaggtt acaattgact
20521 atgctgaaat ttcattcatg ctttggtgta aggatggaca tgttgaaacc ttctacccaa
20581 aactacaagc aagtcgagcg tggcaaccag gtgttgcgat gcctaacttg tacaagatgc
20641 aaagaatgct tcttgaaaag tgtgaccttc agaattatgg tgaaaatgct gttataccaa
20701 aaggaataat gatgaatgtc gcaaagtata ctcaactgtg tcaatactta aatacactta
20761 ctttagctgt accctacaac atgagagtta ttcactttgg tgctggctct gataaaggag
20821 ttgcaccagg tacagctgtg ctcagacaat ggttgccaac tggcacacta cttgtcgatt
20881 cagatcttaa tgacttcgtc tccgacgcat attctacttt aattggagac tgtgcaacag
20941 tacatacggc taataaatgg gaccttatta ttagcgatat gtatgacccc aggaccaaac
21001 atgtgacaaa agagaatgac tctaaagaag ggttttcac ttatctgtgt ggatttataa
21061 agcaaaaact agccctgggt ggttctatag ctgtaaagat aacagagcat tcttggaatg
21121 ctgaccttta caagcttatg ggccatttct catggtggac agcttttgtt acaaatgtaa
21181 atgcatcatc atcggaagca ttttttaattg gggctaacta tcttggcaag ccgaaggaac
21241 aaattgatgg ctataccatg catgctaact acatttctg gaggaacaca aatcctatcc
21301 agttgtcttc ctattcactc tttgacatga gcaaatttcc tcttaaaatta gaggaactg
21361 ctgtaatgtc tcttaaggag aatcaaatca atgatatgat ttattctctt ctggaaaaag
21421 gtaggcttat cattagagaa aacaacagag ttgtggttc aagtgatatt cttgttaaca
21481 actaaacgaa catgtttatt ttcttattat ttcttactct cactagtggt agtgaccttg
21541 accggtgcac cacttttgat gatgttcaag ctcctaatta cactcaacat acttcatcta
21601 tgaggggggt ttactatcct gatgaaattt ttagatcaga cactcttat ttaactcagg
21661 atttatttct tccattttat tctaatgtta cagggtttca tactattaat catacgtttg
21721 gcaaccctgt catacctttt aaggatggta tttatttgc tgccacagag aaatcaaatg
21781 ttgtccgtgg ttgggttttt ggttctacca tgaacaacaa gtcacagtcg gtgattatta
21841 ttaacaattc tactaatgtt gttatacgag catgtaactt tgaattgtgt gacaacccct
21901 tctttgctgt ttctaaaccc atgggtacac agacacatac tatgatattc gataatgcat
21961 ttaattgcac tttcgagtac atatctgatg ccttttcgct tgatgtttca gaaaagtcag
22021 gtaattttaa acacttacga gagtttgtgt ttaaaaataa agatgggttt ctctatgttt
22081 ataagggcta tcaacctata gatgtagttc gtgatctacc ttctggtttt aacactttga
22141 aacctatttt taagttgcct cttggtatta acattacaaa ttttagagcc attctacag
22201 ccttttcacc tgctcaagac atttggggca cgtcagctgc agcctatttt gttggctatt
22261 taaagccaac tacatttatg ctcaagtatg atgaaaatgg tacaatcaca gatgctgttg
22321 attgttctca aaatccactt gctgaactca aatgctctgt taagagcttt gagattgaca
22381 aggaatttta ccagacctct aatttcaggg ttgttcccct caggagatgtt gtgagattcc
22441 ctaatattac aaacttgtgt ccttttggag aggttttaa tgctactaaa ttcccttctg
22501 tctatgcatg ggagagaaaa aaaatttcta attgtgttgc tgattactct gtgctctaca
22561 actcaacatt tttttcaacc tttaagtgct atggcgtttc tgccactaag ttgaatgatc
22621 tttgcttctc caatgtctat gcagattctt ttgtagtcaa gggagatgat gtaagacaaa
22681 tagcgccagg acaaactggt gttattgctg attataatta taaattgcca gatgatttca
22741 tgggttgtgt ccttgcttgg aatactagga acattgatgc tacttcaact ggtaattata
22801 attataaata taggtatctt agacatggca agcttaggcc ctttgagaga gacatatcta
22861 atgtgccttt ctcccctgat ggcaaacctt gcacccacc tgctcttaat tgttattggc
22921 cattaaatga ttatggtttt tacaccacta ctggcattgg ctaccaacct tacagagttg
```

Fig. 3 (cont.)

```
22981 tagtactttc ttttgaactt ttaaatgcac cggccacggt ttgtggacca aaattatcca
23041 ctgaccttat taagaaccag tgtgtcaatt ttaattttaa tggactcact ggtactggtg
23101 tgttaactcc ttcttcaaag agatttcaac catttcaaca atttggccgt gatgtttctg
23161 atttcactga ttccgttcga gatcctaaaa catctgaaat attagacatt tcaccttgcg
23221 cttttggggg tgtaagtgta attacacctg gaacaaatgc ttcatctgaa gttgctgttc
23281 tatatcaaga tgttaactgc actgatgttt ctacagcaat tcatgcagat caactcacac
23341 cagcttggcg catatattct actggaaaca atgtattcca gactcaagca ggctgtctta
23401 taggagctga gcatgtcgac acttcttatg agtgcgacat tcctattgga gctggcattt
23461 gtgctagtta ccatacagtt tctttattac gtagtactag ccaaaaatct attgtggctt
23521 atactatgtc tttaggtgct gatagttcaa ttgcttactc taataacacc attgctatac
23581 ctactaactt ttcaattagc attactacag aagtaatgcc tgtttctatg gctaaaacct
23641 ccgtagattg taatatgtac atctgcggag attctactga atgtgctaat ttgcttctcc
23701 aatatggtag cttttgcaca caactaaatc gtgcactctc aggtattgct gctgaacagg
23761 atcgcaacac acgtgaagtg ttcgctcaag tcaaacaaat gtacaaaacc ccaactttga
23821 aatattttgg tggttttaat ttttcacaaa tattacctga ccctctaaag ccaactaaga
23881 ggtcttttat tgaggacttg ctctttaata aggtgacact cgctgatgct ggcttcatga
23941 agcaatatgg cgaatgccta ggtgatatta tgctagaga tctcatttgt gcgcagaagt
24001 tcaatggact tacagtgttg ccacctctgc tcactgatga tatgattgct gcctacactg
24061 ctgctctagt tagtggtact gccactgctg gatggacatt tggtgctggc gctgctcttc
24121 aaataccttt tgctatgcaa atggcatata ggttcaatgg cattggagtt acccaaaatg
24181 ttctctatga gaaccaaaaa caaatcgcca accaatttaa caaggcgatt agtcaaattc
24241 aagaatcact tacaacaaca tcaactgcat tgggcaagct gcaagacgtt gttaaccaga
24301 atgctcaagc attaaacaca cttgttaaac aacttagctc taattttggt gcaatttcaa
24361 gtgtgctaaa tgatatcctt tcgcgacttg ataaagtcga ggcggaggta caaattgaca
24421 ggttaattac aggcagactt caaagccttc aaacctatgt aacacaacaa ctaatcaggg
24481 ctgctgaaat cagggcttct gctaatcttg ctgctactaa aatgtctgag tgtgttcttg
24541 gacaatcaaa aagagttgac ttttgtggaa agggctacca ccttatgtcc ttcccacaag
24601 cagccccgca tggtgttgtc ttcctacatg tcacgtatgt gccatcccag gagaggaact
24661 tcaccacagc gccagcaatt tgtcatgaag caaagcata cttccctcgt gaaggtgttt
24721 ttgtgtttaa tggcacttct tggtttatta cacagaggaa cttcttttct ccacaaataa
24781 ttactacaga caatacattt gtctcaggaa attgtgatgt cgttattggc atcattaaca
24841 acacagttta tgatcctctg caacctgagc ttgactcatt caaagaagag ctggacaagt
24901 acttcaaaaa tcatacatca ccagatgttg atcttggcga catttcaggc attaacgctt
24961 ctgtcgtcaa cattcaaaaa gaaattgacc gcctcaatga ggtcgctaaa aatttaaatg
25021 aatcactcat tgaccttcaa gaattgggaa aatatgagca atatattaaa tggccttggt
25081 atgtttggct cggcttcatt gctggactaa ttgccatcgt catggttaca atcttgcttt
25141 gttgcatgac tagttgttgc agttgcctca agggtgcatg ctcttgtggt tcttgctgca
25201 agtttgatga ggatgactct gagccagttc tcaagggtgt caaattacat tacacataaa
25261 cgaacttatg gatttgttta tgagatttt tactcttgga tcaattactg cacagccagt
25321 aaaaattgac aatgcttctc ctgcaagtac tgttcatgct acagcaacga taccgctaca
25381 agcctcactc ccttcggat ggcttgttat tggcgttgca tttcttgctg ttttcagag
25441 cgctaccaaa ataattgcgc tcaataaaag atggcagcta gcccttata agggcttcca
25501 gttcatttgc aatttactgc tgctatttgt taccatctat tcacatcttt gcttgtcgc
25561 tgcaggtatg gaggcgcaat tttgtacct ctatgccttg atatatttc tacaatgcat
25621 caacgcatgt agaattatta tgagatgttg gctttgttgg aagtgcaaat ccaagaaccc
25681 attacttat gatgccaact acttgttg ctggcacaca cataactatg actactgtat
25741 accatataac agtgtcacag atacaattgt cgttactgaa ggtgacggca ttcaacacc
25801 aaaactcaaa gaagactacc aaattggtgg ttattctgag gataggcact caggtgttaa
25861 agactatgtc gttgtacatg gctatttcac cgaagtttac taccagcttg agtctacaca
25921 aattactaca gacactggta ttgaaaatgc tacattcttc atctttaaca gcttgttaa
25981 agacccaccg aatgtgcaaa tacacacaat cgacggctct tcaggagttg ctaatccagc
26041 aatggatcca atttatgatg agccgacgac gactactagc gtgcctttgt aagcacaaga
26101 aagtgagtac gaacttatgt actcattcgt tcggaagaa acaggtacgt taatagttaa
26161 tagcgtactt ctttttcttg ctttcgtggt attcttgcta gtcacactag ccatccttac
26221 tgcgcttcga ttgtgtgcgt actgctgcaa tattgttaac gtgagtttag taaaaccaac
26281 ggtttacgtc tactcgcgtg ttaaaaatct gaactcttct gaaggagttc ctgatcttct
```

```
26341 ggtctaaacg aactaactat tattattatt ctgtttggaa ctttaacatt gcttatcatg
26401 gcagacaacg gtactattac cgttgaggag cttaaacaac tcctggaaca atggaaccta
26461 gtaataggtt tcctattcct agcctggatt atgttactac aatttgccta ttctaatcgg
26521 aacaggtttt tgtacataat aaagcttgtt ttcctctggc tcttgtggcc agtaacactt
26581 gcttgttttg tgcttgctgc tgtctacaga attaattggg tgactggcgg gattgcgatt
26641 gcaatggctt gtattgtagg cttgatgtgg cttagctact tcgttgcttc cttcaggctg
26701 tttgctcgta cccgctcaat gtggtcattc aacccagaaa caaacattct tctcaatgtg
26761 cctctccggg ggacaattgt gaccagaccg ctcatggaaa gtgaacttgt cattggtgct
26821 gtgatcattc gtggtcactt gcgaatggcc ggacactccc tagggcgctg tgacattaag
26881 gacctgccaa aagagatcac tgtggctaca tcacgaacgc tttcttatta caaattagga
26941 gcgtcgcagc gtgtaggcac tgattcaggt tttgctgcat acaaccgcta ccgtattgga
27001 aactataaat taaatacaga ccacgccggt agcaacgaca atattgcttt gctagtacag
27061 taagtgacaa cagatgtttc atcttgttga cttccaggtt acaatagcag agatattgat
27121 tatcattatg aggactttca ggattgctat ttggaatctt gacgttataa taagttcaat
27181 agtgagacaa ttatttaagc tctaactaa gaagaattat tcggagttag atgatgaaga
27241 acctatggag ttagattatc cataaaacga acatgaaaat tattctcttc ctgacattga
27301 ttgtatttac atcttgcgag ctatatcact atcaggagtg tgttagaggt acgactgtac
27361 tactaaaaga accttgccca tcaggaacat acgagggcaa ttcaccattt cacctcttg
27421 ctgacaataa atttgcacta acttgcacta gcacacactt tgcttttgct tgtgctgacg
27481 gtactcgaca tacctatcag ctgcgtgcaa gatcagtttc accaaaactt ttcatcagac
27541 aagaggaggt tcaacaagag ctctactcgc cactttttct cattgttgct gctctagtat
27601 ttttaatact ttgcttcacc attaagagaa agacagaatg aatgagctca ctttaattga
27661 cttctatttg tgcttttag cctttctgct attccttgtt ttaataatgc ttattatatt
27721 ttggttttca ctcgaaatcc aggatctaga agaaccttgt accaaagtct aaacgaacat
27781 gaaacttctc attgttttga cttgtatttc tctatgcagt tgcatatgca ctgtagtaca
27841 gcgctgtgca tctaataaac ctcatgtgct tgaagatcct tgtaaggtac aacactaggg
27901 gtaatactta tagcactgct tggctttgtg ctctaggaaa ggttttacct tttcatagat
27961 ggcacactat ggttcaaaca tgcacaccta atgttactat caactgtcaa gatccagctg
28021 gtggtgcgct tatagctagg tgttggtacc ttcatgaagg tcaccaaact gctgcattta
28081 gagacgtact tgttgtttta aataaacgaa caaattaaaa tgtctgataa tggaccccaa
28141 tcaaaccaac gtagtgcccc ccgcattaca tttggtggac ccacagattc aactgacaat
28201 aaccagaatg gaggacgcaa tgggcaagg ccaaaacagc gccgacccca aggtttaccc
28261 aataatactg cgtcttggtt cacagctctc actcagcatg gcaaggagga acttagattc
28321 cctcgaggcc agggcgttcc aatcaacacc aatagtggtc cagatgacca aattggctac
28381 taccgaagag ctacccgacg agttcgtggt ggtgacggca aaatgaaaga gctcagcccc
28441 agatggtact tctattacct aggaactggc ccagaagctt cacttcccta cggcgctaac
28501 aaagaaggca tcgtatgggt tgcaactgag ggagccttga atacacccaa agaccacatt
28561 ggcacccgca atcctaataa caatgctgcc accgtgctac aacttcctca aggaacaaca
28621 ttgccaaaag cttctacgc agagggaagc agaggcggca gtcaagcctc ttctcgctcc
28681 tcatcacgta gtcgcggtaa ttcaagaaat tcaactcctg gcagcagtag gggaaattct
28741 cctgctcgaa tggctagcgg aggtggtgaa actgccctcg cgctattgct gctagacaga
28801 ttgaaccagc ttgagagcaa agtttctggt aaaggccaac aacaacaagg ccaaactgtc
28861 actaagaaat ctgctgctga ggcatctaaa aagcctcgcc aaaaacgtac tgccacaaaa
28921 cagtacaacg tcactcaagc atttgggaga cgtggtccag aacaaaccca aggaaatttc
28981 ggggaccaag acctaatcag acaaggaact gattacaaac attggccgca aattgcacaa
29041 tttgctccaa gtgcctctgc attctttgga atgtcacgca ttggcatgga agtcacacct
29101 tcgggaacat ggctgactta tcatggagcc attaaattgg atgacaaaga tccacaattc
29161 aaagacaacg tcatactgct gaacaagcac attgacgcat acaaaacatt cccaccaaca
29221 gagcctaaaa aggacaaaaa gaaaaagact gatgaagctc agcctttgcc gcagagacaa
29281 aagaagcagc ccactgtgac tcttcttcct gcggctgaca tggatgattt ctccagacaa
29341 cttcaaaatt ccatgagtgg agcttctgct gattcaactc aggcataaac actcatgatg
29401 accacacaag gcagatgggc tatgtaaacg ttttcgcaat tccgttacg atacatagtc
29461 tactcttgtg cagaatgaat tctcgtaact aaacagcaca gtaggttta gttaactta
29521 atctcacata gcaatcttta atcaatgtgt aacattaggg aggacttgaa agagccacca
29581 cattttcatc gaggccacgc ggagtacgat cgagggtaca gtgaataatg ctagggagag
29641 ctgcctatat ggaagagccc taatgtgtaa aattaatttt agtagtgcta tccccatgtg
```

Fig. 3 (cont.)

29701 attttaatag cttcttagga gaatgacaaa aaaaaaaaaa aaaaaaaaaa a
//

Fig. 3 (cont.)

Fig. 5. The Subgenomic HCV Replicon Used to Test
The Efficacy of siRNA in Human Liver Cells
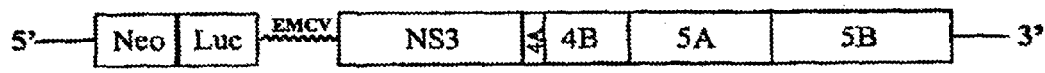
Neo: neomycin phosphotransferase gene
Luc: fruit fly luciferase
EMCV: internal ribosome entry site taken from EMCV
NS3, NS4A, NS4B, NS5A, and NS5B: HCV nonstructural proteins

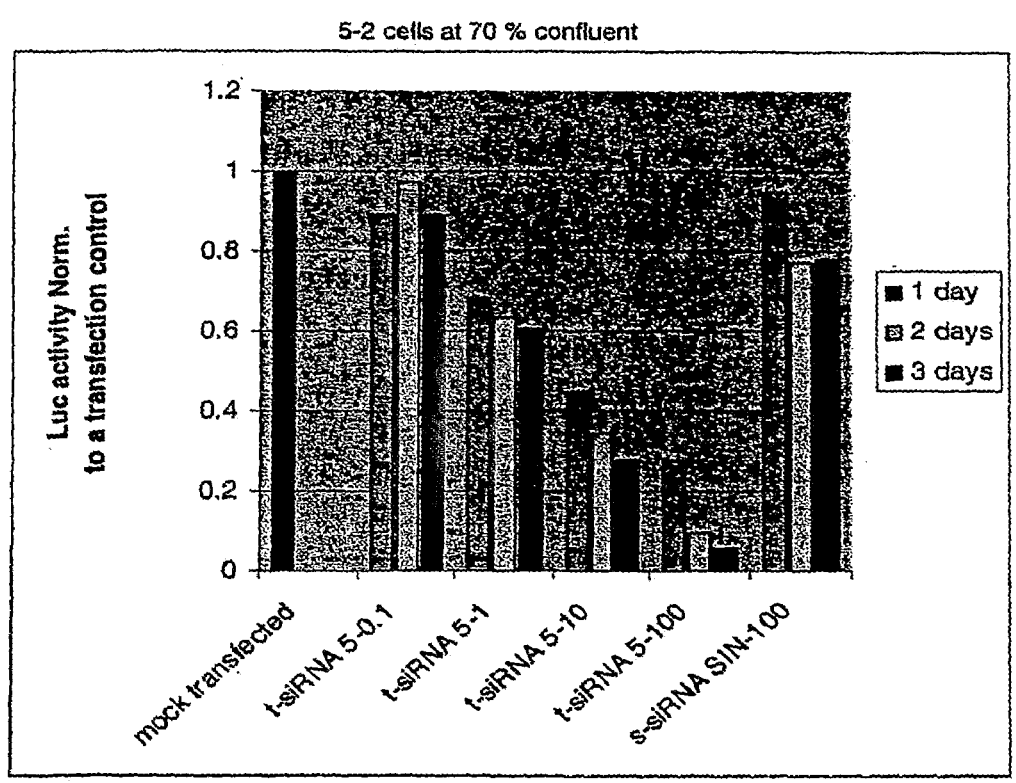
Fig. 6. The Effect of siRNA$_5$ on HCV Replication In Huh 5-2 Cells

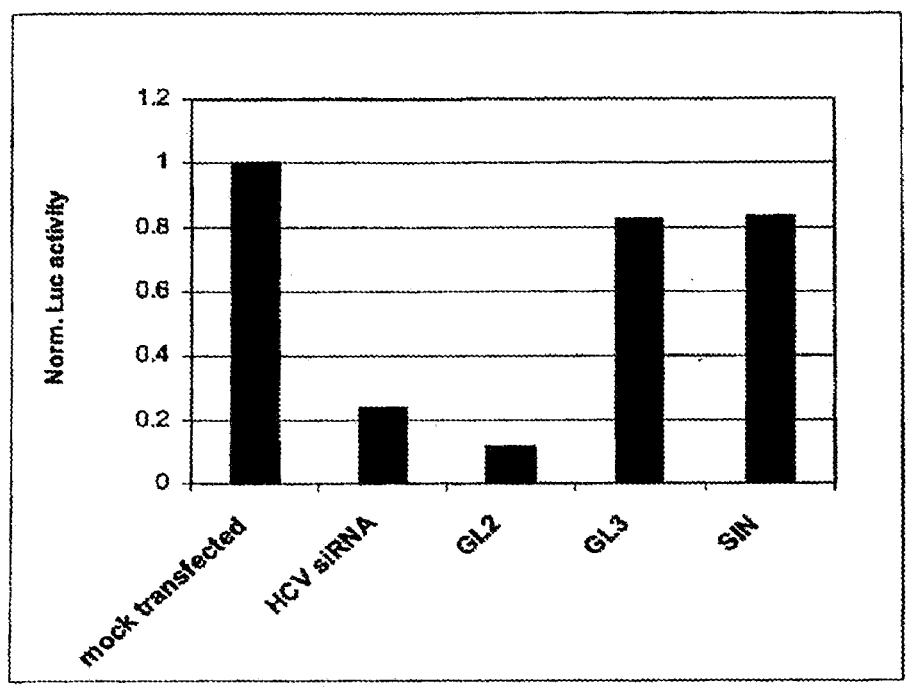
Fig. 7. Sequence Specificity Required for Mediating RNA Interference in Huh7 Cells Fig. 8. The Effect of siRNA5 of Cell Viability Measured by Cellular ATPase Activity
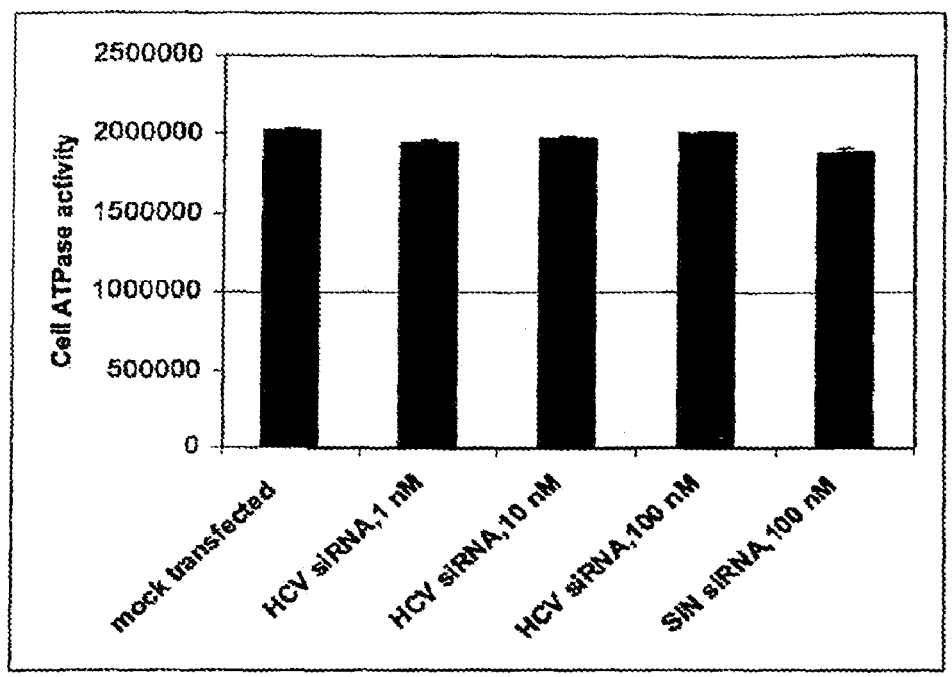
Fig. 9. The Effect of siRNA5 on HCV Replication in Huh-7 Cells Measured by HCV RNA Assay
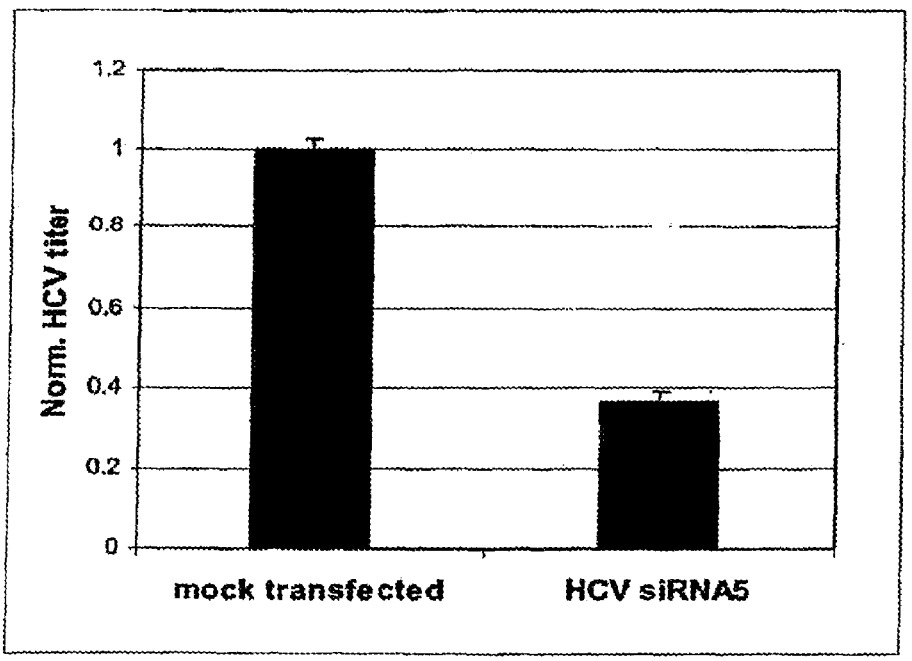

siRNA Stability can be Dramatically Increased by Fluorination within 2'-Sugar

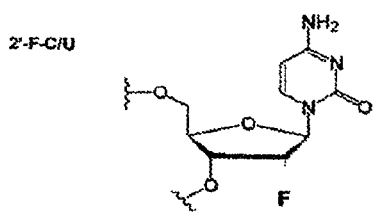

Known properties of 2'-F-chemistry:

- Fluorination of ANS destroys RNase-H activity.
- Fluorination of Rbz in catalytic site destroys enzymatic activity.
- Fluorination of siRNA does not affect siRNA activity
- Some 2'-F-nucleosides are toxic, but 2'-F-C/U are nontoxic: Toxicol. Pathology (1999) 27: 607-617

Unknown:
- Efficacy and safety in vivo

Figure 17

MODIFIED SMALL INTERFERING RNA MOLECULES AND METHODS OF USE

RELATED APPLICATIONS

This application is the U.S. National Phase of International Application No. PCT/US2005/035493, filed Sep. 30, 2005 and published in English, which claims the benefit of U.S. Provisional Application No. 60/614,955, filed Oct. 1, 2004. The teachings of the above applications are incorporated herein in their entirety by reference.

BACKGROUND OF THE INVENTION

The present invention relates to the field of nucleic acid detection and to the phenomenon of RNA silencing, or RNA interference (RNAi). RNA silencing constitutes a phenomenon wherein non-coding RNA molecules mediate specific gene suppression in an organism. In nature, the phenomenon protects an organism's genome from foreign, invading nucleic acids such as transposons, trangenes and viral genes.

The introduction of double-stranded RNA (dsRNA) into a cell triggers RNA silencing, which then degrades endogenous mRNA corresponding to the dsRNA. RNA silencing pathways involve a conversion of dsRNA into short interfering RNAs (siRNAs) that direct ribonucleases to homologous mRNA targets (Baulcombe et al., 2001). An enzyme called Dicer processes the dsRNA into siRNAs, which are 20-25 nucleotides long. The siRNAs then assemble into endoribonuclease-containing complexes known as RNA-induced silencing complexes (RISCs). Subsequently, the siRNAs guide the RISCs to complementary RNA molecules, where the RISCs cleave and destroy the target mRNA. Small amounts of dsRNA can silence a large amount of target mRNA due to an amplification component of RNA silencing (Fire et al., Nature, 391:806-811 (1998)).

The first evidence that dsRNA produces efficient gene silencing through RNAi came from studies on the nematode Caenorhabditis elegans (Fire et al., Nature, 391:806-811 (1998) and U.S. Pat. No. 6,506,559). Later studies in the fruit fly Drosophila melanogaster demonstrated that RNAi is a multi-step mechanism (Elbashir et al., Genes Dev., 15(2): 188-200 (2001)).

Although dsRNA can mediate gene-specific interference in mammalian cells (Wianny, F. and Zernicka-Goetz, M., Nature Cell Biol. 2:70-75 (2000) Svoboda, P. et al., Development 17:4147-4156 (2000)), the use of RNAi in mammalian somatic cells is often limited by a triggering of dsRNA-dependent protein kinase (PKR), which inactivates the translation factor eIF2a, causes a generalized suppression of protein synthesis and often times causes apoptosis (Gil, J. and Esteban, M., Apoptosis 5:107-114 (2000)).

Recently, siRNA of approximately 21 or 22 base pairs in length, corresponding to targeted RNA or DNA sequences, were shown to disrupt the expression of the targeted sequences in mammalian cells (Elbashir, S. M., et al., Nature 411: 494-498 (2001)). However, it is not clear that all RNA or DNA sequences of a mammalian cell's genome are susceptible to siRNA. It is also uncertain that every mammalian cell type possesses the necessary machinery for effectuating gene-specific suppression using siRNA. Further, siRNA is of limited use for at least two reasons: (a) the transient nature of the suppression effect seen in cells where the siRNA has been administered, and (b) the necessity for chemical synthesis of siRNAs before their use (Tuschl, T., Nature Biotech., 20: 446-448 (2002)). Also, since siRNAs are unstable in vivo, their long-term effectiveness is limited.

An invention that addresses these challenges will improve the utility of RNAi for treating human disease at the level of nucleic acid activity. In particular, such an invention will make RNAi a more practical therapy for viral infections, such as infections with HCV. Current therapies for such viral infections are very limited, and tend to have poor response rates.

SUMMARY OF THE INVENTION

In a first embodiment, the invention provides a double-stranded (dsRNA) molecule that mediates RNA interference in target cells wherein one or more of the pyrimidines in the dsRNA are modified to include a 2'-Fluorine.

In a second embodiment, the invention provides a small interfering RNA (siRNA) that mediates RNA interference in target cells wherein one or more of the pyrimidines in the siRNA are modified to include a 2'-Fluorine.

In a third embodiment, all of the pyrimidines in the dsRNA or siRNA molecules of the first and second embodiments are modified to include a 2'-Fluorine.

In a fourth embodiment, the 2'-Fluorine dsRNA or siRNA of the third embodiment's further modified to include a two base deoxynucleotide "TT" sequence at the 3' end of the dsRNA or siRNA.

In a fifth embodiment, the 2'-Fluorine dsRNA or siRNA of the third embodiment inhibits viral replication in infected cells.

In a sixth embodiment, the 2'-Fluorine dsRNA or siRNA of the fifth embodiment correspond to hepatitis C virus (HCV) nucleic acids and inhibit replication of HCV in hepatic cells.

In a seventh embodiment, there is provided a method for inactivating a virus in a patient comprising administering to said patient a 2'-Fluorine dsRNA or siRNA in an effective amount to inactivate said virus.

In an eighth embodiment, there is provided a method for inactivating a virus in a patient comprising administering to said patient a 2'-Fluorine dsRNA or siRNA in an effective amount to inactivate said virus, wherein all of the pyrimidines in the dsRNA or siRNA are modified to include a 2'-Fluorine.

In an ninth embodiment, there is provided a method for inactivating a virus in a patient comprising administering to said patient a 2'-Fluorine dsRNA or siRNA in an effective amount to inactivate said virus wherein the 2'-Fluorine dsRNA or siRNA is further modified to include a two base deoxynucleotide "TT" sequence at the 3' end of the dsRNA or siRNA.

In a tenth embodiment, there is provided a method for inactivating a virus in a patient comprising administering to said patient a 2'-Fluorine dsRNA or siRNA in an effective amount to inactivate said virus, wherein said virus is selected from the group consisting of hepatitis C virus (HCV), hepatitis A virus, hepatitis B virus, hepatitis D virus, hepatitis E virus, Ebola virus, influenza virus, rotavirus, reovirus, retrovirus, poliovirus, human papilloma virus (HPV), metapneumovirus and coronavirus.

In an eleventh embodiment, there is provided a method for inactivating a virus in a patient comprising administering to said patient a 2'-Fluorine dsRNA or siRNA in an effective amount to inactivate said virus, wherein said virus is HCV.

In a twelfth embodiment, there is provided a method of preparing an siRNA comprising the steps of:
 (a) identifying a target nucleotide sequence in an HCV genome for designing a siRNA; and
 (b) producing an siRNA that contains at least one pyrimidine in the siRNA which is modified to include a 2'-Fluorine.

In an thirteenth embodiment, there is provided a method of preparing an siRNA comprising the steps of:
 (a) identifying a target nucleotide sequence in an HCV genome for designing a siRNA; and
 (b) producing an siRNA wherein all of the pyrimidines in the siRNA are modified to include a 2'-Fluorine.

In a fourteenth embodiment, there is provided a method of preparing an siRNA comprising the steps of:
 (a) identifying a target nucleotide sequence in an HCV genome for designing a siRNA; and
 (b) producing an siRNA wherein all of the pyrimidines in the siRNA are modified to include a 2'-Fluorine and wherein the 2'-Fluorine siRNA is further modified to include a two base deoxynucleotide "TT" sequence at the 3' end of the dsRNA or siRNA.

In a fifteenth embodiment, wherein said target nucleotide sequence in the fourteenth embodiment is selected from the group consisting of 5'-untranslated region (5'-UTR), 3'-untranslated region (3'-UTR), core, and NS3 helicase.

In a sixteenth embodiment, there is provided a dsRNA molecule of from about 10 to about 30 nucleotides that inhibits replication of HCV, wherein said dsRNA contains at least one pyrimidine in the siRNA which is modified to include a 2'-Fluorine.

In a seventeenth embodiment, there is provided a dsRNA molecule of from about 10 to about 30 nucleotides that inhibits replication of HCV, wherein all of the pyrimidines in the dsRNA are modified to include a 2'-Fluorine.

In an eighteenth embodiment, there is provided a dsRNA molecule of from about 10 to about 30 nucleotides that inhibits replication of HCV, wherein all of the pyrimidines in the dsRNA are modified to include a 2'-Fluorine and wherein the 2'-Fluorine dsRNA is further modified to include a two base deoxynucleotide "TT" sequence at the 3' end of the dsRNA.

In a nineteenth embodiment there is provided a method of inducing targeted RNA interference toward HCV in hepatic cells, comprising administering the dsRNA molecule of sixteenth embodiment to hepatic cells and wherein the nucleotide sequence of said dsRNA molecule corresponds to an HCV nucleotide sequence.

In a twentieth embodiment, there is provided a vector comprising a DNA segment encoding the dsRNA molecule of the sixteenth embodiment.

In a twenty first embodiment, there is provided a vector comprising a DNA segment encoding the dsRNA molecule of the sixteenth embodiment wherein the sense strand of said double-stranded RNA molecule is operably linked to a first promoter and wherein the antisense strand of said double-stranded RNA molecule of is operably linked to a second promoter.

In a twenty second embodiment, there is provided a host cell comprising the vector of the twentieth embodiment.

In a twenty third embodiment, the invention provides a method for the delivery of siRNA to hepatocytes in an animal for therapeutic purposes, including inactivating a virus in the animal. The method comprises administering a cholesterol-lowering drug to an animal in conjunction with the administration of a dsRNA or siRNA that is modified to further comprise a cholesterol as a receptor-binding ligand (cholesterol-siRNA). The cholesterol-lowering drug can be administered prior to, at the same time, or subsequent to the administration of the cholesterol-labeled siRNA. In one preferred embodiment, the cholesterol lowering drug is a statin.

BRIEF DESCRIPTION OF THE DRAWINGS

FIG. 1 depicts the sequence and secondary structure of the 5' UTR from the HCV genome (SEQ ID NO: 2). It also provides specific sequences of siRNAs for inducing RNAi toward HCV in hepatic cells (SEQ ID NOs: 3 to 10, respectively in order of appearance).

FIG. 2 provides sequences for several HCV-specific siRNAs that are useful for inducing RNAi toward HCV in hepatic cells. Each HCV-specific siRNA is identified by the designation provided in the first column. The sequences shown in the column with the header "SEQUENCE (NN-N19-NN)" are SEQ ID NOS: 11 to 29, and the sequences shown in the right-most column are SEQ ID NOS: 30 to 67, respectively in order of appearance.

FIG. 3 shows the nucleotide sequence of the SARS coronavirus (SEQ ID NO: 1).

FIG. 5 depicts a subgenomic HCV replicon contained in the hepatoma cell line Huh 7, which was used to test the efficacy of siRNA in human liver cells.

FIG. 6 depicts the dose response of normalized luciferase activity in Huh-7 cells containing the subgenomic HCV replicon (5-2 line), that were administered different concentrations of siRNA5. Luciferase activity, which was measured at 1, 2 and 3 days post-transfection, fell with increasing doses of siRNA. The luciferase assay was performed using a Luciferase assay system available from Promega Corp. (Madison, Wis.), according to the manufacturer's instructions.

FIG. 7 depicts the sequence specificity of siRNA5 for inducing HCV-directed RNAi in Huh-7 liver cells.

FIG. 8 demonstrates that siRNA5 is not toxic to Huh-7 cells. ATPase levels were assayed using an ATPase assay kit available from Promega Corp. (Madison, Wis.), according to the manufacturer's instructions.

FIG. 9 depicts the effects of siRNA5 on HCV replication in 21-5 cells (Huh-7 cells containing full-length HCV), as measured by RNA assay. RNA levels were assayed using a TAQMAN RNA kit (F. Hoffman La-Roche, Switzerland), according to the manufacturer's instructions. Values are normalized.

Figure 14:
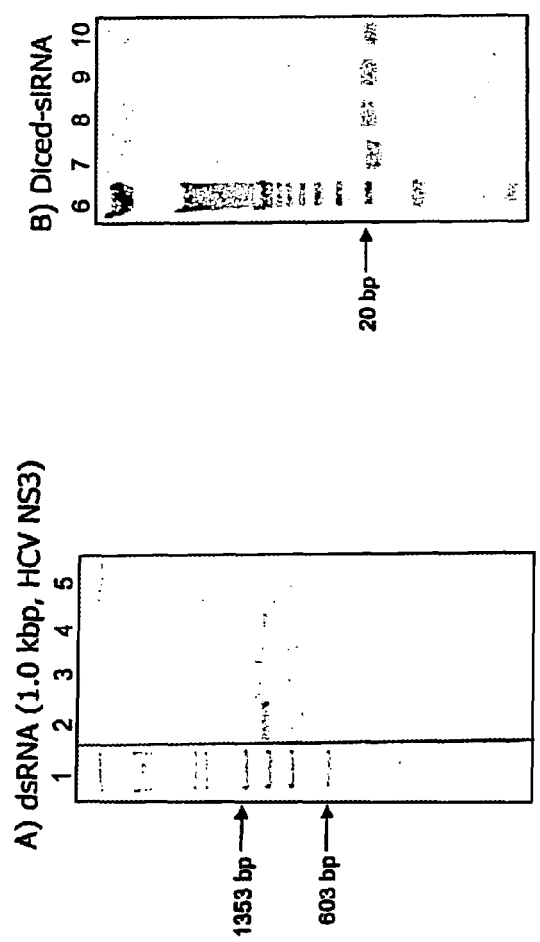

FIG. 14 demonstrates the use of recombinant human dicer to convert fluorinated dsRNA into 2'F-siRNA. The composition of the lanes is as follows: Lane 1: size marker, λ\HindIII+ φX174\HaeIII; Lane 2: ribo/ribo homoduplex RNA; Lane 3: ribo/2'-F heteroduplex RNA; Lane 4: 2'-F/ribo heteroduplex RNA; Lane 6: size marker, 10 bp DNA ladder; Lane 7: ribo/ribo homoduplex siRNA; Lane 8: ribo/2'-F heteroduplex siRNA; Lane 9: 2'-F/ribo heteroduplex siRNA; Lane 10: 2'-F/2'-F homoduplex siRNA.

Figure 15:
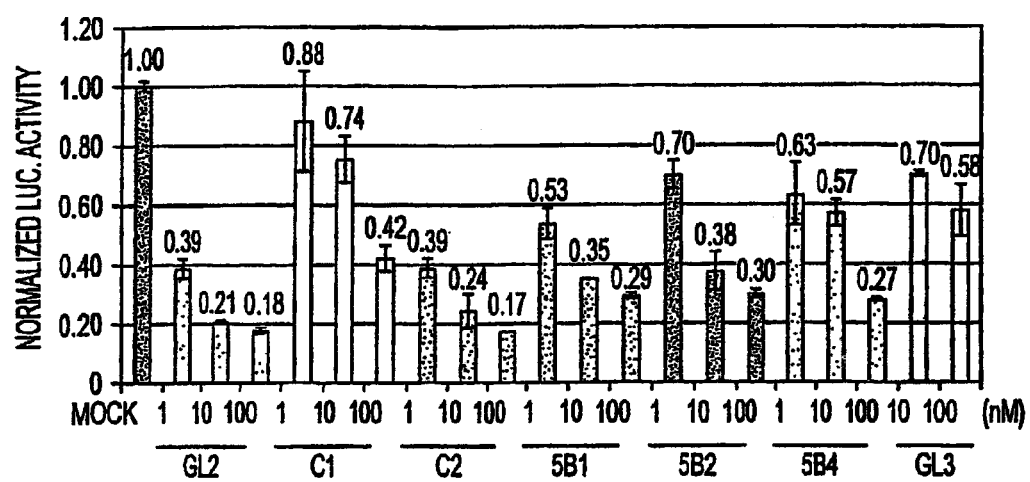

FIG. 15 shows a dose response of normalized luciferase activity in Huh-7 cells containing the subgenomic HCV replicon (5-2 line) to HCV-specific siRNAs. Luciferase activity fell with increasing doses of each siRNA.

Figure 16:
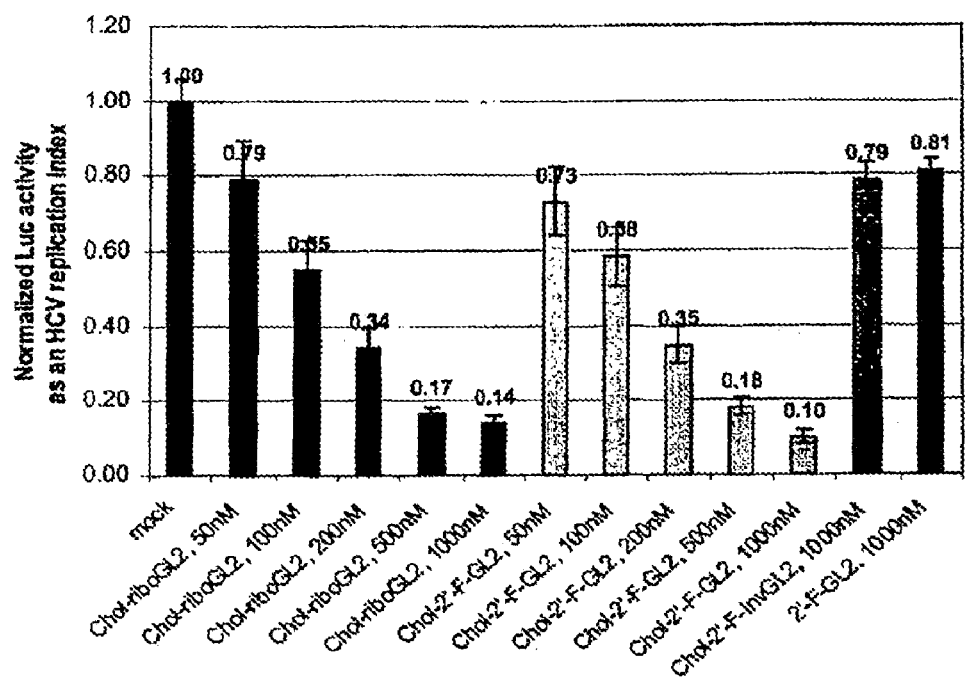

FIG. 16 shows that cholesterol shows a dose response of normalized luciferase activity in Huh-7 cells containing the subgenomic HCV replicon (5-2 line) to cholesterol-modified GL2 siRNA.

FIG. 17 demonstrates the increased stability seen with an siRNA that has been modified to include 2-Fluoro pyrimidines replacing all of the pyrimidines (2-F-siRNA) and 2-Fluoro pyrimidines replacing all of the pyrimidines and also a two base deoxynucleotide "TT" sequence added to the 3' ends of the molecule in place of the ribolucleotide "UU" overhangs present in 2-F-siRNA (2'-F-siRNA 3'-X).

Figure 18:
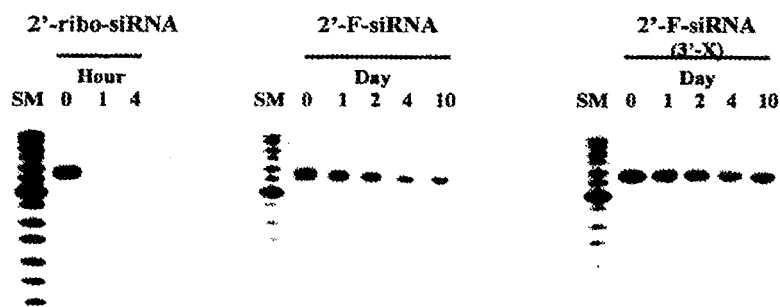

FIG. 18 shows that siRNA stability can be dramatically increased by fluorination within 2'-sugar.

Figure 19:
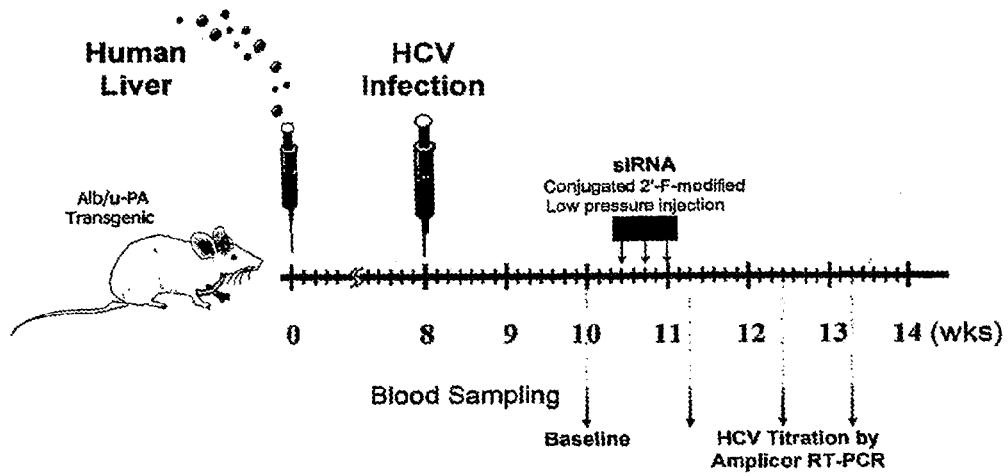

FIG. 19 shows evaluation of siRNA in vivo.

Figure 20:
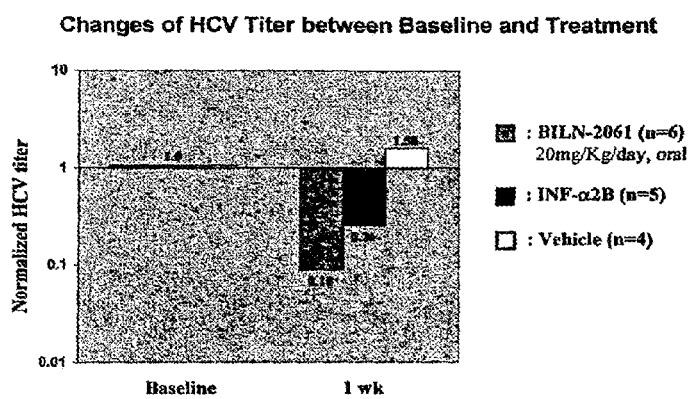

FIG. 20 shows conjugated 2'-F-siRNA is efficacious in chimeric mice by low pressure IV injection.

Figure 21:
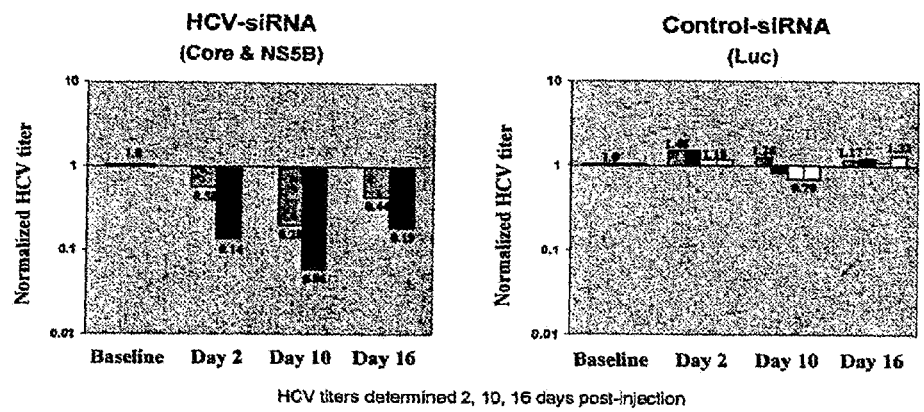

FIG. 21 shows conjugated 2'-F-siRNA given subcutaneously is partically effective in chimeric mice.

DETAILED DESCRIPTION OF THE INVENTION

The present invention provides dsRNA molecules that are about 10 to about 30 nucleotides long, and that mediate RNA interference in target cells. Preferably, the inventive molecules are chemically modified to confer increased stability against nuclease degradation, but retain the ability to bind to target nucleic acids.

As used herein, "RNA interference" (RNAi) refers to sequence-specific or gene specific suppression of gene expression (protein synthesis) that is mediated by siRNA, without generalized suppression of protein synthesis. While the invention is not limited to a particular theory or mode of action, RNAi may involve degradation of messenger RNA (mRNA) by an RNA-induced silencing complex (RISC), preventing translation of the transcribed mRNA. Alternatively, it may involve methylation of genomic DNA, which shunts transcription of a gene. The suppression of gene expression caused by RNAi may be transient or it may be more stable, even permanent.

"Gene suppression", "targeted suppression", "sequence-specific suppression", "targeted RNAi" and "sequence-specific RNAi" are used interchangeably herein. Furthermore, sequence-specific suppression, as used herein, is determined by separately assaying levels of the protein targeted for suppression in cells containing the siRNA (experimental cells) and in cells not containing the identical siRNA (control cells), then comparing the two values. Experimental and control cells should be derived from the same source and same animal. Also, control and experimental cells used in determining the level or quantity of gene suppression should be assayed under similar, if not identical, conditions.

RNA is a polymer of ribonucleotides, each containing the sugar ribose in association with a phosphate group and a nitrogenous base (typically, adenine, guanine, cytosine, or uracil). Like its cousin, DNA, RNA can form complementary hydrogen bonds. Therefore, RNA may be double-stranded (dsRNA), single-stranded (ssRNA) or double-stranded with a single-stranded overhang. Common types of RNA include messenger RNA (mRNA), transfer RNA (tRNA), ribosomal RNA (rRNA), short interfering RNA (siRNA), micro RNA (miRNA) and small hairpin RNA (shRNA), each of which plays a specific role in biological cells. As used herein, the term "RNA" includes all of these.

"Small interfering RNA" (siRNA) refers to double-stranded RNA molecules from about 10 to about 30 nucleotides long that are named for their ability to specifically interfere with protein expression. Preferably, siRNA molecules are 12-28 nucleotides long, more preferably 15-25 nucleotides long, still more preferably 19-23 nucleotides long and most preferably 21-23 nucleotides long. Therefore, preferred siRNA molecules are 12, 13, 14, 15, 16, 17, 18, 19, 20, 21, 22, 23, 24, 25, 26, 27 28 or 29 nucleotides in length.

The length of one strand designates the length of an siRNA molecule. For instance, an siRNA that is described as 21 ribonucleotides long (a 21-mer) could comprise two opposite strands of RNA that anneal together for 19 contiguous base pairings. The two remaining ribonucleotides on each strand would form an "overhang." When an siRNA contains two strands of different lengths, the longer of the strands designates the length of the siRNA. For instance, a dsRNA containing one strand that is 21 nucleotides long and a second strand that is 20 nucleotides long, constitutes a 21-mer.

siRNAs that comprise an overhang are desirable. The overhang may be at the 5' or the 3' end of a strand. Preferably, it is at the 3' end of the RNA strand. The length of an overhang may vary, but preferably is about 1 to about 5 bases, and more preferably is about 2 nucleotides long. Preferably, the siRNA of the present invention will comprise a 3' overhang of about 2 to 4 bases. More preferably, the 3' overhang is 2 ribonucleotides long. Even more preferably, the 2 ribonucleotides comprising the 3' overhang are uridine (U).

siRNAs of the present invention are designed to interact with a target ribonucleotide sequence, meaning they complement a target sequence sufficiently to bind to the target sequence. Preferably the target ribonucleotide sequence derives from a disease producing agent or pathogen. More preferably, the target ribonucleotide sequence is in a virus genome of an RNA virus or a DNA virus. Even more preferably, the virus is selected from the group consisting of hepatitis C virus (HCV), hepatitis A virus, hepatitis B virus, hepatitis D virus, hepatitis E virus, Ebola virus, influenza virus, rotavirus, reovirus, retrovirus, poliovirus, human papilloma virus (HPV), metapneumovirus and coronavirus.

Hepatitis C virus (HCV) is a highly preferred virus target. FIG. 1 and FIG. 2 disclose the nucleic acid sequences for several HCV-specific siRNA molecules. Among those shown, siRNA5, siRNAC1, siRNAC2, siRNA5B1, siRNA5B2, and siRNA5B4 have shown particularly good activity, and therefore are highly preferred. siRNAs at least 80%, 90%, or 95%, identical to these highly preferred siRNAs also constitute part of the invention.

Another preferred virus target is the coronavirus, which is associated with upper respiratory infections in humans and recently has been linked with SARS (severe acute respiratory syndrome). Coronavirus has the largest known RNA virus genome, 32 kilobases long, and its genome is composed of positively stranded RNA. (See FIG. 5) Each coronavirus mRNA has a 5'-end leader sequence of 60 to 80 nucleotides that is identical to the 5'-UTR of genomic RNA approximately 200 nucleotides long. (See FIG. 6) These sequences are highly conserved, and therefore, provide an excellent source of target sequences for which siRNAs. See *Fundamental Virology*, 3$^{rd}$ Ed., Chapter 18, p. 541-560 (Eds. Fields, Knipe and Howley), Lippincott-Raven (1995). In one embodiment, the entire leader sequence (nucleotides 1-72) is targeted. In another embodiment, one or more sections of the leader sequence is targeted. In a preferred embodiment, nucleotides 64-72 (TAAACGAAC) of the leader sequence are targeted. siRNA targeted to the coronavirus may be modified or unmodified.

In one embodiment, the invention provides an siRNA molecule comprising a ribonucleotide sequence at least 80% identical to a ribonucleotide sequence from a target agent or virus. Preferably, the siRNA molecule is at least 90%, 95%, 96%, 97%, 98%, 99% or 100% identical to the ribonucleotide sequence of the target agent or virus. The target can be the entire viral genome, a primary transcript, an open reading frame, or any portion of these. Most preferably, an siRNA will be 100% identical to the nucleotide sequence of a target agent or virus. However, siRNA molecules with insertions, deletions or single point mutations relative to a target may also be effective. Tools to assist siRNA design are readily available to the public. For example, a computer-based siRNA design tool is available on the internet at www.dharmacon.com.

By way of example, a polynucleotide having a nucleotide sequence at least 95% "identical" to a reference nucleotide sequence means that the polynucleotide's sequence may include up to five point mutations per 100 nucleotides of the reference nucleotide sequence, or 1 point mutation per 20 nucleotides. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97% 98%, 99% or 100% identical to the ribonucleotide sequence of a target agent or virus can be determined conventionally using known computer programs such as the Bestfit program (Wisconsin Sequence Analysis Package, Version 8 for Unix, Genetics Computer Group, Madison, Wis.). Bestfit uses the local homology algorithm of Smith and Waterman (Advances in Applied Mathematics 2:482-489 (1981)) to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference ribonucleotide sequence and that gaps in homology of up to 5% of the total number of ribonucleotides in the reference sequence are allowed.

The present invention also includes siRNA molecules that have been chemically modified to confer increased stability against nuclease degradation, but retain the ability to bind to target nucleic acids that may be present in cells. In the case where a target RNA is virus-specific, the modified siRNAs are able to bind to the virus specific RNAs or DNAs, thereby inactivating the virus.

A modified siRNA of the present invention comprises a modified ribonucleotide, and is resistant to enzymatic degradation, such as RNase degradation, yet retains the ability to inhibit viral replication in a cell containing the specific viral target RNA or DNA sequences. The siRNA may be modified at any position of the molecule so long as the modified siRNA binds to a target sequence and is resistant to enzymatic degradation. Modifications in the siRNA may be in the nucleotide base, i.e., the purine or the pyrimidine, the ribose or the phosphate. Preferably, the modification occurs at the 2' position of at least one ribose in an siRNA.

More specifically, the siRNA is modified in at least one pyrimidine, at least one purine or a combination thereof. However, generally all pyrimidines (cytosine or uracil), or all purines (adenosine or guanine) or a combination of all pyrimidines and all purines of the siRNA are modified. More preferably, the pyrimidines are modified, and these pyrimidines are cytosine, a derivative of cytosine, uracil, a derivative of uracil or a combination thereof. Ribonucleotides on either one or both strands of the siRNA may be modified.

Ribonucleotides containing pyrimidine bases found in RNA (cytidine and uridine) can be chemically modified by adding any molecule that inhibits RNA degradation or breakdown of the base, the ribose or the phosphates. As previously noted, the 2' position of ribose is a preferred site for modification. 2' modified siRNAs have a longer serum half-life and are resistant to degradation, relative to unmodified siRNAs or single-stranded RNAs, such as antisense or ribozyme. 2'-modified pyrimidine ribonucleotides can be formed by a number of different methods known in the art.

A preferable chemical modification is the addition of a molecule from the halide chemical group to a ribonucleotide of siRNA. Within the halides, fluorine is a preferred molecule. Besides fluoro-, other chemical moieties such as methyl-, methoxyethyl- and propyl- may be added as modifications. The most preferred modification, though, is fluoro-modification, such as a 2'-fluoro-modification or a 2',2'-fluoro-modification.

Thus, in a preferred embodiment of the invention, siRNA is modified by the addition of a fluorine molecule to the 2' carbon of a pyrimidine ribonucleotide. The siRNA may be fluorinated completely or partially. For example, only the cytosine ribonucleotides may be fluorinated. Alternatively, only the uracil ribonucleotides may be fluorinated. In a preferred embodiment, both uracil and cytosine are fluorinated. Only one strand, either sense or antisense, of siRNA may to be fluorinated. Even partial 2' fluorination of siRNA gives protection against nucleolytic degradation. Importantly, 2' fluorinated siRNA is not toxic to cells, an unexpected result given that fluorine chemistry usually is toxic to living organisms.

In addition, modified siRNAs of the present invention may contain chemical modifications that inhibit viral RNA polymerases. For example, siRNAs may comprise one or more nucleosides that inhibit viral RNA-dependent RNA polymerases. Examples of such nucleosides and other chemical modifications exist in WO 02/057425, WO 02/057287, WO 02/18404, WO 02/100415, WO 02/32920, WO 01/90121, U.S. Pat. No. 6,063,628 and US published application No. 2002/0019363.

siRNA can be prepared in a number of ways, such as by chemical synthesis, T7 polymerase transcription, or by treating long double stranded RNA (dsRNA) prepared by one of the two previous methods with Dicer enzyme. Dicer enzyme creates mixed populations of dsRNA from about 21 to about 23 base pairs in length from dsRNA that is about 500 base pairs to about 1000 base pairs in size. Unexpectedly, Dicer can effectively cleave modified strands of dsRNA, such as 2' fluoro-modified dsRNA. Before development of this method, it was previously thought that Dicer would not be able to cleave modified siRNA. The Dicer method of preparing siRNAs can be performed using a Dicer siRNA Generation Kit available from Gene Therapy Systems (San Diego, Calif.).

The invention particularly includes a method of making a modified siRNA that targets a nucleic acid sequence in a virus, comprising (a) preparing a modified-double stranded RNA (dsRNA) fragment containing at least one modified ribonucleotide in at least one strand, and (b) cleaving the modified-dsRNA fragments with recombinant human Dicer, resulting in more than one modified siRNA. The method may further comprise (c) isolating the modified siRNAs.

In the methods for making siRNA, a dsRNA fragment can be prepared by chemical synthesis or in vitro translation. In one embodiment, the modified siRNA is a 2' modified siRNA in which the modification is at the 2' position of at least one ribonucleotide of said siRNA. The modification is selected from the group consisting of fluoro-, methyl-, methoxyethyl and propyl-modification. Preferably the fluoro-modification is a 2'-fluoro-modification or a 2',2'-fluoro-modification. The pyrimidines, the purines or a combination thereof of the siRNA are modified. More preferably, the pyrimidines are modified, such as cytosine, a derivative of cytosine, uracil, a derivative of uracil or a combination thereof. One or both strands of the siRNA may contain one or more modified ribonucleotide.

The invention further provides a method of inactivating a target agent or virus in a patient by administering to the patient a dsRNA in an effective amount to inactivate the targeted agent or virus. Preferably the dsRNA is modified as described above. RNA interference toward a targeted DNA segment in a cell can be achieved by administering a double-stranded RNA molecule to the cells, wherein the ribonucleotide sequence of the double-stranded RNA molecule corresponds to the ribonucleotide sequence of the targeted DNA segment. Preferably, the dsRNA used to induce targeted RNAi is siRNA.

As used herein "targeted DNA segment" is used to mean a DNA sequence encoding, in whole or in part, an mRNA for a targeted protein, including introns or exons, where suppression is desired. DNA segment can also mean a DNA sequence that normally regulates expression of the targeted protein, including but not limited to the promoter of the targeted protein. Furthermore, the DNA segment may or may not be a part of the cell's genome or it may be extrachromosomal, such as plasmid DNA.

The present invention is particularly directed to a method of inactivating a virus in a patient by administering to the patient an siRNA, preferably a modified siRNA, in an effective amount to inactivate the virus. The siRNA is preferably about 10 to about 30 ribonucleotides in length, more preferably 12-28 ribonucleotides, more preferably 15-25 ribonucleotides, even more preferably 19-23 ribonucleotides and most preferably 21-23 ribonucleotides.

Also, the method of inactivating a virus preferably utilizes an siRNA that is modified at the 2' position of at least one ribonucleotide of said siRNA. The siRNA may be modified with chemical groups selected from the group consisting of fluoro-, methyl-, methoxyethyl- and propyl-. Fluoro-modification is most preferred, and either a 2'-fluoro-modification or a 2',2'-fluoro-modification is useful in the method. The modification may be at a pyrimidine, a purine or a combination thereof of the siRNA. More preferably the pyrimidines are modified, such as cytosine, a derivative of cytosine, uracil, a derivative of uracil or a combination thereof. In one embodiment, one strand of the siRNA contains at least one modified ribonucleotide, while in another embodiment, both strands of the siRNA contain at least one modified ribonucleotide.

siRNAs useful in treatment methods may also be modified by the attachment of at least one, but preferably more than one, receptor-binding ligand(s) to the siRNA. Such ligands are useful to direct delivery of siRNA to a target virus in a body system, organ, tissue or cells of a patient, such as the liver, gastrointestinal tract, respiratory tract, the cervix or the skin.

In preferred embodiments, receptor-binding ligands are attached to either a 5'-end or a 3'-end of an siRNA molecule. Receptor-binding ligands may be attached to one or more siRNA ends, including any combination of 5'- and 3'-ends. Thus, when receptor binding ligands are attached only to the ends of an siRNA molecule, anywhere between 1 and 4 such ligands may be attached.

The selection of an appropriate ligand for targeting siRNAs to viruses in particular body systems, organs, tissues or cells is considered to be within the ordinary skill of the art. For example, to target an siRNA to hepatocytes, cholesterol may be attached at one or more ends, including any combination of 5'- and 3'-ends, of an siRNA molecule. The resultant cholesterol-siRNA is delivered to hepatocytes in the liver, thereby providing a means to deliver siRNAs to this targeted location. Other ligands useful for targeting siRNAs to the liver include HBV surface antigen and low-density lipoprotein (LDL).

As another example, siRNA molecules that target Human Immunodeficiency virus type 1 (HIV-1) can be delivered to T lymphocytes where the target nucleic acids are located (Song, E. et al., *J. of Virology*, 77(13): 7174-7181 (2003)). This delivery can be accomplished by attaching, at the 3'-end or 5'-end of siRNA molecules, HIV-1 surface antigen capable of binding to the CD4 surface protein located on T-cells (Kilby, M. et al., *New England J. of Medicine*, 348(22): 2228-38 (2003)).

Similarly, siRNA molecules that target Influenza A virus can be delivered to epithelial cells of the respiratory tract where the target nucleic acids are located (Ge, Q. et al., *Proc. Natl. Acad. of Sciences*, 100(5): 2718-2723 (2002)). This delivery can be accomplished by attaching, at the 3'-end or 5'-end of siRNA molecules, the Influenza virus surface antigen, which is capable of binding to the sialic acid residues located on the surface of the epithelial cells (Ohuchi, M., et al., *J. of Virology*, 76(24): 12405-12413 (2002); Glick, G. et al., *J. of Biol. Chem.*, 266 (35): 23660-23669 (1991)).

Also, siRNA molecules that target respiratory syncitial virus (RSV) can be delivered to epithelial cells of the respiratory tract where the target nucleic acids are located (Bitko, V. et al., *BMC Microbiology*, 1:34 (2001)). This delivery can be accomplished by attaching, at the 3'-end or 5'-end of siRNA molecules, RSV surface antigen (Malhotra, R. et al., *Microbes and Infection*, 5: 123-133 (2003)).

As still another example, siRNAs that target Human Papillomavirus (HPV) can be delivered to basal epithelial cells where the target nucleic acids are located (Hall, A. et al., *J. of Virology*, 77(10): 6066-6069 (2003)). This delivery can be accomplished by attaching, at the 3'-end or 5'-end of siRNA molecules, HPV surface antigen capable of binding to heparin sulfate proteoglycans located on the surface of basal epithelial cells (Bousarghin L. et al., *J. of Virology*, 77(6): 3846-3850 (2002)).

Further, siRNAs that target Poliovirus (PV) can be delivered to cells of the nervous system where the target nucleic acids are located (Gitlin, L. et al., Nature, 418: 430-434 (2002)). This delivery can be accomplished by attaching, at the 3'-end or 5'-end of siRNA molecules, PV surface antigen capable of binding to the CD155 receptor located on the surface of neurons (He, Y. et al., Proc. Natl. Acad. of Sciences, 97 (1): 79-84 (2000)).

As noted, the methods of treatment are intended to target disease-causing agents or pathogens, and more particularly viruses, which can be either RNA viruses or DNA viruses. Preferred viruses are selected from the group consisting of hepatitis C virus (HCV), hepatitis A virus, hepatitis B virus, hepatitis D virus, hepatitis E virus, Ebola virus, influenza virus, rotavirus, reovirus, retrovirus, poliovirus, human papilloma virus (HPV), metapneumovirus and coronavirus. More preferably the target virus is hepatitis C virus or a coronavirus.

In one aspect, the method utilizes an siRNA prepared by (a) identifying a target ribonucleotide sequence in a virus genome for designing a small interfering RNA (siRNA) and (b) producing a siRNA that has been modified to contain at least one modified ribonucleotide. Preferably, the siRNA comprises a double-stranded RNA molecule with a first strand ribonucleotide sequence corresponding to a ribonucleotide sequence corresponding to a target ribonucleotide sequence in the virus, and a second strand comprising a ribonucleotide sequence complementary to the target ribonucleotide sequence. The first and second strands should be separate complementary strands that hybridize to each other to form a double-stranded RNA molecule. Moreover, one or both of the strands should comprise at least one modified ribonucleotide.

In preferred embodiments of the invention, the siRNA targets a ribonucleotide sequence in the hepatitis C virus genome. The target ribonucleotide sequence comprises a conserved ribonucleotide sequence necessary for HCV replication, and the conserved ribonucleotide sequence is selected from the group consisting of 5'-untranslated region (5'-UTR), 3'-untranslated region (3'-UTR), core, and NS3 helicase. Highly preferred siRNA molecules comprise a sequence at least 80% identical to those of siRNA5, siRNAC1, siRNAC2, siRNA5B1, siRNA5B2, or siRNA5B4. The siRNAs may be unmodified, or modified as described above.

Methods of inhibiting the replication of HCV in cells positive for HCV should not be toxic to the cells, or cause apoptosis in the treated cells. Preferably, the inhibition of HCV replication is specifically tailored to affect only HCV replication in the cells, such that normal growth, division or metabolism is not affected. Cells in which HCV has been shown to replicate include, but are not limited to hepatic cells, B cell lymphocytes and T cell lymphocytes. Preferably, a method of inhibiting the replication of HCV is performed in hepatic cells.

According to the invention, "hepatic cells" can be from any animal source. Further, the hepatic cells may be in cell culture, or part of a tissue, or an organ, in part or in whole. The phrase hepatic cells is meant to include any cell constituting a normal, abnormal or diseased liver cell. Examples of hepatic cells include, but are not limited to, Kupffer cells, hepatocytes and cells comprising a hepatocellular carcinoma. "Hepatic cells" is not meant to include cells that make up discrete structures within the liver, such as endothelial cells lining blood vessels. A tissue or organ containing the hepatic cells may be within a subject or may be biopsied or removed from the animal. Additionally, the tissue may be "fresh" in that the tissue would be recently removed from a subject, without any preservation steps between the excision and the methods of the current invention. Prior to application of the methods of the current invention, the tissue may also have been preserved by such standard tissue preparation techniques including, but not limited to, freezing, quick freezing, paraffin embedding and tissue fixation. Furthermore, the tissue may also be a xenograft or a syngraft on or in another host animal. As used herein, the terms animal and subject are used interchangeably.

According to the invention, "hepatitis C virus," or "HCV," takes its ordinary meaning in the art as of the date of invention. The hepatitis C virus is an RNA virus of the Flaviviridae family. For example as used herein, HCV includes, but is not limited to genotypes 1-11 (using the most common genotyping system), with these genotypes being broken down into sub-types, some of which include but are not limited to 1a, 1b, 1c, 2a, 2b, 2c, 3a, 3b, 4a, 4b, 4c, 4d, 4e, 5a, 6a, 7a, 7b, 8a, 8b, 9a, 10a and 11a. Further, isolates from individuals consist of closely related yet heterogeneous populations of viral genomes, sometimes referred to as quasispecies.

Pestivirus is yet another target of the present invention. As used herein, "pestivirus" takes its ordinary meaning in the art as of the date of invention. The pestivirus belongs to the family Flaviviridae. Pestivirus is widespread throughout the Australian cattle population. It is believed that about 70% of herds are actively infected with pestivirus. Infection of susceptible animals can cause a variety of diseases—some not apparent until well after the initial spread of the virus into a herd. Pestivirus is a genus of viruses that includes hog cholera virus, bovine viral diarrhea virus (BVDV) and border disease virus (BDV) or hairy-shaker disease virus.

siRNA may be administered to a patient by intravenous injection, subcutaneous injection, oral delivery, liposome delivery or intranasal delivery. The siRNA may then accumulate in a target body system, organ, tissue or cell type of the patient.

The present invention also provides a method of inhibiting the replication of a virus in mammalian cells, comprising transfecting cells harboring the virus with a vector that directs the expression of virus-specific siRNA. In one embodiment, the invention provides a method of inhibiting the replication of hepatitis C virus (HCV) in cells positive for HCV, comprising transfecting HCV-positive cells with a vector that directs the expression of an HCV-specific siRNA. The cells may be evaluated to determine if a marker in the cells has been inhibited by the siRNA.

Thus, the invention also provides vectors and host cells comprising a nucleic acid segment encoding the described siRNAs.

Vectors of the present invention may be employed for producing siRNAs by recombinant techniques. Thus, for example, a DNA segment encoding an siRNA may be included in any one of a variety of expression vectors for expressing any DNA sequence. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in a desired host.

The appropriate DNA segment may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA segment in the expression vector is operatively linked to an appropriate expression control sequence(s) (promoter) to direct siRNA synthesis. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter. Preferably the promoters of the present invention are from the type III class of RNA polymerase III promoters. More preferably, the promoters are selected from the group consisting of the U6 and H1 promoters. The U6 and H1 promoters are both members of the type III class of RNA polymerase II promoters. The promoters of the present invention may also be inducible, in that expression may be turned "on" or "off." For example, a tetracycline-regulatable system employing the U6 promoter may be used to control the production of siRNA. The expression vector may or may not contain a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or tetracycline or ampicillin resistance.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

In one embodiment, the invention provides a vector, wherein the DNA segment encoding the sense strand of the RNA polynucleotide is operably linked to a first promoter and where the DNA segment encoding the antisense (opposite) strand of the RNA polynucleotide molecule of is operably linked to a second promoter. In other words, each strand of the RNA polynucleotide is independently expressed. Furthermore, the promoter driving expression of each strand can be identical or each one may be different from the other promoter.

In another embodiment, the vector of the current invention may comprise opposing promoters. For example, the vector may comprise two U6 promoters on either side of the DNA segment encoding the sense strand of the RNA polynucleotide and placed in opposing orientations, with or without a transcription terminator placed between the two opposing promoters. The U6 opposing promoter construct is similar to the T7 opposing promoter construct as described in Wang, Z. et al., J. Biol. Chem. 275: 40174-40179 (2000). See Miyagishi, M. and Taira, K., Nature Biotech. 20: 497-500 (2002).

In another embodiment, the DNA segments encoding both strands of the RNA polynucleotide are under the control of a single promoter. In one embodiment, the DNA segments encoding each strand are arranged on the vector with a "loop" region interspersed between the two DNA segments, where transcription f the DNA segments and loop region creates one RNA transcript. The single transcript will, in turn, anneal to itself creating a "hairpin" RNA structure capable of inducing RNAi. The "loop" of the hairpin structure is preferably from about 4 to about 6 nucleotides in length. More preferably, the loop is 4 nucleotides in length.

The vector containing the appropriate DNA sequence as described herein, as well as an appropriate promoter or control sequence, may be employed to transform an appropriate host to permit the host to express the siRNA. Appropriate cloning and expression vectors for use with prokaryotic and eukaryotic hosts are described by Sambrook, et al., Molecular Cloning: A Laboratory Manual, Second Edition, Cold Spring Harbor, N.Y. (1989), the disclosure of which is hereby incorporated by reference.

Host cells are genetically engineered (transduced or transformed or transfected) with the vectors of this invention which may be, for example, cloning vectors or expression vectors. The vectors may be, for example, in the form of a plasmid, a viral particle, a phage, etc. The engineered host cells may be cultured in conventional nutrient media modified as appropriate for activating promoters, selecting transformants. The culture conditions, such as temperature, pH and the like, are those previously used with the host cell selected for expression, and will be apparent to the ordinarily skilled artisan.

In a further embodiment, the present invention relates to host cells containing the above-described constructs. A host cell may be a higher eukaryotic cell, such as a mammalian cell, or a lower eukaryotic cell, such as a yeast cell, or the host cell may be a prokaryotic cell, such as a bacterial cell. Preferably, host cells are mammalian cells. More preferably, host cells are hepatic cells. Introduction of a construct into host cells can be effected by calcium phosphate transfection, DEAE-Dextran mediated transfection, or electroporation (Davis, L., et al., Basic Methods in Molecular Biology (1986)).

The term patient, as used herein, refers to an animal, preferably a mammal. More preferably the patient can be a primate, including non-human and humans. The terms subject and patient are used interchangeably herein.

The treatments envisioned by the current invention can be used for subjects with a pre-existing viral infection, or for subjects pre-disposed to an infection. Additionally, the methods of the current invention can be used to correct or compensate for cellular or physiological abnormalities involved in conferring susceptibility to viral infections in patients, and/or to alleviate symptoms of a viral infections in patients, or as a preventative measure in patients.

The method of treating a patient having a viral infection involves administration of compositions to the subjects. As used herein, composition can mean a pure compound, agent or substance or a mixture of two or more compounds, agents or substances. As used herein, the term agent, substance or compound is intended to mean a protein, nucleic acid, carbohydrate, lipid, polymer or a small molecule, such as a drug.

In one embodiment of the current invention, the composition administered to the subject is a pharmaceutical composition. Further, the pharmaceutical composition can be administered orally, nasally, parenterally, intrasystemically, intraperitoneally, topically (as by drops or transdermal patch), bucally, or as an oral or nasal spray. Intranasal delivery of a virus that causes upper respiratory diseases, such as the coronavirus or the metapneumovirus, would be a particularly advantageous delivery mode. The term "parenteral," as used herein, refers to modes of administration that include intravenous, intramuscular, intraperitoneal, intrasternal, subcutaneous and intraarticular injection and infusion. The pharmaceutical compositions as contemplated by the current invention may also include a pharmaceutically acceptable carrier.

"Pharmaceutically acceptable carrier" includes, but is not limited to, a non-toxic solid, semisolid or liquid filler, diluent, encapsulating material or formulation auxiliary of any type, such as liposomes.

A pharmaceutical composition of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention can also contain adjuvants such as, but not limited to, preservatives, wetting agents, emulsifying agents, and dispersing agents. Prevention of the action of microorganisms can be ensured by the inclusion of various antibacterial and antifungal agents, for example, paraben, chlorobutanol, phenol, sorb acid, and the like. It can also be desirable to include isotonic agents such as sugars, sodium chloride, and the like. Prolonged absorption of the injectable pharmaceutical form can be brought about by the inclusion of agents which delay absorption such as aluminum monostearate and gelatin.

In some cases, to prolong the effect of the drugs, it is desirable to slow the absorption from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include, but are not limited to, capsules, tablets, pills, powders, and granules. In such solid dosage forms, the active compounds are mixed with at least one item pharmaceutically acceptable excipient or carrier such as sodium citrate or dicalcium phosphate and/ or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include, but are not limited to, pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Alternatively, the composition can be pressurized and contain a compressed gas, such as nitrogen or a liquefied gas propellant. The liquefied propellant medium and indeed the total composition is preferably such that the active ingredients do not dissolve therein to any substantial extent. The pressurized composition can also contain a surface active agent. The surface active agent can be a liquid or solid nonionic surface active agent or can be a solid anionic surface active agent. It is preferred to use the solid anionic surface active agent in the form of a sodium salt.

The compositions of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the invention, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., *Meth. Cell Biol.* 14:33 et seq (1976)).

One of ordinary skill in the art will appreciate that effective amounts of the agents of the invention can be determined empirically and can be employed in pure form or, where such forms exist, in pharmaceutically acceptable salt, ester or prodrug form. A "therapeutically effective" amount of the inventive compositions can be determined by prevention or amelioration of adverse conditions or symptoms of diseases, injuries or disorders being treated. The agents can be administered to a subject, in need of treatment of viral infection, as pharmaceutical compositions in combination with one or more pharmaceutically acceptable excipients. It will be understood that, when administered to a human patient, the total daily usage of the agents or composition of the present invention will be decided by the attending physician within the scope of sound medical judgement. The specific therapeutically effective dose level for any particular patient will depend upon a variety of factors: the type and degree of the cellular or physiological response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

Dosing also can be arranged in a patient specific manner to provide a predetermined concentration of the agents in the blood, as determined by techniques accepted and routine in the art. Thus patient dosaging can be adjusted to achieve regular on-going blood levels, as measured by HPLC, on the order of from 50 to 1000 ng/ml.

Various medications can lower blood cholesterol levels. These medications or drugs include e.g., statins, resins and nicotinic acid (niacin), gemfibrozil and clofibrate. Clofibrate (Atromid-S) raises the HDL cholesterol levels and lowers triglyceride levels. Gemfibrozil (Lopid) lowers blood fats and raises HDL cholesterol levels. Nicotinic Acid works in the liver and is used to lower triglycerides and LDL cholesterol, and raise HDL ("good") cholesterol. Resins promote increased disposal of cholesterol. Medications in this class include: Cholestryamine (Questran, Prevalite, Lo-Cholest); Colestipol (Colestid); and Coleseveiam (WelChol).

Statin drugs are very effective for lowering LDL ("bad") cholesterol levels, have few immediate short-term side effects and are a preferred cholesterol lowering drug for use in the methods of the present invention. The statins include: Atorvastatin (Lipitor); Fluvastatin (Lescol); Lovastatin (Mevacor); Pravastatin (Pravachol); Rosuvastatin Calcium (Crestor); and Simvastatin (Zocor). (See also "Cholesterol lowering with statin drugs, risk of stroke, and total mortality. An overview of randomized trials"; Hebert P R, Gaziano J M, Chan K S, Hennekens C H. JAMA (1997) Nov. 26; 278(20):1660-1.

HMG-CoA (3-hydroxy-3-methylglutaryl-coenzyme A) reductase (HMGR) catalyzes the committed step in cholesterol biosynthesis. Statins are HMGR inhibitors with inhibition constant values in the nanomolar range that effectively lower serum cholesterol levels and are widely prescribed in the treatment of hypercholesterolemia. Statin drugs increase the expression of LDL receptors on the surface of liver hepatocytes. As a consequence of the increase in LDL receptor expression, the level of cholesterol is lowered in plasma. Thus, by administering a statin drug, the level of competing cholesterol in plasma is reduced and the level of LDL receptors for binding cholesterol-siRNA in the liver are increased. The invention thus provides a method for increased uptake of cholesterol labeled siRNA wherein the siRNA is administered in conjunction with a statin whereby the level of competing cholesterol in the serum is reduced, allowing for more efficient uptake of cholesterol labeled siRNA by hepatocytes. The statin can be administered before, with or after the administration of the cholesterol-siRNA.

It will be readily apparent to one of ordinary skill in the relevant arts that other suitable modifications and adaptations to the methods and applications described herein can be made without departing from the scope of the invention or any embodiment thereof.

EXAMPLES

The examples demonstrate that siRNA, including modified siRNA, can effectively inhibit viral replication in mammalian cells. Moreover, the examples show that the inventive siRNAs promote HCV RNA degradation in human liver cells and establish that hepatocytes possess the necessary functional components of modified siRNA-induced silencing. The examples also demonstrate that siRNA technology can be used as a therapy to inhibit HCV replication in host cells. The inventors, by submitting the following examples, do not intend to limit the scope of the claimed invention.

Example 1

To test whether siRNA directed to the HCV genome confers intracellular immunity against this human pathogen, a recently developed HCV cell culture systems in human hepatoma cell line, Huh-7, was used. One of the cell lines, 5-2, harbors autonomously replicating subgenomic HCV RNA (Bartenschlager, J. Virol, 2001). The subgenomic replicon carries firefly luciferase gene, allowing a reporter function assay as a measure of HCV RNA replication (FIG. 5). Owing to cell culture adaptive mutations introduced into the genome (Bart), these 5-2 cells replicate HCV RNA at levels of up to $5 \times 10^4$ virus particles/cell.

Using T7 transcription, several 21-bp siRNA duplexes against different regions of the 5'-UTR of the HCV genome were made (FIG. 5). Briefly, 2 oligo double-stranded DNA molecules comprising the T7 promoter and the 5' UTR of HCV being oriented in either the sense direction or the antisense direction were generated. Each oligo DNA was then transcribed in vitro to produce (+) and (−) RNA and then treated with DNAase I to remove the DNA template. The two RNA strands were allowed to anneal at 37° C. overnight, generating dsRNA. After treating the dsRNA with RNAase T1 to remove unreacted ssRNA species, the dsRNA was purified for transfection.

Several other siRNA duplexes were designed, including GL2 and GL3, that were directed against the fruit fly and sea pansy luciferase genes, respectively. Using standard transfection techniques, the siRNAs were transfected into the 5-2 cells and luciferase activity was measured to determine the effect of the siRNAs on HCV replication. Luciferase activity was measured 48 hours after transfection. In cells where siRNA5 was transfected, there was reduced luciferase activity of up to 85%, in a dose responsive manner (FIG. 6). The inhibition of luciferase activity was not seen in cells that were transfected with irrelevant siRNA (SIN). The sequence of SIN was taken from sindbis virus transcription promoter (FIG. 1).

Example 2

The sequence specificity of the siRNA5 response was further tested using additional siRNA duplexes, GL2 and GL3. FIG. 1 shows that GL2 and GL3 differ from each other by 3-nucleotides. Luciferase activity was reduced by 90% in cells transfected with siRNA5 or GL2, but no significant reduction was seen in cells transfected with GL3 (FIG. 7). The luciferase assay was performed using a Luciferase assay system available from Promega Corp. (Madison, Wis.), according to the manufacturer's instructions.

Example 3

Whether or not siRNA5 was toxic to transfected cells also was tested. Toxicity was by measured using an ATPase activity assay. FIG. 8 shows that the siRNA5-induced reduction in HCV replication, as seen in FIG. 6, was not due to cellular toxicity which is attributed to non sequence-specific RNAi. ATPase levels were assayed using an ATPase assay kit from Promega (Madison, Wis.) according to the manufacturer's instructions.

Example 4

The full-length HCV replicon may possess the ability to adapt and suppress RNAi, thus replicating in spite of the presence of siRNA, as documented in Li, H, Science 296: 1319-1321 (2002). To determine the effects of siRNA5 on replication of full-length HCV RNA in Huh-7 cells, from the 21-5 cell line, harboring the selectable full-length HCV replicon, were treated with siRNA5. Levels of HCV RNA were measured by quantitative PCR using TAQMAN (F. Hoffman La-Roche, Switzerland). The results as seen in FIG. 9 show that siRNA-directed silencing reduced steady-state viral RNA production, even in the setting of an adapted HCV mutant, where RNA replication was very high. Results from both subgenomic and full-length HCV replicons suggest that none of the HCV proteins can suppress RNA interference.

Example 5

Figure 10:
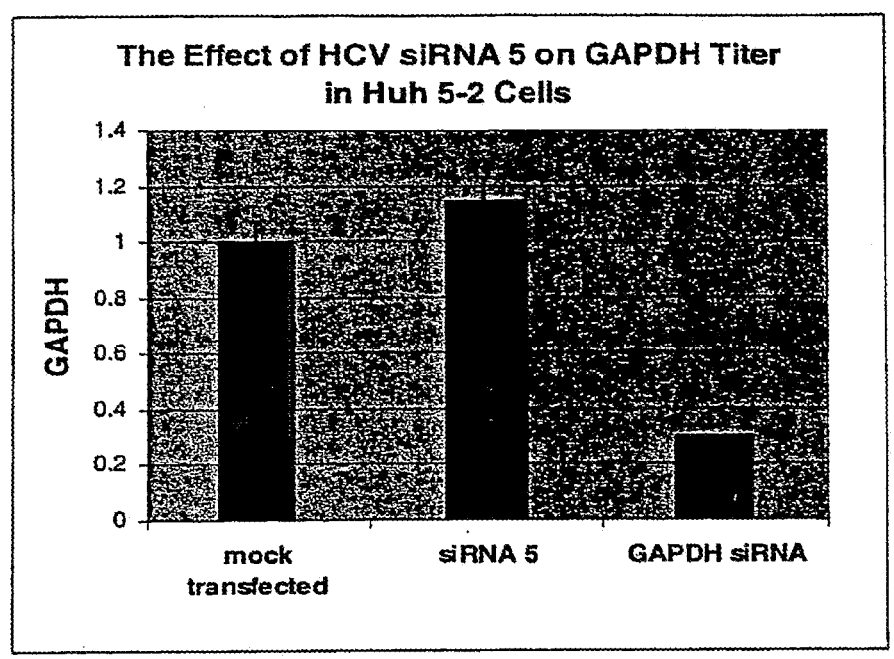
FIG. 10 demonstrates that siRNA5 does not affect the viability of Huh 5-2 cells. Specifically, mRNA encoding GAPDH, an enzyme essential to glycolysis was measured in Huh 5-2 cells transfected with siRNA5 or GAPDH-specific siRNA. The graph demonstrates that siRNA5 did not affect RNA levels of GAPDH. GAPDH was measured using a TAQMAN RNA kit (F. Hoffman La-Roche, Switzerland), according to the manufacturer's instructions. Values are normalized.

Whether or not siRNA5 was toxic to transfected cells also was tested. Specifically, mRNA encoding GAPDH, an enzyme essential in glycolysis, was measured in Huh 5-2 cells transfected with siRNA5, or siRNA specific towards the GAPDH sequence. FIG. 10 demonstrates that siRNA5 did not affect RNA levels of GAPDH. GAPDH was measured using a TAQMAN RNA kit (F. Hoffman La-Roche, Switzerland) according to the manufacturer's instructions.

Example 6

To test the effectiveness of siRNA5 on inhibiting the ability of HCV to replicate in an infected liver, portions of HCV-infected human liver are xenografted onto transgenic severe combined immunodeficient (SCID) mice according to methods well known to the skilled artisan.

Briefly, once the HCV-infected liver has supplanted the mouse liver, liposome-encapsulated siRNA5, or control liposomes are administered by intravenous injection to the mice through the tail vein, or another accessible vein. The mice are dosed one time a day for 3-10 days.

At the end of the dosing regimen the mice are sacrificed and blood collected and the livers removed. The liver is divided into portions such that a portion is frozen using liquid nitrogen, a portion is fixed for paraffin embedding, and a portion is fixed for sectioning onto slides.

Using the appropriate allotment, HCV RNA is quantified using the TAQMAN RNA assay kit previously utilized herein to determine the levels of HCV RNA in the liver cells. Further, anti-HCV antibody titers can be measured in the collected blood samples, along with serum ALT levels.

Example 7

To test the effectiveness of siRNA5 on inhibiting the ability of HCV to infect a healthy liver, portions of normal human liver are xenografted onto transgenic severe combined immunodeficient (SCID) mice according to methods well known to the skilled artisan.

Briefly, once the healthy liver has supplanted the mouse liver, liposome-encapsulated siRNA5, or control liposomes are administered by intravenous injection to the mice through the tail vein, or another accessible vein. The mice are dosed one time a day for 3-10 days. After the pre-dosing regimen, active HCV is then injected intravenously, or via hepatic injection, into the mice.

At about 6, 12, 18, 24 hours, and periodically up to about 5 days after the mice are infected with HCV, the mice are sacrificed and blood collected and the livers removed. The liver is divided into portions such that a portion is frozen using liquid nitrogen, a portion is fixed for paraffin embedding, and a portion is fixed for sectioning onto slides.

Using the appropriate allotment, HCV RNA is quantified using the TAQMAN RNA assay kit previously utilized herein to determine the levels of HCV RNA in the liver cells. Further, anti-HCV antibody titers can be measured in the collected blood samples, along with serum ALT levels.

Example 8

Modified siRNA can be prepared by chemical synthesis. In one embodiment, each C and U within a siRNA duplex, e.g. GL2, can be substituted with 2'-F-U and 2'F-C. To produce siRNA with 3'-end overhangs comprising 2'-F-U and 2'F-C, a universal support can be used. By selectively cleaving the oligo from the support, a practitioner can ensure that residues of the overhangs comprise modified nucleotides. Alternatively, the nucleotides comprising the 3'-end overhang can be unmodified dTdT.

2'-F RNA oligonucleotides can be synthesized on an Applied Biosystems 8909 or 8905 DNA/RNA synthesizer using the standard 1 μmol beta-cyanoethyl phosphoramidite RNA chemistry protocol. The RNA phosphoramidite monomers and columns of Pac-A, 2'-F-Ac-C, iPr-Pac-G, 2'-F-U, and U-RNA CPG can be obtained from Glen Research (Sterling, Va.). (See catalog nos. 10-3000-05, 10-3415-02, 10-3021-05, 10-3430-02, and 20-3430-41E, respectively.) Glen Research's Sulfurizing Reagent (catalog no. 404036-10) can be used as an oxidant to obtain a single phosphorothioate backbone between the 3' CPG and a subsequent base. To attain the coupling, the oxidizing step of the standard RNA 1 μmol protocol can be replaced with the standard thioate 1 μmol protocol. Cholesteryl-TEG phosphoramidite (Glen Research, catalog no. 10-1975-90) and cholestryl-TEG CPG (Glen Research, catalog no. 20-2975-41E) can be incorporated onto the 5' or 3' ends of one or more of the oliogoribonucleotides. After synthesis, the 2'-F RNA's are cleaved and deprotected with 1:1 ammonium hydroxide/methylamine, and the silyl groups are removed with triethylamine trihydrofluoride using standard protocols. See e.g. http://www.glenres.com/productfiles/technical/tb_rnadeprotection.pdf. The oligoribonucleotides are then desalted on Sephadex G25 columns (Pharmacia NAP 25, catalog no. 17-08252-02) with sterilized water and purified using standard gel electrophoresis protocols. Modified siRNAs also can be obtained from commercial vendors such as Dharmacon (Lafayette, Colo.).

Alternatively, modified siRNA can be prepared by transcription using the Durascribe☐ T7 Transcription Kit purchased from Epicentre Technologies (Madison, Wis.).

The modified siRNAs (dsRNAs) made by these methods contain phosphodiester linked oligonucleotides. Standard methods for making modified single-stranded RNAs, such as antisense molecules, are useful for making modified siRNAs, as modified single-stranded RNAs can be annealed together to form double stranded RNAs. Such standard methods include, but are not limited to, those described in Chiang et al., *J. Biol. Chem.* 266, 18162-18171 (1991); Baker et al., *J. Biol. Chem.* 272, 11994-12000 (1997); Kawasaki et al., *J. Med. Chem.* 36, 831-841 (1993); Monia et al., *J. Biol. Chem.* 268, 14514-14522 (1993).

Example 9

To test whether siRNA directed to the HCV genome confers intracellular immunity against this human pathogen, a recently developed HCV cell culture systems in human hepatoma cell line, Huh-7, was used. One of the cell lines, 5-2, harbors autonomously replicating subgenomic HCV RNA (Bartenschlager, J. Virol, 2001). The subgenomic replicon carries firefly luciferase gene, allowing a reporter function assay as a measure of HCV RNA replication. Owing to cell culture adaptive mutations introduced into the genome, 5-2 cells replicate HCV RNA at levels of up to $5 \times 10^4$ virus particles/cell.

Using T7 transcription, several 21-bp siRNA duplexes against different regions of the 5'-UTR of the HCV genome were made. Briefly, two oligo double-stranded DNA molecules comprising the T7 promoter and the 5' UTR of HCV being oriented in either the sense direction or the antisense direction were generated. Each oligo DNA was then transcribed in vitro to produce (+) and (−) RNA and then treated with DNAase I to remove the DNA template. The two RNA strands were allowed to anneal at 37° C. overnight, generating dsRNA. After treating the dsRNA with RNAase T1 to remove the unreacted ssRNA species, the dsRNA was purified for transfection.

Two exemplary modified siRNAs are provided below (wherein the sense strand of both Chol-GL2 and GL2 is CGUACGCGGAAUACUUCGAUU, SEQ ID NO: 5, and antisense strand of both Chol-GL2 and GL2 is UCGAAGUAUUCCGCGUACGUU, SEQ ID NO: 6):

Each C and U within siRNA GL2, directed against the fruit fly luciferase gene, was substituted with 2'-F-U and 2'F-C. The modified siRNAs were transfected into the 5-2 cells using standard liposome transfection techniques. Specifically, the modified siRNAs were incubated for 4 hrs at 37° C. in a 250 μl cell suspension containing 0.5 μl of Oligofectamine (Invitrogen, Carlsbad, Calif.), for 20 hrs in 375 μl serum containing culture medium, and for 24 hrs at 37° C. in fresh medium without the liposome-siRNA complex. Luciferase activity was measured 48 hours after transfection to determine the effect of the modified siRNAs on HCV replication.

Figure 11:
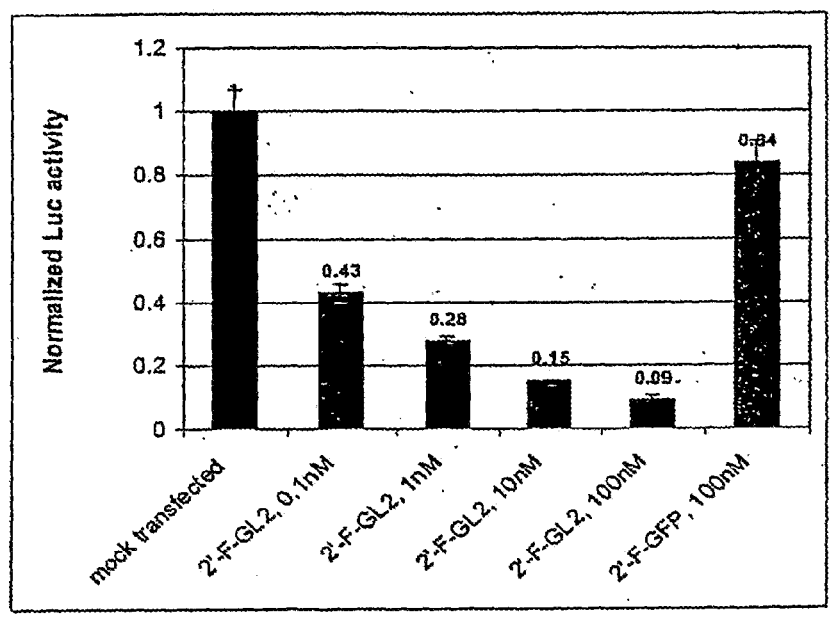
FIG. 11 depicts a dose response of normalized luciferase activity in Huh 7 cells containing a subgenomic HCV replicon (5-2 line) that were administered different concentrations of 2'-fluoro-siRNA (2'-F-GL2), which targets the fruit fly luciferase gene. Luciferase activity, which was measured at 2 days post-transfection, fell with increasing doses of siRNA. The luciferase assay was performed using a Firefly Luciferase kit (Promega Corp., Madison, Wis.), according to the manufacturer's instructions.

FIG. 11 shows that GL2 reduced the luciferase activity at increasing concentrations. Luciferase activity was reduced by 90% in cells transfected with 2'-F-GL2, but no significant reduction was seen in mocked transfected cells or with a control (2'-F-GFP=green fluorescent protein). The luciferase assay was carried out using a Luciferase assay system available from Promega Corp. (Madison, Wis.), according to the manufacturer's instructions.

Figure 12:
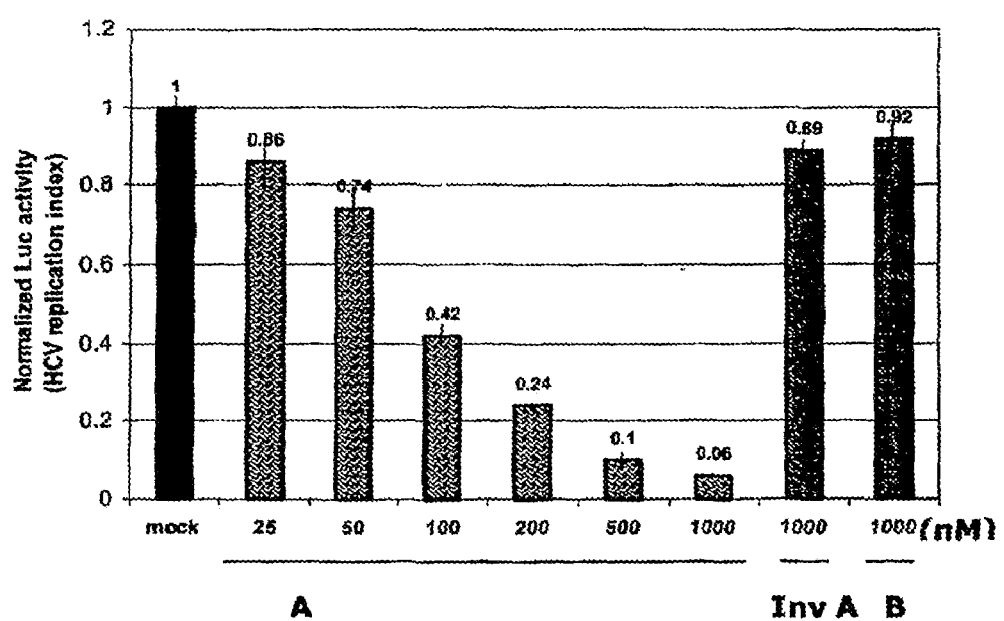
FIG. 12 demonstrates an inhibition of luciferase activity in 5-2 cells using the siRNA Chol-GL2 in the absence of liposomes.

The siRNA Chol-GL2 comprises a cholesteryl group on one of the 5' ends. 5-2 cells were incubated with various concentrations of Chol-GL2 in the absence of liposomes. Cells were harvested 48 hours after incubation and assayed for luciferase activity. FIG. 12 shows that Chol-GL2 inhibited luciferase gene activity in a dose-dependent manner. InvA refers to chol-GL2 in inverted sequence.

Example 10

Figure 13:
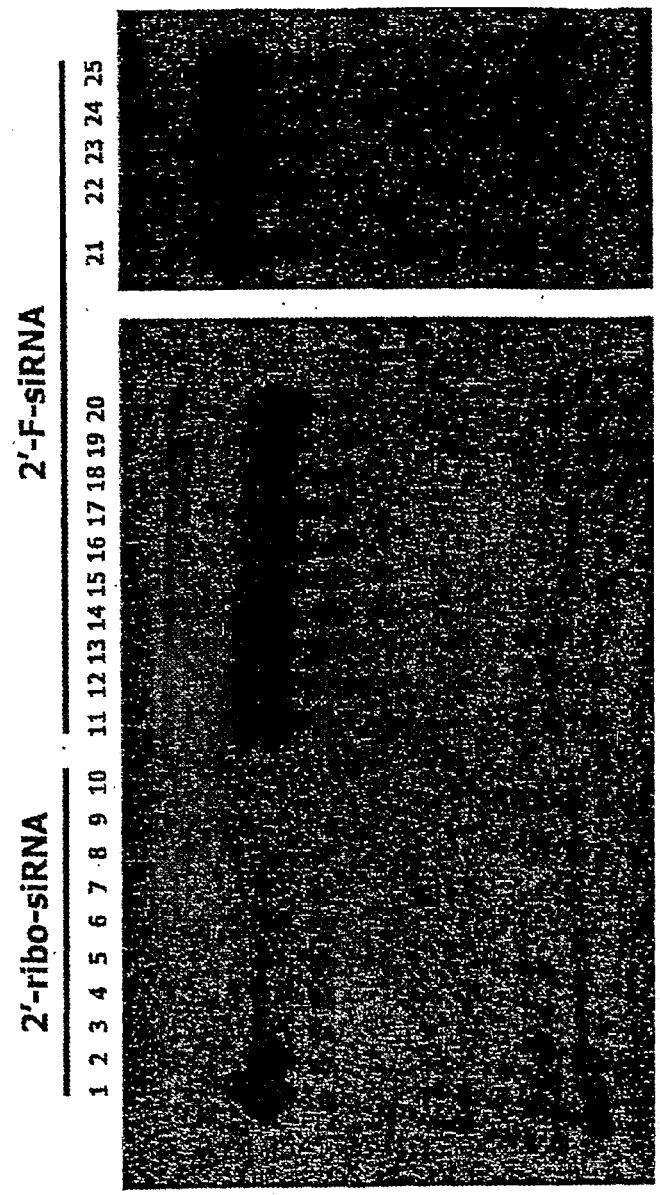
FIG. 13 depicts an autoradiograph of 5'-labeled siRNA duplexes separated by PAGE, and shows the stability of 2'-fluoro-modified siRNA (2'-F-GL2) incubated in human serum for up to 10 days. The siRNA duplexes were subjected to incubation with human serum and analysis by 20% PAGE. The composition of the lanes is as follows: Lanes 1, 11 and 21: $^{32}$P-end labeled siRNA alone; Lanes 2-10, 12-20 and 22-25: siRNA incubated with human serum. Lanes 2 & 12, 1 min; Lanes 3 & 13, 5 min; Lanes 4 & 14, 15 min; Lanes 5 & 15, 30 min; Lanes 6 & 16, 1 hr; Lanes 7 & 17, 2 hr; Lanes 8 & 18, 4 hr; Lanes 9 & 19, 8 hr; Lanes 10 & 20, 24 hr; Lanes 22, 24 hr; Lanes 23, 48 hr; Lanes 24, 120 hr; Lanes 25, 240 hr incubation, respectively.

To test the stability of 2' chemically modified siRNA compared to unmodified siRNA (siRNA), the following experiment is performed. Four nanograms of siRNA are added to a 20 μL volume of 80% human serum from a healthy donor. This mixture is incubated at 37 C.° for various times ranging from 1 minute up to 10 days. The results are depicted in lanes 2-10 of FIG. 13. The same process is performed for 2' fluorine modified siRNA (2'-F siRNA) as well and the results are shown in lanes 12-20 and 22-25 of FIG. 3. When the incubation process is finished, the mixtures are placed on ice and then immediately separated by PAGE along with a $^{32}$P-siRNA control (See Lanes 1, 11 and 21 of FIG. 13). The data show that the 2'-modified siRNA is stable over a period of 10 days as compared to unmodified siRNA.

Example 11

Figure 4:
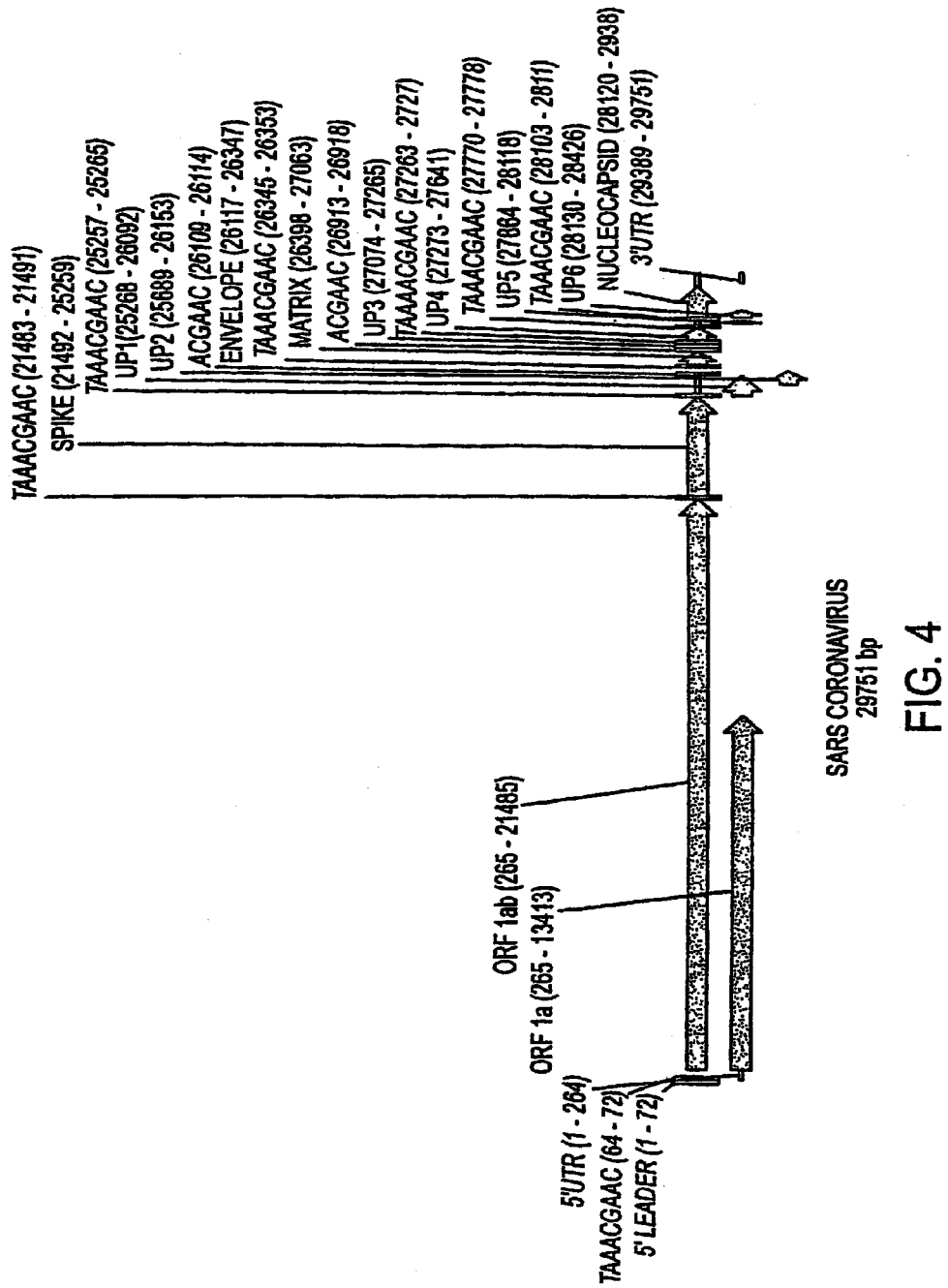
FIG. 4 is a schematic representation of the open reading frames of the SARS coronavirus (wherein "TAAAAC-GAAC" is represented by SEQ ID NO: 68).

To demonstrate the production of modified siRNA from long dsRNA, five micrograms of 1000 bp-long fluorinated dsRNAs (FIG. 14, panel (A)) were incubated overnight with 15 units of human Dicer at 37° C. The resulting diced-siRNAs were purified using a Sephadex G-25 column and electrophoresed on 20% PAGE (FIG. 14, panel (B)). FIG. 4 shows that recombinant human dicer effectively converts fluorinated-dsRNA into 2'F-siRNA.

Example 12

To further test whether siRNAs directed to the HCV genome confer intracellular immunity against this human pathogen, the assay described in Example 1 was employed to test siRNAC1, siRNAC2, siRNA5B1, siRNA5B2, and siRNA5B4, each of which is shown in FIG. 2. Each siRNA was tested at concentrations of 1 mM, 10 nM and 100 nM. As shown in FIG. 15, each of the siRNAs significantly inhibited luciferase activity in a dose-dependent manner. SiRNAC2 exhibited particular effectiveness.

Example 13

As a follow-up to the experiments reported in Example 9, assays were performed to demonstrate that the cholesterol modification, and not the fluoro modification directed siRNA molecules to Huh-7 liver cells. Huh-7 cells were incubated with various concentrations of two kinds of Chol-GL2 siRNAs: one having a 2'-fluoro modification and the other lacking such a modification. The results, shown in FIG. 16 demonstrate that the deliver of cholesterol-modified siRNA molecules to liver cells is due to the cholesterol, and not other modifications.

Example 14 siRNA was modified to include 2-Fluoro pyrimidines in place of all of the pyrimidines (2'-F-siRNA). This 2'-F-siRNA was further modified to include a two base deoxynucleotide "TT" sequence added to the 3' ends of the molecule in place of the ribolucleotide "UU" overhangs present in 2-F-siRNA (2'-F-siRNA 3'-X). FIG. 17 demonstrates that the further modification of the 2' fluorinated siRNA to include a 3'"dTdT" terminus resulted in significant increase in stability of the siRNA in human serum.

What is claimed is:

1. A method for inhibiting Hepatitis C Virus (HCV) replication in a patient, the method comprising the steps of:
   (a) administering to said patient a composition comprising a modified double-stranded RNA (dsRNA) or modified small interfering RNA (siRNA) in an amount effective to mediate RNA interference to inhibit HCV replication, wherein the modified dsRNA or modified siRNA comprises a first strand and a second strand, wherein the first strand is no more than about 30 ribonucleotides in length and the sequence of the first strand comprises the sequence of SEQ ID NO: 3 and the second strand is no more than 30 ribonucleotides in length and the sequence of the second strand comprises the sequence of SEQ ID NO: 4, wherein the modified dsRNA or modified siRNA is cholesterol-labeled, and (b) administering to said patient a cholesterol-lowering drug, wherein steps (a) and (b) can be performed simultaneously or in any order, and (c) wherein the cholesterol-lowering drug reduces the level of competing cholesterol in the serum, allowing more efficient uptake of the cholesterol-labeled modified dsRNA or modified siRNA by hepatocytes.

2. The method of claim 1, wherein said cholesterol-lowering drug is a statin, resin, nicotinic acid, gemfibrozil or clofibrate.

3. The method of claim 1, wherein said cholesterol-lowering drug is a statin.

4. The method of claim 1, wherein said modified dsRNA or modified siRNA is 2' modified.

5. The method of claim 1, wherein said modified dsRNA or modified siRNA is modified with a modification selected from the group consisting of fluoro-, methyl-, methoxyethyl- and propyl-modification.

6. The method of claim 5, wherein said fluoro-modification is a 2'-fluoro-modification or a 2',2'-difluoro-modification.

7. The method of claim 1, wherein at least one pyrimidine of said modified dsRNA or modified siRNA is modified, and said pyrimidine is cytosine, a derivative of cytosine, uracil, or a derivative of uracil.

8. The method of claim 7, wherein all of the pyrimidines in said modified dsRNA or modified siRNA are modified.

9. The method of claim 1, wherein said modified dsRNA or modified siRNA comprises a two base deoxynucleotide "TT" sequence at least one 3' end.

10. A method for inhibiting Hepatitis C Virus (HCV) replication in a patient, the method comprising the steps of:

(a) administering to said patient a composition comprising a modified double-stranded RNA (dsRNA) or modified small interfering RNA (siRNA) in an amount effective to mediate RNA interference to inhibit HCV replication, wherein the modified dsRNA or modified siRNA comprises a first strand and a second strand, wherein the first strand is the sequence of SEQ ID NO: 3 and the second strand is the sequence of SEQ ID NO: 4, wherein the modified dsRNA or modified siRNA is cholesterol-labeled, and (b) administering to said patient a cholesterol-lowering drug, wherein steps (a) and (b) can be performed simultaneously or in any order, and (c) wherein the cholesterol-lowering drug reduces the level of competing cholesterol in the serum, allowing more efficient uptake of the cholesterol-labeled modified dsRNA or modified siRNA by hepatocytes.

11. The method of claim 10, wherein said cholesterol-lowering drug is a statin, resin, nicotinic acid, gemfibrozil or clofibrate.

12. The method of claim 10, wherein said cholesterol-lowering drug is a statin.

13. The method of claim 10, wherein said modified dsRNA or modified siRNA is 2' modified.

14. The method of claim 10, wherein said modified dsRNA or modified siRNA is modified with a modification selected from the group consisting of fluoro-, methyl-, methoxyethyl- and propyl-modification.

15. The method of claim 14, wherein said fluoro-modification is a 2'-fluoro-modification or a 2',2'-difluoro-modification.

16. The method of claim 10, wherein at least one pyrimidine of said modified dsRNA or modified siRNA is modified, and said pyrimidine is cytosine, a derivative of cytosine, uracil, or a derivative of uracil.

17. The method of claim 16, wherein all of the pyrimidines in said modified dsRNA or modified siRNA are modified.

18. The method of claim 10, wherein said modified dsRNA or modified siRNA comprises a two base deoxynucleotide "TT" sequence at least one 3' end.

* * * * *

SEQUENCE LISTING

<160> NUMBER OF SEQ ID NOS: 68

<210> SEQ ID NO 1
<211> LENGTH: 29751
<212> TYPE: DNA
<213> ORGANISM: SARS coronavirus

<400> SEQUENCE: 1

| | | | | | |
|---|---|---|---|---|---|
| ttattaggtt | tttacctacc | caggaaaagc | caaccaacct | cgatctcttg | tagatctgtt | 60 |
| ctctaaacga | actttaaaat | ctgtgtagct | gtcgctcggc | tgcatgccta | gtgcacctac | 120 |
| gcagtataaa | caataataaa | ttttactgtc | gttgacaaga | aacgagtaac | tcgtccctct | 180 |
| tctgcagact | gcttacggtt | tcgtccgtgt | tgcagtcgat | catcagcata | cctaggtttc | 240 |
| gtccgggtgt | gaccgaaagg | taagatggag | agccttgttc | ttggtgtcaa | cgagaaaaca | 300 |
| cacgtccaac | tcagtttgcc | tgtccttcag | gttagagacg | tgctagtgcg | tggcttcggg | 360 |
| gactctgtgg | aagaggccct | atcggaggca | cgtgaacacc | tcaaaaatgg | cacttgtggt | 420 |
| ctagtagagc | tggaaaaagg | cgtactgccc | cagcttgaac | agccctatgt | gttcattaaa | 480 |
| cgttctgatg | ccttaagcac | caatcacggc | cacaaggtcg | ttgagctggt | tgcagaaatg | 540 |
| gacggcattc | agtacggtcg | tagcggtata | acactgggag | tactcgtgcc | acatgtgggc | 600 |
| gaaaccccaa | ttgcataccg | caatgttctt | cttcgtaaga | acgtaataa | gggagccggt | 660 |
| ggtcatagct | atggcatcga | tctaaagtct | tatgacttag | gtgacgagct | tggcactgat | 720 |
| cccattgaag | attatgaaca | aaactggaac | actaagcatg | gcagtggtgc | actccgtgaa | 780 |
| ctcactcgtg | agctcaatgg | aggtgcagtc | actcgctatg | tcgacaacaa | tttctgtggc | 840 |
| ccagatgggt | accctcttga | ttgcatcaaa | gattttctcg | cacgcgcggg | caagtcaatg | 900 |
| tgcactcttt | ccgaacaact | tgattacatc | gagtcgaaga | gaggtgtcta | ctgctgccgt | 960 |
| gaccatgagc | atgaaattgc | ctggttcact | gagcgctctg | ataagagcta | cgagcaccag | 1020 |
| acacccttcg | aaattaagag | tgccaagaaa | tttgacactt | tcaaagggga | atgcccaaag | 1080 |
| tttgtgtttc | ctcttaactc | aaaagtcaaa | gtcattcaac | cacgtgttga | aaagaaaaag | 1140 |
| actgagggt | tcatggggcg | tatacgctct | gtgtaccctg | ttgcatctcc | acaggagtgt | 1200 |
| aacaatatgc | acttgtctac | cttgatgaaa | tgtaatcatt | gcgatgaagt | tcatggcag | 1260 |
| acgtgcgact | ttctgaaagc | cacttgtgaa | cattgtggca | ctgaaaattt | agttattgaa | 1320 |
| ggacctacta | catgtgggta | cctacctact | aatgctgtag | tgaaaatgcc | atgtcctgcc | 1380 |
| tgtcaagacc | cagagattgg | acctgagcat | agtgttgcag | attatcacaa | ccactcaaac | 1440 |
| attgaaactc | gactccgcaa | gggaggtagg | actagatgtt | ttggaggctg | tgtgtttgcc | 1500 |
| tatgttggct | gctataataa | gcgtgcctac | tgggttcctc | gtgctagtgc | tgatattggc | 1560 |
| tcaggccata | ctggcattac | tggtgacaat | gtggagacct | tgaatgagga | tctccttgag | 1620 |
| atactgagtc | gtgaacgtgt | taacattaac | attgttggcg | attttcattt | gaatgaagag | 1680 |
| gttgccatca | tttggcatc | tttctctgct | tctacaagtg | cctttattga | cactataaag | 1740 |

```
agtcttgatt acaagtcttt caaaaccatt gttgagtcct gcggtaacta taaagttacc    1800
aagggaaagc ccgtaaaagg tgcttggaac attggacaac agagatcagt tttaacacca    1860
ctgtgtggtt ttccctcaca ggctgctggt gttatcagat caattttttgc gcgcacactt   1920
gatgcagcaa accactcaat tcctgatttg caaagagcag ctgtcaccat acttgatggt    1980
atttctgaac agtcattacg tcttgtcgac gccatggttt atacttcaga cctgctcacc    2040
aacagtgtca ttattatggc atatgtaact ggtggtcttg tacaacagac ttctcagtgg    2100
ttgtctaatc ttttgggcac tactgttgaa aaactcaggc ctatctttga atggattgag    2160
gcgaaactta gtgcaggagt tgaatttctc aaggatgctt gggagattct caaatttctc    2220
attacaggtg tttttgacat cgtcaagggt caaatacagg ttgcttcaga taacatcaag    2280
gattgtgtaa aatgcttcat tgatgttgtt aacaaggcac tcgaaatgtg cattgatcaa    2340
gtcactatcg ctggcgcaaa gttgcgatca ctcaacttag gtgaagtctt catcgctcaa    2400
agcaagggac tttaccgtca gtgtatacgt ggcaaggagc agctgcaact actcatgcct    2460
cttaaggcac aaaagaagt aacctttctt gaaggtgatt cacatgacac agtacttacc     2520
tctgaggagg ttgttctcaa gaacggtgaa ctcgaagcac tcgagacgcc cgttgatagc    2580
ttcacaaatg gagctatcgt cggcacacca gtctgtgtaa atggcctcat gctcttagag    2640
attaaggaca agaacaata ctgcgcattg tctcctggtt tactggctac aaacaatgtc     2700
tttcgcttaa aggggggtgc accaattaaa ggtgtaacct ttggagaaga tactgtttgg    2760
gaagttcaag gttacaagaa tgtgagaatc acatttgagc ttgatgaacg tgttgacaaa    2820
gtgcttaatg aaaagtgctc tgtctacact gttgaatccg gtaccgaagt tactgagttt    2880
gcatgtgttg tagcagaggc tgttgtgaag actttacaac cagtttctga tctccttacc    2940
aacatgggta ttgatcttga tgagtggagt gtagctacat tctacttatt tgatgatgct    3000
ggtgaagaaa acttttcatc acgtatgtat tgttcctttt accctccaga tgaggaagaa    3060
gaggacgatg cagagtgtga ggaagaagaa attgatgaaa cctgtgaaca tgagtacggt    3120
acagaggatg attatcaagg tctccctctg gaatttggtg cctcagctga acagttcga    3180
gttgaggaag aagaagagga agactggctg gatgatacta ctgagcaatc agagattgag    3240
ccagaaccag aacctacacc tgaagaacca gttaatcagt ttactggtta ttttaaactt    3300
actgacaatg ttgccattaa atgtgttgac atcgttaagg aggcacaaag tgctaatcct    3360
atggtgattg taaatgctgc taacatacac ctgaaacatg gtggtggtgt agcaggtgca    3420
ctcaacaagg caaccaatgg tgccatgcaa aaggagagtg atgattacat taagctaaat    3480
ggccctctta cagtaggagg gtcttgtttg ctttctggac ataatcttgc taagaagtgt    3540
ctgcatgttg ttggacctaa cctaaatgca ggtgaggaca tccagcttct taaggcagca    3600
tatgaaaatt tcaattcaca ggacatctta cttgcaccat tgttgtcagc aggcatattt    3660
ggtgctaaac cacttcagtc tttacaagtg tgcgtgcaga cggttcgtac acaggtttat    3720
attgcagtca atgacaaagc tctttatgag caggttgtca tggattatct tgataacctg    3780
aagcctagag tggaagcacc taaacaagag agccaccaa acacagaaga ttccaaaact     3840
gaggagaaat ctgtcgtaca gaagcctgtc gatgtgaagc aaaaattaa ggcctgcatt     3900
gatgaggtta ccacaacact ggaagaaact aagtttctta ccaataagtt actcttgttt    3960
gctgatatca tggtaagct ttaccatgat tctcagaaca tgcttagagg tgaagatatg    4020
tctttccttg agaaggatgc accttacatg gtaggtgatg ttatcactag tggtgatatc    4080
acttgtgttg taataccctc caaaaaggct ggtggcacta ctgagatgct ctcaagagct    4140
```

```
ttgaagaaag tgccagttga tgagtatata accacgtacc ctggacaagg atgtgctggt    4200
tatacacttg aggaagctaa gactgctctt aagaaatgca atctgcatt ttatgtacta    4260 ccttcagaag cacctaatgc taaggaagag attctaggaa ctgtatcctg gaatttgaga    4320
gaaatgcttg ctcatgctga agagacaaga aaattaatgc ctatatgcat ggatgttaga    4380
gccataatgg caaccatcca acgtaagtat aaaggaatta aaattcaaga gggcatcgtt    4440
gactatggtg tccgattctt cttttatact agtaaagagc ctgtagcttc tattattacg    4500
aagctgaact ctctaaatga gccgcttgtc acaatgccaa ttggttatgt gacacatggt    4560
tttaatcttg aagaggctgc gcgctgtatg cgttctctta agctcctgc cgtagtgtca    4620 gtatcatcac cagatgctgt tactacatat aatggatacc tcacttcgtc atcaaagaca    4680
tctgaggagc actttgtaga aacagtttct ttggctggct cttacagaga ttggtcctat    4740
tcaggacagc gtacagagtt aggtgttgaa tttcttaagc gtggtgacaa aattgtgtac    4800
cacactctgg agagccccgt cgagtttcat cttgacggtg aggttctttc acttgacaaa    4860
ctaaagagtc tcttatccct gcgggaggtt aagactataa agtgttcac aactgtggac    4920 aacactaatc tccacacaca gcttgtggat atgtctatga catatggaca gcagtttggt    4980
ccaacatact tggatggtgc tgatgttaca aaaattaaac ctcatgtaaa tcatgagggt    5040
aagactttct ttgtactacc tagtgatgac acactacgta gtgaagcttt cgagtactac    5100
catactcttg atgagagttt tcttggtagg tacatgtctg ctttaaacca cacaaagaaa    5160
tggaaatttc ctcaagttgg tggtttaact tcaattaaat gggctgataa caattgttat    5220
ttgtctagtg ttttattagc acttcaacag cttgaagtca aattcaatgc accagcactt    5280
caagaggctt attatagagc ccgtgctggt gatgctgcta acttttgtgc actcatactc    5340
gcttacagta ataaaactgt tggcgagctt ggtgatgtca gagaaactat gacccatctt    5400
ctacagcatg ctaatttgga atctgcaaag cgagttctta atgtggtgtg taaacattgt    5460
ggtcagaaaa ctactacctt aacgggtgta gaagctgtga tgtatatggg tactctatct    5520
tatgataatc ttaagacagg tgtttccatt ccatgtgtgt gtggtcgtga tgctacacaa    5580
tatctagtac aacaagagtc ttctttttgtt atgatgtctg caccacctgc tgagtataaa    5640
ttacagcaag gtacattctt atgtgcgaat gagtacactg gtaactatca gtgtggtcat    5700
tacactcata taactgctaa ggagaccctc tatcgtattg acggagctca ccttacaaag    5760
atgtcagagt acaaaggacc agtgactgat gttttctaca aggaaacatc ttacactaca    5820
accatcaagc ctgtgtcgta taaactcgat ggagttactt acacagagat tgaaccaaaa    5880
ttggatgggt attataaaaa ggataatgct tactatacag agcagccat agaccttgta    5940 ccaactcaac cattaccaaa tgcgagtttt gataatttca actcacatg ttctaacaca    6000 aaatttgctg atgatttaaa tcaaatgaca ggcttcacaa agccagcttc acgagagcta    6060
tctgtcacat tcttcccaga cttgaatggc gatgtagtgg ctattgacta tagacactat    6120
tcagcgagtt tcaagaaagg tgctaaatta ctgcataagc caattgtttg gcacattaac    6180
caggctacaa ccaagacaac gttcaaacca aacacttggt gtttacgttg tctttggagt    6240
acaaagccag tagatacttc aaattcattt gaagttctgg cagtagaaga cacacaagga    6300
atggacaatc ttgcttgtga aagtcaacaa cccacctctg aagaagtagt ggaaaatcct    6360
accatacaga aggaagtcat agagtgtgac gtgaaaacta ccgaagttgt aggcaatgtc    6420
atacttaaac catcagatga aggtgttaaa gtaacacaag agttaggtca tgaggatctt    6480
atggctgctt atgtggaaaa cacaagcatt accattaaga aacctaatga gctttcacta    6540
```

```
gccttaggtt taaaaacaat tgccactcat ggtattgctg caattaatag tgttccttgg    6600
agtaaaattt tggcttatgt caaaccattc ttaggacaag cagcaattac aacatcaaat    6660
tgcgctaaga gattagcaca acgtgtgttt aacaattata tgccttatgt gtttacatta    6720
ttgttccaat tgtgtacttt tactaaaagt accaattcta gaattagagc ttcactacct    6780
acaactattg ctaaaaatag tgttaagagt gttgctaaat tatgtttgga tgccggcatt    6840
aattatgtga agtcacccaa attttctaaa ttgttcacaa tcgctatgtg gctattgttg    6900
ttaagtattt gcttaggttc tctaatctgt gtaactgctg cttttggtgt actcttatct    6960
aattttggtg ctccttctta ttgtaatggc gttagagaat tgtatcttaa ttcgtctaac    7020
gttactacta tggatttctg tgaaggttct tttccttgca gcatttgttt aagtggatta    7080
gactcccttg attcttatcc agctcttgaa accattcagg tgacgatttc atcgtacaag    7140
ctagacttga caattttagg tctggccgct gagtgggttt tggcatatat gttgttcaca    7200
aaattctttt atttattagg tctttcagct ataatgcagg tgttctttgg ctattttgct    7260
agtcatttca tcagcaattc ttggctcatg tggtttatca ttagtattgt acaaatggca    7320
cccgtttctg caatggttag gatgtacatc ttctttgctt ctttctacta catatggaag    7380
agctatgttc atatcatgga tggttgcacc tcttcgactt gcatgatgtg ctataagcgc    7440
aatcgtgcca cacgcgttga gtgtacaact attgttaatg gcatgaagag atctttctat    7500
gtctatgcaa atggaggccg tggcttctgc aagactcaca attggaattg tctcaattgt    7560
gacacatttt gcactggtag tacattcatt agtgatgaag ttgctcgtga tttgtcactc    7620
cagtttaaaa gaccaatcaa ccctactgac cagtcatcgt atattgttga tagtgttgct    7680
gtgaaaaatg gcgcgcttca cctctacttt gacaaggctg tcaaaagac ctatgagaga    7740 catccgctct cccatttgt caatttagac aatttgagag ctaacaacac taaaggttca    7800
ctgcctatta tgtcatagt ttttgatggc aagtccaaat gcgacgagtc tgcttctaag    7860
tctgcttctg tgtactacag tcagctgatg tgccaaccta ttctgttgct tgaccaagct    7920
cttgtatcag acgttggaga tagtactgaa gtttccgtta agatgtttga tgcttatgtc    7980
gacacctttt cagcaacttt tagtgttcct atggaaaaac ttaaggcact tgttgctaca    8040
gctcacagcg agttagcaaa gggtgtagct ttagatggtg tccttttctac attcgtgtca    8100 gctgcccgac aaggtgttgt tgataccgat gttgacacaa aggatgttat tgaatgtctc    8160
aaactttcac atcactctga cttagaagtg acaggtgaca gttgtaacaa tttcatgctc    8220
acctataata aggttgaaaa catgacgccc agagatcttg gcgcatgtat tgactgtaat    8280
gcaaggcata tcaatgccca agtagcaaaa agtcacaatg tttcactcat ctggaatgta    8340
aaagactaca tgtctttatc tgaacagctg cgtaaacaaa ttcgtagtgc tgccaagaag    8400
aacaacatac ttttagact aacttgtgct acaactagac aggttgtcaa tgtcataact    8460
actaaaatct cactcaaggg tggtaagatt gttagtactt gttttaaact tatgcttaag    8520
gccacattat tgtgcgttct tgctgcattg gtttgttata tcgttatgcc agtacataca    8580
ttgtcaatcc atgatggtta cacaaatgaa atcattggtt acaaagccat tcaggatggt    8640
gtcactcgtg acatcatttc tactgatgat tgttttgcaa ataaacatgc tggttttgac    8700
gcatggttta gccagcgtgg tggttcatac aaaaatgaca aaagctgccc tgtagtagct    8760
gctatcatta caagagagat tggtttcata gtgcctggct taccgggtac gtgctgagaa    8820
gcaatcaatg tgacttctt gcattttcta cctcgtgttt ttagtgctgt tggcaacatt    8880
tgctacacac cttccaaact cattgagtat agtgattttg ctacctctgc ttgcgttctt    8940
```

```
gctgctgagt gtacaatttt taaggatgct atgggcaaac ctgtgccata ttgttatgac    9000
actaatttgc tagagggttc tatttcttat agtgagcttc gtccagacac tcgttatgtg    9060
cttatggatg gttccatcat acagtttcct aacacttacc tggagggttc tgttagagta    9120
gtaacaactt ttgatgctga gtactgtaga catggtacat gcgaaaggtc agaagtaggt    9180
atttgcctat ctaccagtgg tagatgggtt cttaataatg agcattacag agctctatca    9240
ggagttttct gtggtgttga tgcgatgaat ctcatagcta acatctttac tcctcttgtg    9300
caacctgtgg gtgctttaga tgtgtctgct tcagtagtgg ctggtggtat tattgccata    9360
ttggtgactt gtgctgccta ctactttatg aaattcagac gtgtttttgg tgagtacaac    9420
catgttgttg ctgctaatgc acttttgttt ttgatgtctt tcactatact ctgtctggta    9480
ccagcttaca gctttctgcc gggagtctac tcagtctttt acttgtactt gacattctat    9540
ttcaccaatg atgtttcatt cttggctcac cttcaatggt ttgccatgtt ttctcctatt    9600
gtgccttttt ggataacagc aatctatgta ttctgtattt ctctgaagca ctgccattgg    9660
ttctttaaca actatcttag gaaaagagtc atgtttaatg gagttacatt tagtaccttc    9720
gaggaggctg ctttgtgtac cttttttgctc aacaaggaaa tgtacctaaa attgcgtagc    9780
gagacactgt tgccacttac acagtataac aggtatcttg ctctatataa caagtacaag    9840
tatttcagtg gagccttaga tactaccagc tatcgtgaag cagcttgctg ccacttagca    9900
aaggctctaa atgactttag caactcaggt gctgatgttc tctaccaacc accacagaca    9960
tcaatcactt ctgctgttct gcagagtggt tttaggaaaa tggcattccc gtcaggcaaa    10020
gttgaagggt gcatggtaca agtaacctgt ggaactacaa ctcttaatgg attgtggttg    10080
gatgacacag tatactgtcc aagacatgtc atttgcacag cagaagacat gcttaatcct    10140
aactatgaag atctgctcat tcgcaaatcc aaccatagct ttcttgttca ggctggcaat    10200
gttcaacttc gtgttattgg ccattctatg caaaattgtc tgcttaggct taaagttgat    10260
acttctaacc ctaagacacc caagtataaa tttgtccgta tccaacctgg tcaaacatttt    10320 tcagttctag catgctacaa tggttcacca tctggtgttt atcagtgtgc catgagacct    10380
aatcatacca ttaaaggttc tttccttaat ggatcatgtg gtagtgttgg ttttaacatt    10440
gattatgatt gcgtgtcttt ctgctatatg catcatatgg agcttccaac aggagtacac    10500
gctggtactg acttagaagg taaattctat ggtccatttg ttgacagaca aactgcacag    10560
gctgcaggta cagacacaac cataacatta aatgttttgg catggctgta tgctgctgtt    10620
atcaatggtg ataggtggtt tcttaataga ttcaccacta ctttgaatga ctttaacctt    10680
gtggcaatga gtacaactga gtaacccttt acacaagatc atgttgacat attgggacct    10740 cttctgctc aaacaggaat tgccgtctta gatatgtgtg ctgctttgaa agagctgctg    10800
cagaatggta tgaatggtcg tactatcctt ggtagcacta ttttagaaga tgagtttaca    10860
ccatttgatg ttgttagaca atgctctggt gttaccttcc aaggtaagtt caagaaaatt    10920
gttaagggca ctcatcattg gatgcttttta actttcttga catcactatt gattcttgtt    10980
caaagtacac agtggtcact gttttctctt gtttacgaga atgctttctt gccatttact    11040
cttggtatta tggcaattgc tgcatgtgct atgctgcttg ttaagcataa gcacgcattc    11100
ttgtgcttgt ttctgttacc ttctcttgca acagttgctt actttaatat ggtctacatg    11160
cctgctagct gggtgatgcg tatcatgaca tggcttgaat tggctgacac tagcttgtct    11220
ggttataggc ttaaggattg tgttatgtat gcttcagctt tagttttgct tattctcatg    11280
acagctcgca ctgtttatga tgatgctgct agacgtgttt ggacactgat gaatgtcatt    11340
```

```
acacttgttt acaaagtcta ctatggtaat gctttagatc aagctatttc catgtgggcc    11400
ttagttattt ctgtaacctc taactattct ggtgtcgtta cgactatcat gtttttagct    11460
agagctatag tgtttgtgtg tgttgagtat tacccattgt tatttattac tggcaacacc    11520
ttacagtgta tcatgcttgt ttattgtttc ttaggctatt gttgctgctg ctactttggc    11580
cttttctgtt tactcaaccg ttacttcagg cttactcttg gtgtttatga ctacttggtc    11640
tctacacaag aatttaggta tatgaactcc caggggcttt tgcctcctaa gagtagtatt    11700
gatgctttca agcttaacat taagttgttg ggtattggag gtaaaccatg tatcaaggtt    11760
gctactgtac agtctaaaat gtctgacgta aagtgcacat ctgtggtact gctctcggtt    11820
cttcaacaac ttagagtaga gtcatcttct aaattgtggg cacaatgtgt acaactccac    11880
aatgatattc ttcttgcaaa agacacaact gaagctttcg agaagatggt ttctcttttg    11940
tctgttttgc tatccatgca gggtgctgta gacattaata ggttgtgcga ggaaatgctc    12000
gataaccgtg ctactcttca ggctattgct tcagaattta gttctttacc atcatatgcc    12060
gcttatgcca ctgcccagga ggcctatgag caggctgtag ctaatggtga ttctgaagtc    12120
gttctcaaaa agttaaagaa atctttgaat gtggctaaat ctgagtttga ccgtgatgct    12180
gccatgcaac gcaagttgga aaagatggca gatcaggcta tgacccaaat gtacaaacag    12240
gcaagatctg aggacaagag ggcaaaagta actagtgcta tgcaaacaat gctcttcact    12300
atgcttagga agcttgataa tgatgcactt aacaacatta tcaacaatgc gcgtgatggt    12360
tgtgttccac tcaacatcat accattgact acagcagcca aactcatggt tgttgtccct    12420
gattatggta cctacaagaa cacttgtgat ggtaacacct ttacatatgc atctgcactc    12480
tgggaaatcc agcaagttgt tgatgcggat agcaagatta ttcaacttag tgaaattaac    12540
atggacaatt caccaaattt ggcttggcct cttattgtta cagctctaag agccaactca    12600
gctgttaaac tacagaataa tgaactgagt ccagtagcac tacgacagat gtcctgtgcg    12660
gctggtacca cacaaacagc ttgtactgat gacaatgcac ttgcctacta taacaattcg    12720
aagggaggta ggtttgtgct ggcattacta tcagaccacc aagatctcaa atgggctaga    12780
ttccctaaga gtgatggtac aggtacaatt tacacagaac tggaaccacc ttgtaggttt    12840
gttacagaca caccaaaagg gcctaaagtg aaatacttgt acttcatcaa aggcttaaac    12900
aacctaaata gaggtatggt gctgggcagt ttagctgcta cagtacgtct tcaggctgga    12960
aatgctacag aagtacctgc caattcaact gtgctttcct tctgtgcttt tgcagtagac    13020
cctgctaaag catataagga ttacctagca agtggaggac aaccaatcac caactgtgtg    13080
aagatgttgt gtacacacac tggtacagga caggcaatta ctgtaacacc agaagctaac    13140
atggaccaag agtcctttgg tggtgcttca tgttgtctgt attgtagatg ccacattgac    13200
catccaaatc ctaaaggatt ctgtgacttg aaaggtaagt acgtccaaat acctaccact    13260
tgtgctaatg acccagtggg ttttacactt agaaacacag tctgtaccgt ctgcggaatg    13320
tggaaaggtt atggctgtag ttgtgaccaa ctccgcgaac ccttgatgca gtctgcggat    13380
gcatcaacgt ttttaaacgg gtttgcgtg taagtgcagc ccgtcttaca ccgtgcggca    13440
caggcactag tactgatgtc gtctacaggg ctttttgatat ttacaacgaa aaagttgctg    13500
gttttgcaaa gttcctaaaa actaattgct gtcgcttcca ggagaaggat gaggaaggca    13560
atttattaga ctcttacttt gtagttaaga gcatactat gtctaactac caacatgaag    13620
agactattta taacttggtt aaagattgtc cagcggttgc tgtccatgac ttttcaagt    13680
ttagagtaga tggtgacatg gtaccacata tatcacgtca gcgtctaact aaatacacaa    13740
```

```
tggctgattt agtctatgct ctacgtcatt ttgatgaggg taattgtgat acattaaaag    13800
aaatactcgt cacatacaat tgctgtgatg atgattattt caataagaag gattggtatg    13860
acttcgtaga gaatcctgac atcttacgcg tatatgctaa cttaggtgag cgtgtacgcc    13920
aatcattatt aaagactgta caattctgcg atgctatgcg tgatgcaggc attgtaggcg    13980
tactgacatt agataatcag gatcttaatg ggaactggta cgatttcggt gatttcgtac    14040
aagtagcacc aggctgcgga gttcctattg tggattcata ttactcattg ctgatgccca    14100
tcctcacttt gactagggca ttggctgctg agtcccatat ggatgctgat ctcgcaaaac    14160
cacttattaa gtgggatttg ctgaaatatg attttacgga agagagactt tgtctcttcg    14220
accgttattt taaatattgg gaccagacat accatcccaa ttgtattaac tgtttggatg    14280
ataggtgtat ccttcattgt gcaaacttta atgtgttatt ttctactgtg tttccaccta    14340
caagttttgg accactagta agaaaaatat ttgtagatgg tgttccttt gttgtttcaa    14400 ctggatacca ttttcgtgag ttaggagtcg tacataatca ggatgtaaac ttacatagct    14460
cgcgtctcag ttttcaaggaa cttttagtgt atgctgctga tccagctatg catgcagctt    14520
ctggcaattt attgctagat aaacgcacta catgcttttc agtagctgca ctaacaaaca    14580
atgttgcttt tcaaactgtc aaacccggta attttaataa agacttttat gactttgctg    14640
tgtctaaagg tttctttaag gaaggaagtt ctgttgaact aaaacacttc ttctttgctc    14700
aggatggcaa cgctgctatc agtgattatg actattatcg ttataatctg ccaacaatgt    14760
gtgatatcag acaactccta ttcgtagttg aagttgttga taaatacttt gattgttacg    14820
atggtggctg tattaatgcc aaccaagtaa tcgttaacaa tctggataaa tcagctggtt    14880 tcccattta taaatggggt aaggctagac tttattatga ctcaatgagt tatgaggatc    14940
aagatgcact tttcgcgtat actaagcgta atgtcatccc tactataact caaatgaatc    15000
ttaagtatgc cattagtgca aagaatagag ctcgcaccgt agctggtgtc tctatctgta    15060
gtactatgac aaatagacag tttcatcaga aattattgaa gtcaatagcc gccactagag    15120
gagctactgt ggtaattgga acaagcaagt tttacggtgg ctggcataat atgttaaaaa    15180
ctgtttacag tgatgtagaa actccacacc ttatgggttg ggattatcca aaatgtgaca    15240
gagccatgcc taacatgctt aggataatgg cctctcttgt tcttgctcgc aaacataaca    15300
cttgctgtaa cttatcacac cgtttctaca ggttagctaa cgagtgtgcg caagtattaa    15360
gtgagatggt catgtgtggc ggctcactat atgttaaacc aggtggaaca tcatccggtg    15420
atgctacaac tgcttatgct aatagtgtct ttaacatttg tcaagctgtt acagccaatg    15480
taaatgcact tctttcaact gatggtaata agatagctga caagtatgtc cgcaatctac    15540
aacacaggct ctatgagtgt ctctatagaa atagggatgt tgatcatgaa ttcgtggatg    15600
agttttacgc ttacctgcgt aaacatttct ccatgatgat tctttctgat gatgccgttg    15660
tgtgctataa cagtaactat gcggctcaag gtttagtagc tagcattaag aactttaagg    15720
cagttcttta ttatcaaaat aatgtgttca tgtctgaggc aaaatgttgg actgagactg    15780
accttactaa aggacctcac gaattttgct cacagcatac aatgctagtt aaacaaggag    15840
atgattacgt gtacctgcct tacccagatc catcaagaat attaggcgca ggctgttttg    15900
tcgatgatat tgtcaaaaca gatggtacac ttatgattga aaggttcgtg tcactggcta    15960
ttgatgctta cccacttaca aaacatccta atcaggagta tgctgatgtc tttcacttgt    16020
atttacaata cattagaaag ttacatgatg agcttactgg ccacatgttg gacatgtatt    16080
ccgtaatgct aactaatgat aacacctcac ggtactggga acctgagttt tatgaggcta    16140
```

```
tgtacacacc acatacagtc ttgcaggctg taggtgcttg tgtattgtgc aattcacaga    16200
cttcacttcg ttgcggtgcc tgtattagga gaccattcct atgttgcaag tgctgctatg    16260
accatgtcat ttcaacatca cacaaattag tgttgtctgt taatccctat gtttgcaatg    16320
ccccaggttg tgatgtcact gatgtgacac aactgtatct aggaggtatg agctattatt    16380
gcaagtcaca taagcctccc attagttttc cattatgtgc taatggtcag gtttttggtt    16440
tatacaaaaa cacatgtgta ggcagtgaca atgtcactga cttcaatgcg atagcaacat    16500
gtgattggac taatgctggc gattacatac ttgccaacac ttgtactgag agactcaagc    16560
ttttcgcagc agaaacgctc aaagccactg aggaaacatt taagctgtca tatggtattg    16620
ccactgtacg cgaagtactc tctgacagag aattgcatct ttcatgggag gttggaaaac    16680
ctagaccacc attgaacaga aactatgtct ttactggtta ccgtgtaact aaaaatagta    16740
aagtacagat tggagagtac acctttgaaa aggtgactat tggtgatgct gttgtgtaca    16800
gaggtactac gacatacaag ttgaatgttg gtgattactt tgtgttgaca tctcacactg    16860
taatgccact tagtgcacct actctagtgc cacaagagca ctatgtgaga attactggct    16920
tgtacccaac actcaacatc tcagatgagt tttctagcaa tgttgcaaat tatcaaaagg    16980
tcggcatgca aaagtactct acactccaag gaccacctgg tactggtaag agtcattttg    17040
ccatcggact tgctctctat tacccatctg ctcgcatagt gtatacggca tgctctcatg    17100
cagctgttga tgccctatgt gaaaaggcat taaatatttt gcccatagat aaatgtagta    17160
gaatcatacc tgcgcgtgcg cgcgtagagt gttttgataa attcaaagtg aattcaacac    17220
tagaacagta tgttttctgc actgtaaatg cattgccaga aacaactgct gacattgtag    17280
tctttgatga aatctctatg ctactaatt atgacttgag tgttgtcaat gctagacttc    17340
gtgcaaaaca ctacgtctat attggcgatc ctgctcaatt accagccccc cgcacattgc    17400
tgactaaagg cacactagaa ccagaatatt ttaattcagt gtgcagactt atgaaaacaa    17460
taggtccaga catgttcctt ggaacttgtc gccgttgtcc tgctgaaatt gttgacactg    17520
tgagtgcttt agtttatgac aataagctaa aagcacacaa ggataagtca gctcaatgct    17580
tcaaaatgtt ctacaaaggt gttattacac atgatgtttc atctgcaatc aacagacctc    17640
aaataggcgt tgtaagagaa tttcttacac gcaatcctgc ttggagaaaa gctgttttta    17700 tctcaccta taattcacag aacgctgtag cttcaaaaat cttaggattg cctacgcaga    17760
ctgttgattc atcacagggt tctgaatatg actatgtcat attcacacaa actactgaaa    17820
cagcacactc ttgtaatgtc aaccgcttca atgtggctat cacaagggca aaaattggca    17880
ttttgtgcat aatgtctgat agagatcttt atgacaaact gcaatttaca agtctagaaa    17940
taccacgtcg caatgtggct acattacaag cagaaatgt aactggactt tttaaggact    18000
gtagtaagat cattactggt cttcatccta cacaggcacc tacacacctc agcgttgata    18060
taaagttcaa gactgaagga ttatgtgttg acatacagg cataccaaag gacatgacct    18120
accgtagact catctctatg atgggtttca aaatgaatta ccaagtcaat ggttaccctca    18180 atatgtttat cacccgcgaa gaagctattc gtcacgttcg tgcgtggatt ggctttgatg    18240
tagagggctg tcatgcaact agagatgctg tgggtactaa cctacctctc cagctaggat    18300
tttctacagg tgttaactta gtagctgtac cgactggtta tgttgacact gaaaataaca    18360
cagaattcac cagagttaat gcaaaacctc caccaggtga ccagtttaaa catcttatac    18420
cactcatgta taaggcttg ccctggaatg tagtgcgtat taagatagta caaatgctca    18480
gtgatacact gaaaggattg tcagacagag tcgtgttcgt cctttgggcg catggctttg    18540
```

```
agcttacatc aatgaagtac tttgtcaaga ttggacctga aagaacgtgt tgtctgtgtg   18600
acaaacgtgc aacttgcttt tctacttcat cagatactta tgcctgctgg aatcattctg   18660
tgggttttga ctatgtctat aacccattta tgattgatgt tcagcagtgg ggctttacgg   18720
gtaaccttca gagtaaccat gaccaacatt gccaggtaca tggaaatgca catgtggcta   18780
gttgtgatgc tatcatgact agatgtttag cagtccatga gtgctttgtt aagcgcgttg   18840
attggtctgt tgaataccct attataggag atgaactgag ggttaattct gcttgcagaa   18900
aagtacaaca catggttgtg aagtctgcat tgcttgctga taagtttcca gttcttcatg   18960
acattggaaa tccaaaggct atcaagtgtg tgcctcaggc tgaagtagaa tggaagttct   19020
acgatgctca gccatgtagt gacaaagctt acaaaataga ggaactcttc tattcttatg   19080
ctacacatca cgataaattc actgatggtg tttgtttgtt ttggaattgt aacgttgatc   19140
gttacccagc caatgcaatt gtgtgtaggt ttgacacaag agtcttgtca aacttgaact   19200
taccaggctg tgatggtggt agtttgtatg tgaataagca tgcattccac actccagctt   19260
tcgataaaag tgcatttact aatttaaagc aattgccttt cttttactat tctgatagtc   19320
cttgtgagtc tcatggcaaa caagtagtgt cggatattga ttatgttcca ctcaaatctg   19380
ctacgtgtat tacacgatgc aatttaggtg gtgctgtttg cagacaccat gcaaatgagt   19440
accgacagta cttggatgca tataatatga tgatttctgc tggatttagc ctatggattt   19500
acaaacaatt tgatacttat aacctgtgga atacatttac caggttacag agtttagaaa   19560
atgtggctta taatgttgtt aataaaggac actttgatgg acacgccggc gaagcacctg   19620
tttccatcat taataatgct gtttacacaa aggtagatgg tattgatgtg gagatctttg   19680
aaaataagac aacacttcct gttaatgttg catttgagct ttgggctaag cgtaacatta   19740
aaccagtgcc agagattaag atactcaata atttgggtgt tgatatcgct gctaatactg   19800
taatctggga ctacaaaaga gaagccccag cacatgtatc tacaataggt gtctgcacaa   19860
tgactgacat tgccaagaaa cctactgaga gtgcttgttc ttcacttact gtcttgtttg   19920
atggtagagt ggaaggacag gtagaccttt ttagaaacgc ccgtaatggt gttttaataa   19980
cagaaggttc agtcaaaggt ctaacacctt caaagggacc agcacaagct agcgtcaatg   20040
gagtcacatt aattggagaa tcagtaaaaa cacagtttaa ctactttaag aaagtagacg   20100
gcattattca acagttgcct gaaacctact ttactcagag cagagactta gaggatttta   20160
agcccagatc acaaatggaa actgactttc tcgagctcgc tatggatgaa ttcatacagc   20220
gatataagct cgagggctat gccttcgaac acatcgttta tggagatttc agtcatggac   20280
aacttggcgg tcttcatttt atgataggct tagccaagcg ctcacaagat tcaccactta   20340
aattagagga ttttatccct atggacagca cagtgaaaaa ttacttcata acagatgcgc   20400
aaacaggttc atcaaaatgt gtgtgttctg tgattgatct tttacttgat gactttgtcg   20460
agataataaa gtcacaagat tgtcagtga tttcaaaagt ggtcaaggtt acaattgact   20520
atgctgaaat ttcattcatg ctttggtgta aggatggaca tgttgaaacc ttctacccaa   20580
aactacaagc aagtcgagcg tggcaaccag gtgttgcgat gcctaacttg tacaagatgc   20640
aaagaatgct tcttgaaaag tgtgaccttc agaattatgg tgaaaatgct gttataccaa   20700
aaggaataat gatgaatgtc gcaaagtata ctcaactgtg tcaatactta aatacactta   20760 cttagctgt accctacaac atgagagtta ttcactttgg tgctggctct gataaaggag   20820
ttgcaccagg tacagctgtg ctcagacaat ggttgccaac tggcacacta cttgtcgatt   20880
cagatcttaa tgacttcgtc tccgacgcat attctacttt aattggagac tgtgcaacag   20940
```

```
tacatacggc taataaatgg gaccttatta ttagcgatat gtatgaccct aggaccaaac   21000
atgtgacaaa agagaatgac tctaaagaag ggttttttcac ttatctgtgt ggatttataa   21060
agcaaaaact agccctgggt ggttctatag ctgtaaagat aacagagcat tcttggaatg   21120 ctgacccttta caagcttatg ggccatttct catggtggac agcttttgtt acaaatgtaa   21180
atgcatcatc atcggaagca ttttttaattg gggctaacta tcttggcaag ccgaaggaac   21240
aaattgatgg ctataccatg catgctaact acattttctg gaggaacaca aatcctatcc   21300
agttgtcttc ctattcactc tttgacatga gcaaatttcc tcttaaatta agaggaactg   21360
ctgtaatgtc tcttaaggag aatcaaatca atgatatgat ttattctctt ctggaaaaag   21420
gtaggcttat cattagagaa acaacagag ttgtggtttc aagtgatatt cttgttaaca   21480
actaaacgaa catgtttatt tcttattat ttcttactct cactagtggt agtgaccttg   21540
accggtgcac cacttttgat gatgttcaag ctcctaatta cactcaacat acttcatcta   21600 tgagggggt ttactatcct gatgaaattt ttagatcaga cactctttat ttaactcagg   21660
atttatttct tccatttttat tctaatgtta cagggtttca tactattaat catacgtttg   21720
gcaaccctgt cataccttttt aaggatggta tttattttgc tgccacagag aaatcaaatg   21780
ttgtccgtgg ttgggttttt ggttctacca tgaacaacaa gtcacagtcg gtgattatta   21840
ttaacaattc tactaatgtt gttatacgag catgtaactt tgaattgtgt gacaacccctt   21900 tctttgctgt ttctaaaccc atgggtacac agacacatac tatgatattc gataatgcat   21960
ttaattgcac tttcgagtac atatctgatg ccttttcgct tgatgtttca gaaaagtcag   22020
gtaattttaa acacttacga gagtttgtgt ttaaaaataa agatgggttt ctctatgttt   22080
ataagggcta tcaacctata gatgtagttc gtgatctacc ttctggtttt aacactttga   22140
aacctatttt taagttgcct cttggtatta acattacaaa ttttagagcc attcttacag   22200 ccttttccacc tgctcaagac atttgggca cgtcagctgc agcctatttt gttggctatt   22260
taaagccaac tacatttatg ctcaagtatg atgaaaatgg tacaatcaca gatgctgttg   22320
attgttctca aaatccactt gctgaactca atgctctgt taagagcttt gagattgaca   22380
aaggaattta ccagacctct aatttcaggg ttgttccctc aggagatgtt gtgagattcc   22440
ctaatattac aaacttgtgt ccttttggag aggttttaa tgctactaaa ttcccttctg   22500
tctatgcatg ggagagaaaa aaaatttcta attgtgttgc tgattactct gtgctctaca   22560
actcaacatt tttttcaacc tttaagtgct atggcgtttc tgccactaag ttgaatgatc   22620
tttgcttctc caatgtctat gcagattctt ttgtagtcaa gggagatgat gtaagacaaa   22680
tagcgccagg acaaactggt gttattgctg attataatta taaattgcca gatgatttca   22740
tgggttgtgt ccttgcttgg aatactagga acattgatgc tacttcaact ggtaattata   22800
attataaata taggtatctt agacatggca agcttaggcc ctttgagaga gacatatcta   22860
atgtgccttt ctcccctgat ggcaaaccttt gcaccccacc tgctcttaat tgttattggc   22920
cattaaatga ttatgttttt tacaccacta ctggcattgg ctaccaacct acagagttg   22980 tagtactttc ttttgaactt ttaaatgcac cggccacggt ttgtggacca aaattatcca   23040
ctgaccttat taagaaccag tgtgtcaatt ttaatttta tggactcact ggtactggtg   23100
tgttaactcc ttcttcaaag agatttcaac catttcaaca atttggccgt gatgtttctg   23160
atttcactga ttccgttcga gatcctaaaa catctgaaat attagacatt tcaccttgcg   23220 cttttgggg tgtaagtgta attacacctg gaacaaatgc ttcatctgaa gttgctgttc   23280
tatatcaaga tgttaactgc actgatgttt ctacagcaat tcatgcagat caactcacac   23340
```

```
cagcttggcg catatattct actggaaaca atgtattcca gactcaagca ggctgtctta    23400
taggagctga gcatgtcgac acttcttatg agtgcgacat tcctattgga gctggcattt    23460
gtgctagtta ccatacagtt tctttattac gtagtactag ccaaaaatct attgtggctt    23520
atactatgtc tttaggtgct gatagttcaa ttgcttactc taataacacc attgctatac    23580
ctactaactt ttcaattagc attactacag aagtaatgcc tgtttctatg gctaaaacct    23640
ccgtagattg taatatgtac atctgcggag attctactga atgtgctaat ttgcttctcc    23700
aatatggtag cttttgcaca caactaaatc gtgcactctc aggtattgct gctgaacagg    23760
atcgcaacac acgtgaagtg ttcgctcaag tcaaacaaat gtacaaaacc ccaactttga    23820
aatattttgg tggttttaat ttttcacaaa tattacctga ccctctaaag ccaactaaga    23880
ggtcttttat tgaggacttg ctctttaata aggtgacact cgctgatgct ggcttcatga    23940
agcaatatgg cgaatgccta ggtgatatta atgctagaga tctcatttgt gcgcagaagt    24000
tcaatggact tacagtgttg ccacctctgc tcactgatga tatgattgct gcctacactg    24060
ctgctctagt tagtggtact gccactgctg gatggacatt tggtgctggc gctgctcttc    24120
aaataccttt tgctatgcaa atggcatata ggttcaatgg cattggagtt acccaaaatg    24180
ttctctatga gaaccaaaaa caaatcgcca accaatttaa caaggcgatt agtcaaattc    24240
aagaatcact tacaacaaca tcaactgcat gggcaagct gcaagacgtt gttaaccaga    24300
atgctcaagc attaaacaca cttgttaaac aacttagctc taattttggt gcaatttcaa    24360
gtgtgctaaa tgatatcctt tcgcgacttg ataaagtcga ggcggaggta caaattgaca    24420
ggttaattac aggcagactt caaagccttc aaacctatgt aacacaacaa ctaatcaggg    24480
ctgctgaaat cagggcttct gctaatcttg ctgctactaa aatgtctgag tgtgttcttg    24540
gacaatcaaa aagagttgac ttttgtggaa agggctacca ccttatgtcc ttcccacaag    24600
cagccccgca tggtgttgtc ttcctacatg tcacgtatgt gccatcccag gagaggaact    24660
tcaccacagc gccagcaatt tgtcatgaag gcaaagcata cttccctcgt gaaggtgttt    24720
ttgtgtttaa tggcacttct tggtttatta cacagaggaa cttcttttct ccacaaataa    24780
ttactacaga caatacattt gtctcaggaa attgtgatgt cgttattggc atcattaaca    24840
acacagttta tgatcctctg caacctgagc ttgactcatt caaagaagag ctggacaagt    24900
acttcaaaaa tcatacatca ccagatgttg atcttggcga catttcaggc attaacgctt    24960
ctgtcgtcaa cattcaaaaa gaaattgacc gcctcaatga ggtcgctaaa aatttaaatg    25020
aatcactcat tgaccttcaa gaattgggaa aatatgagca atatattaaa tggccttggt    25080
atgtttggct cggcttcatt gctggactaa ttgccatcgt catggttaca atcttgcttt    25140
gttgcatgac tagttgttgc agttgcctca agggtgcatg ctcttgtggt tcttgctgca    25200
agtttgatga ggatgactct gagccagttc tcaaggtgt caaattacat tacacataaa    25260
cgaacttatg gatttgttta tgagattttt tactcttgga tcaattactg cacagccagt    25320
aaaaattgac aatgcttctc ctgcaagtac tgttcatgct acagcaacga taccgctaca    25380
agcctcactc cctttcggat ggcttgttat tggcgttgca tttcttgctg ttttcagag    25440 cgctaccaaa ataattgcgc tcaataaaag atggcagcta gccctttata agggcttcca    25500
gttcatttgc aatttactgc tgctatttgt taccatctat tcacatcttt tgcttgtcgc    25560
tgcaggtatg gaggcgcaat ttttgtacct ctatgccttg atatattttc tacaatgcat    25620
caacgcatgt agaattatta tgagatgttg gctttgttgg aagtgcaaat ccaagaaccc    25680
attactttat gatgccaact actttgtttg ctggcacaca cataactatg actactgtat    25740
```

```
accatataac agtgtcacag atacaattgt cgttactgaa ggtgacggca tttcaacacc   25800
aaaactcaaa gaagactacc aaattggtgg ttattctgag gataggcact caggtgttaa   25860
agactatgtc gttgtacatg gctatttcac cgaagtttac taccagcttg agtctacaca   25920
aattactaca gacactggta ttgaaaatgc tacattcttc atctttaaca agcttgttaa   25980
agacccaccg aatgtgcaaa tacacacaat cgacggctct tcaggagttg ctaatccagc   26040
aatggatcca atttatgatg agccgacgac gactactagc gtgcctttgt aagcacaaga   26100
aagtgagtac gaacttatgt actcattcgt ttcggaagaa acaggtacgt taatagttaa   26160
tagcgtactt cttttcttg ctttcgtggt attcttgcta gtcacactag ccatccttac   26220
tgcgcttcga ttgtgtgcgt actgctgcaa tattgttaac gtgagtttag taaaaccaac   26280
ggtttacgtc tactcgcgtg ttaaaaatct gaactcttct gaaggagttc ctgatcttct   26340
ggtctaaacg aactaactat tattattatt ctgtttggaa ctttaacatt gcttatcatg   26400
gcagacaacg gtactattac cgttgaggag cttaaacaac tcctggaaca atggaaccta   26460
gtaataggtt tcctattcct agcctggatt atgttactac aatttgccta ttctaatcgg   26520
aacaggtttt tgtacataat aaagcttgtt ttcctctggc tcttgtggcc agtaacactt   26580
gcttgttttg tgcttgctgc tgtctacaga attaattggg tgactggcgg gattgcgatt   26640
gcaatggctt gtattgtagg cttgatgtgg cttagctact tcgttgcttc cttcaggctg   26700
tttgctcgta cccgctcaat gtggtcattc aacccagaaa caaacattct tctcaatgtg   26760
cctctccggg ggacaattgt gaccagaccg ctcatggaaa gtgaacttgt cattggtgct   26820
gtgatcattc gtggtcactt gcgaatggcc ggacactccc tagggcgctg tgacattaag   26880
gacctgccaa aagagatcac tgtggctaca tcacgaacgc tttcttatta caaattagga   26940
gcgtcgcagc gtgtaggcac tgattcaggt tttgctgcat acaaccgcta ccgtattgga   27000
aactataaat taaatacaga ccacgccggt agcaacgaca atattgcttt gctagtacag   27060
taagtgacaa cagatgtttc atcttgttga cttccaggtt acaatagcag agatattgat   27120
tatcattatg aggactttca ggattgctat ttggaatctt gacgttataa taagttcaat   27180
agtgagacaa ttatttaagc ctctaactaa gaagaattat tcggagttag atgatgaaga   27240
acctatggag ttagattatc cataaaacga acatgaaaat tattctcttc ctgacattga   27300
ttgtatttac atcttgcgag ctatatcact atcaggagtg tgttagaggt acgactgtac   27360
tactaaaaga accttgccca tcaggaacat acgagggcaa ttcaccattt caccctcttg   27420
ctgacaataa atttgcacta acttgcacta gcacacactt tgcttttgct tgtgctgacg   27480
gtactcgaca tacctatcag ctgcgtgcaa gatcagtttc accaaaactt ttcatcagac   27540
aagaggaggt tcaacaagag ctctactcgc cacttttct cattgttgct gctctagtat   27600
ttttaatact ttgcttcacc attaagagaa agacagaatg aatgagctca ctttaattga   27660
cttctatttg tgcttttag cctttctgct attccttgtt ttaataatgc ttattatatt   27720
ttggttttca ctcgaaatcc aggatctaga agaaccttgt accaaagtct aaacgaacat   27780
gaaacttctc attgttttga cttgtatttc tctatgcagt tgcatatgca ctgtagtaca   27840
gcgctgtgca tctaataaac ctcatgtgct tgaagatcct tgtaaggtac aacactaggg   27900
gtaatactta tagcactgct tggctttgtg ctctaggaaa ggttttacct tttcatagat   27960
ggcacactat ggttcaaaca tgcacaccta atgttactat caactgtcaa gatccagctg   28020
gtggtgcgct tatagctagg tgttggtacc ttcatgaagg tcaccaaact gctgcattta   28080
gagacgtact tgttgtttta aataaacgaa caaattaaaa tgtctgataa tggaccccaa   28140
```

```
tcaaaccaac gtagtgcccc ccgcattaca tttggtggac ccacagattc aactgacaat    28200
aaccagaatg gaggacgcaa tggggcaagg ccaaaacagc gccgacccca aggtttaccc    28260
aataatactg cgtcttggtt cacagctctc actcagcatg gcaaggagga acttagattc    28320
cctcgaggcc agggcgttcc aatcaacacc aatagtggtc cagatgacca aattggctac    28380
taccgaagag ctacccgacg agttcgtggt ggtgacggca aaatgaaaga gctcagcccc    28440
agatggtact tctattacct aggaactggc ccagaagctt cacttcccta cggcgctaac    28500
aaagaaggca tcgtatgggt tgcaactgag ggagccttga atacacccaa agaccacatt    28560
ggcacccgca atcctaataa caatgctgcc accgtgctac aacttcctca aggaacaaca    28620
ttgccaaaag gcttctacgc agagggaagc agaggcggca gtcaagcctc ttctcgctcc    28680
tcatcacgta gtcgcggtaa ttcaagaaat tcaactcctg gcagcagtag gggaaattct    28740
cctgctcgaa tggctagcgg aagtggtgaa actgccctcg cgctattgct gctagacaga    28800
ttgaaccagc ttgagagcaa agtttctggt aaaggccaac aacaacaagg ccaaactgtc    28860
actaagaaat ctgctgctga ggcatctaaa aagcctcgcc aaaaacgtac tgccacaaaa    28920
cagtacaacg tcactcaagc atttgggaga cgtggtccag aacaacccca aggaaatttc    28980
ggggaccaag acctaatcag acaaggaact gattacaaac attggccgca aattgcacaa    29040
tttgctccaa gtgcctctgc attctttgga atgtcacgca ttggcatgga agtcacacct    29100
tcgggaacat ggctgactta tcatggagcc attaaattgg atgacaaaga tccacaattc    29160
aaagacaacg tcatactgct gaacaagcac attgacgcat acaaaacatt cccaccaaca    29220
gagcctaaaa aggacaaaaa gaaaaagact gatgaagctc agccttttgcc gcagagacaa    29280 aagaagcagc ccactgtgac tcttcttcct gcggctgaca tggatgattt ctccagacaa    29340
cttcaaaatt ccatgagtgg agcttctgct gattcaactc aggcataaac actcatgatg    29400
accacacaag gcagatgggc tatgtaaacg ttttcgcaat tccgtttacg atacatagtc    29460
tactcttgtg cagaatgaat tctcgtaact aaacagcaca gtaggttta gttaacttta    29520 atctcacata gcaatcttta atcaatgtgt aacattaggg aggacttgaa agagccacca    29580
cattttcatc gaggccacgc ggagtacgat cgagggtaca gtgaataatg ctaggagag    29640 ctgcctatat ggaagagccc taatgtgtaa aattaatttt agtagtgcta tccccatgtg    29700
attttaatag cttcttagga gaatgacaaa aaaaaaaaaa aaaaaaaaa a              29751
```

<210> SEQ ID NO 2
<211> LENGTH: 383
<212> TYPE: RNA
<213> ORGANISM: Hepatitis C virus

<400> SEQUENCE: 2

```
gccagccccc ugauggggc gacacuccac cauagaucac ucccuguga ggaacuacug      60 ucuucaccca gaaagcgucu agccauggcg uuaguaugag ugucgugcag ccuccaggac    120
ccccccuccc gggagagcca uaguggucug cggaaccggu gaguacaccg gaauugccag    180
gacgaccggg uccuuucuug gaucaacccg cucaugccu ggagauuugg gcgugccccc    240
gcaagacugc uagccgagua guguggguc gcgaaaggcc uuguggucacu gccugauagg    300 gugcuugcga gugccccggg aggucucgua gaccgugcac caugagcacg aauccuaaac    360
cucaaagaaa aaccaaacgu aac                                            383
```

<210> SEQ ID NO 3
<211> LENGTH: 21

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
guacugccug auagggugcu u                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gcacccuauc aggcaguacu u                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cguacgcgga auacuucgau u                                              21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ucgaaguauu ccgcguacgu u                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cuuacgcuga guacuucgau u                                              21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ucgaaguacu cagcguaagu u                                              21

<210> SEQ ID NO 9
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 9
aucucuacgg ugguccuaau u                                              21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uuaggaccac cguagagauu u                                              21

<210> SEQ ID NO 11
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
cccugugagg aacuacuguc uuc                                            23

<210> SEQ ID NO 12
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
uacugucuuc acgcagaaag cgu                                            23

<210> SEQ ID NO 13
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cgagacugcu agccgaguag ugu                                            23

<210> SEQ ID NO 14
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gaauccuaaa ccucaaagaa aaa                                            23

<210> SEQ ID NO 15
<211> LENGTH: 23
<212> TYPE: RNA
<213> ORGANISM: Artificial Sequence
<220> FEATURE:
<223> OTHER INFORMATION: Description of Artificial Sequence: Synthetic
```

-continued

```
        oligonucleotide

<400> SEQUENCE: 15
ggucagaucg ucgguggagu uua                                             23

<210> SEQ ID NO 16
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gguaagguca ucgauacccu cac                                             23

<210> SEQ ID NO 17
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
acggcgugaa cuaugcaaca ggg                                             23

<210> SEQ ID NO 18
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ccgguugcuc cuuuucuauc uuc                                             23

<210> SEQ ID NO 19
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gcucuucaua cggauuccaa uac                                             23

<210> SEQ ID NO 20
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cauacggauu ccaauacucu ccu                                             23

<210> SEQ ID NO 21
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 21
uuugacucaa cggucacuga gaa                                                23

<210> SEQ ID NO 22
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ccuucacgga ggcuaugacu aga                                                23

<210> SEQ ID NO 23
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
auacgacuug gaguugauaa cau                                                23

<210> SEQ ID NO 24
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
auuccuggcu aggcaacauc auc                                                23

<210> SEQ ID NO 25
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uuguggcaag uaccucuuca acu                                                23

<210> SEQ ID NO 26
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
auguggugcc uacuccuacu uuc                                                23

<210> SEQ ID NO 27
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27

-continued cuuuggluggc uccaucuuag ccc        23

<210> SEQ ID NO 28
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gucacggcua gcugugaaag guc        23

<210> SEQ ID NO 29
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
agccgcuuga cugcagagag ugc        23

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cugugaggaa cuacugucuu c        21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
agacaguagu uccucacagg g        21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
cugucuucac gcagaaagcg u        21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
gcuuucugcg ugaagacagu a        21

-continued

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
agacugcuag ccgaguagug u                                                21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
acuacucggc uagcagucuc g                                                21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
auccuaaacc ucaaagaaaa a                                                21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
uuucuuugag guuuaggauu c                                                21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ucagaucguc gguggaguuu a                                                21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
aacuccaccg acgaucugac c                                                21

<210> SEQ ID NO 40

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
uaaggucauc gauacccuca c                                              21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gaggguaucg augaccuuac c                                              21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ggcgugaacu augcaacagg g                                              21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
cguuugcaua guucacgccg u                                              21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gguugcuccu uuucuaucuu c                                              21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
agauagaaaa ggagcaaccg g                                              21

<210> SEQ ID NO 46
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 46
ucuucauacg gauuccaaua c                                              21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
auuggaaucc guaugaagag c                                              21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uacggauucc aauacucucc u                                              21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
gagaguauug gaauccguau g                                              21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ugacucaacg gucacugaga a                                              21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cucagugacc guugagucaa a                                              21

<210> SEQ ID NO 52
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 52
uucacggagg cuaugacuag a                                              21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uagucauagc cuccgugaag g                                              21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
acgacuugga guugauaaca u                                              21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
guuaucaacu ccaagucgua u                                              21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
uccuggcuag gcaacaucau c                                              21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
ugauguugcc uagccaggaa u                                              21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 58
guggcaagua ccucuucaac u                                              21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uugaagaggu acuugccaca a                                              21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
guggugccua cuccuacuuu c                                              21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
aaguaggagu aggcaccaca u                                              21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
uugguggcuc caucuuagcc c                                              21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
gcuaagaugg agccaccaaa g                                              21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
```

```
cacggcuagc ugugaaaggu c                                              21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
ccuuucacag cuagccguga c                                              21

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
ccgcuugacu gcagagagug c                                              21

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
acucucugca gucaagcggc u                                              21

<210> SEQ ID NO 68
<211> LENGTH: 10
<212> TYPE: DNA
<213> ORGANISM: SARS coronavirus

<400> SEQUENCE: 68
taaaacgaac                                                           10
```